US006218120B1

(12) United States Patent
Rozen et al.

(10) Patent No.: US 6,218,120 B1
(45) Date of Patent: *Apr. 17, 2001

(54) METHODS FOR DETECTING HUMAN METHYLENE TETRAHYDROFOLATE REDUCTASE ALLELIC VARIANTS

(75) Inventors: Rima Rozen; Philippe Goyette, both of Montreal (CA)

(73) Assignee: McGill University, Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/258,928

(22) Filed: Mar. 1, 1999

Related U.S. Application Data

(63) Continuation-in-part of application No. 08/738,000, filed as application No. PCT/CA95/00314 on May 25, 1995, now Pat. No. 6,074,821.

(30) Foreign Application Priority Data

May 26, 1994 (GB) .................................................. 9410620

(51) Int. Cl.[7] .............................. C12Q 1/68; C12P 19/34; C07H 21/04
(52) U.S. Cl. .......................... 435/6; 435/91.2; 536/24.31; 536/24.33; 536/23.5; 536/23.2
(58) Field of Search ...................... 435/6, 91.2; 536/23.7, 536/24.31, 24.33, 23.2

(56) References Cited

U.S. PATENT DOCUMENTS

| 5,972,614 | 10/1999 | Ruano et al. ............................. 435/6 |
| 6,008,221 | 12/1999 | Smith et al. .......................... 514/254 |

FOREIGN PATENT DOCUMENTS

| 95/33054 | * 12/1995 | (WO) . |
| WO 00/04194 | 1/2000 | (WO) . |

OTHER PUBLICATIONS

Weisberg et al. Molecular Genetics and Metabolism. 64: 169–172, Jul. 1998.*
Akar et al. Thrombosis Research. 97:163–167, Feb. 2000.*
van Ede et al. Seminars in Arthritis and Rheumatism. 27: 277–292, Apr. 1998.*
van der Put et al. American Journal of Human Genetics. 62: 1044–1051, Apr. 1998.*
Haagsma et al. Ann Rheum Disease. 58:79–84, Jul. 1998.*
Goyette P et al., *Nature Genetics*, 1994, 7:195–200.
Goyette P et al., *AM. J. Hum. Genet.*, 1995, 56:1052–1059.
Frosst P et al., *Nature Genetics*, 1995, 10:111–113.
Orita, M. et al., *Genomics*, 1989, 5:8874–8879.
Engbersen et al., *Am. J. Hum. Genet.*, 1995, 56:142–150.
Frosst, P. et al., *Nat. Genet.*, 1995, 10:111–113.
Viel, A. et al., *Brit. J. Cancer*, 1997, 75:1105–1110.
Goyette, P. et al., *Am. J. Hum. Genet.*, 1995, 56:1052–1059.
Christensen, B. et al., *Arterioscler. Thromb. Vasc. Biol.*, 1997, 17:569–573.
Jacques, P.F. et al, *Circulation*, 1996, 93:7–9.
Lanoue, L. et al., Experimental Biology '97, Apr. 1997, New Orleans.
Araki et al., "Determination of free and total homocysteine in human plasma by high–performance liquid chromatography with fluorescence detection," *J. Chromatography* 422:43–52 (1987).

(List continued on next page.)

*Primary Examiner*—Carla J. Myers
(74) *Attorney, Agent, or Firm*—Clark & Elbing LLP

(57) ABSTRACT

Provided herein is a heretofore unknown isolated nucleic acid molecule which encodes human methylenetetrahydrofolate reducatase, along with an amino acid sequence of methylenetetrahydrofolate reductase, and a cDNA probe for human methylenetetrahydrofolate reductase. Also provided are a molecule description of mutations in humans resulting in a phenotype having reduced levels of methylenetetrahydrofolate reductase, and methods of diagnosing methylenetetrahydrofolate reductase deficiency in a human.

12 Claims, 24 Drawing Sheets

OTHER PUBLICATIONS

Boushey et al., "A quantitative assessment of plasma homocysteine as a risk factor for vascular disease. Probable benefits of increasing folic acid intakes," *JAMA* 274:1049–1057 (1995).

Brattstrom et al., "Plasma homocysteine and methionine tolerance in early–onset vascular disease," *Homeostasis* 19:35–44 (1989).

Breier et al., "National Institute of Mental Health longitudinal study of chronic schizophrenia. Prognosis and predictors of outcome," *Arch. Gen. Psychiatry* 48:239–246 (1991).

Clarke et al., "Hyperhomocysteinemia: an independent risk factor for vascular disease," *N. Engl. J. Med.* 324:1149–1155 (1991).

Cormack, "Directed mutagenesis using the polymerase chain reaction," *Current Protocols in Molecular Biology* 1: 8.5.1–8.5.9, John Wiley & Sons, New York (1995).

Endicott et al., "The global assessment scale, a procedure for measuring overall severity of psychiatric disturbance," *Arch. Gen. Psychiatry* 33:766–771 (1976).

Fletcher et al., "MTHFR association with arteriosclerotic vascular disease," *Human Genet.* 103:11–21 (1998).

Goyette et al., "Severe and mild mutations in cis for the methylenetetrahydrofolate reductase (MTHFR) gene, and description of five novel mutations in MTHFR," *Am. J. Hum. Genet.* 59:1268–1275 (1996).

Haworth et al., "Symptomatic and asymptomatic methylenetetrahydrofolate reductase deficiency in two adult brothers," *Am. J. of Medical Genetics* 45:572–576 (1993).

Higgins et al., "NHLBI Family Heart Study: Objectives and Design," *Am. J. Epidemiol.* 143:1219–1228 (1996).

Joober et al., "Polyglutamine–containing proteins in schizophrenia," *Mol. Psychiatry* 4:53–57 (1999).

Kane et al., "Clozapine for the treatment–resistant schizophrenic. A double–blind comparison with chlorpromazine," *Arch. Gen. Psychiatry* 45:789–796 (1988).

Kang et al., "Thermolabile methylenetetrahydrofolate reductase: An inherited risk factor for coronary artery disease," *Am. J. Human Genet.* 48:536–545 (1991).

Kluijtmans et al., "Molecular genetic analysis in mild hyperhomocysteinemia: A common mutation in methylenetetrahydrofolate reductase gene is a risk factor for cardiovascular disease," *Am. J. Hum. Genet.* 58:35–41 (1996).

Matthews, "Methylentetrahydrofolate reductase from pig liver," *Methods in Enzymology Vitamines and Coenzymes Part G* 122: 372–381 (1986).

Morita et al., "Genetic polymorphism of 5,10 methylenetetrahydrofolate reductase (MTHFR) as a risk factor for coronary artery disease," *Circulation* 95:2032–2036 (1997).

Niefind et al., "Amino acid similarity coefficients for protein modeling and sequence alignment derived from main–chain folding angles," *J. Mol. Biol.* 219:481–497 (1991).

Nurnberger et al., "Diagnostic interview for genetic studies. Rationale, unique features, and training. NIMH Genetics Initiative," *Arch. Gen. Psychiatry* 51:849–859, discussion 863–864 (1994).

Refsum et al., "Homocysteine and vascular disease," *Annu. Rev. Medicine* 48:31–62 (1998).

Rozen, "Molecualr genetics of methylenetetrahydrofolate reductase deficiency," *J. Inher. Metab. Dis.* 19:589–594 (1996).

Saint–Girons et al., "Nucleotide sequence of metF, the *E.coli* structural gene for 5–10 methylene tetrahydrofolate reductase and of its control region," *Nucleic Acids Research* 11:6723–6732 (1983).

Selhub et al., "Association between plasma homocysteine concentrations and extra–cranial carotid artery stenosis," *N. Engl. J. Med.* 332:286–291 (1995).

Shin–Buehring et al., "A new enzymatic method for pyridoxal–5–phosphate determination," *J. Inherit. Metab. Disorders* 4:123–124 (1981).

Szymanski et al., "Gender differences in onset of illness, treatment response, course, and biologic indexes in first–episode schizophrenic patients," *Am. J. Psychiatry* 152:698–703 (1995).

Tsuang et al., "Heterogeneity of schizophrenia. Conceptual models and analytic strategies," *Br. J. Psychiatry* 156:17–26 (1990).

van der Put et al., "Mutated methylenetetrahydrofolate reductase as a risk factor for spina bifida," *Lancet* 346:1070–1071 (1995).

Whitehead et al., "A genetic defect in 5, 10 methylenetetrahydrofolate reductase in neural tube defects," *Q J Med.* 88:763–766 (1995).

Woerner et al., "Anchoring the BPRS: an aid to improved reliability," *Psychopharmacol. Bull.* 24:112–117 (1988).

Wyatt, "Neuroleptics and the natural course of schizophrenia," *Schizophr. Bull.* 17:325–351 (1991).

Yang et al., "Molecular cloning and nucleotide sequence analysis of the *Saccharomyces cerevisiae RAD1* gene," *Mol. Cell. Biol.* 4:2161–2169 (1984).

Arinami et al., "Methylenetetrahydrofolate Reductase Variant and Schizophrenia/Depression," *Amer. J. of Medical Genetics* 74:526–528 (1997).

Arranz et al., "Evidence for association between polymorphisms in the promoter and coding regions of the 5–HT$_{2A}$ receptor gene and response to clozapine," *Molecular Psychiatry* 3:61–66 (1998).

Bakker et al., "Hyperhomocysteinaemia and associated disease," *Pharm. World Sci.* 19:126–132 (1997).

Dalman et al., "Obstetric complications and the risk of schizophrenia; a longitudinal study of a national birth cohort," *Arch. Gen. Psychiatry* 56:234–240 (1999).

Drazen et al., "Treatment of Asthma with Drugs Modifying the Leukotriene Pathway," *N.E. Journal of Medicine* 340:197–206 (1999).

Freeman et al., "Folate–Responsive Homocystinuria and Schizophrenia. A defect in Methylation Due to Deficient 5, 10–Methylenetetrahydrofolate Reductase Activity," *N.E. Journal of Medicine* 292:491–496 (1975).

Gallagher et al., "Homocysteine and risk of premature coronary heart disease. Evidence for a common gene mutation," *Circulation* 94:2154–2158 (1996).

Goyette et al., "Gene structure of human and mouse methylenetetrahydrofolate reductase (MTHFR)," *Mammalian Genome* 9:652–656 (1998).

Grandone et al., "Factor V Leiden, C>T MTHFR polymorphism and genetic susceptibility to preeclampsia," *Thromb. Haemost.* 77:1052–1054 (1997).

Grandone et al., "Methylenetetrahydrofolate reductase (MTHFR) 677—>C mutation and unexplained early pregnancy loss [letter]," *Thrombosis & Haemostasis* 79:1056–1057 (1998).

Grieco, "Homocystinuria: pathogenetic mechanisms," *Am. J. Med. Sci.* 273:120–132 (1977).

Gudnason et al., "C677T (thermolabile alanine/valine) polymorphism in methylenetetrahydrofolate reductase (MTHFR): its frequency and impact on plasma homocysteine concentration in different European populations." *Atherosclerosis* 136:347–354 (1998).

Hol et al., "Molecular genetic analysis of the gene encoding the trifunctional enzyme MTHFD (methylenetetrahydrofolate–dehydrogenase, methylenetetrahydrofolate–cyclohydrolase, formyltetrahydrofolate synthetase) in patients with neural tube defects," *Clin. Genet.* 53:119–125 (1998).

James et al., "Abnormal folate metabolism and mutation in the methylenetetrahydrofolate reductase gene may be maternal risk factors for Down syndrome," *Am. J. Clin. Nutr.* 70:495–501 (1999).

Koreen et al., "Plasma Homovanillic Acid Levels in First–Episode Schizophrenia. Psychopathology and treatment response," *Arch Gen. Psychiatry* 51:132–138 (1994).

Kuivenhoven et al., "The Role of a Common Variant of the Cholesteryl Esterr Transfer Protein Gene in the Progression of Coronary Atherosclerosis," *N.E. Journal of Medicine* 338:86–93 (1998).

Kunugi et al., "C677T polymorphism in methylenetetrahydrofolate reductase gene and psychoses," *Mol. Psychiatr.* 3:435–437 (1998).

Matthews et al., "Methylenetetrahydrofolate reductase and methionine synthase: biochemistry and molecular biology," *Eur. J. Pediatr.* 157:S54–S59 (1998).

Molimard et al., "Does use of withdrawal of long–acting $\beta_2$–adrenoceptor induce desensitisation?," *Lancet* 351:66–67 (1998).

Mudd et al., "$N^{5,10}$–Methylenetetrahydrofolate reductase deficiency and schizophrenia: a working hypothesis," *J. Psychiat. Res.* 11: 259–262, (1974).

Pasquier et al., "Methylenetetrahydrofolate reductase deficiency revealed by a neuropathy in a psychotic adult [letter]," *Journal of Neurology, Neurosurgery & Psychiatry* 57:765–766 (1994).

Poirer et al., "Apolipoprotein E4 allele as a predictor of cholinergic deficits and treatment outcome in Alzheimer disease," *Proc. Natl. Acad. Sci. USA* 92:12260–12264 (1995).

Regland et al., "Homocysteinemia and schizophrenia as a case of methylation deficiency," *Journal of Neural Transmission–General Section* 98:143–152 (1994).

Regland et al., "Homocysteinemia is a common feature of schizophrenia," *Journal of Neural Transmission–General Section* 100:165–169 (1995).

Regland et al., "Homozygous thermolabile methylenetetrahydrofolate reductase in schizophrenia–like psychosis," *Journal of Neural Transmission* 104:931–941 (1997).

Smeraldi et al., "Polymorphism within the promoter of the serotonin transporter gene and antidepressant efficacy of fluvoxamine," *Molecular Psychiatry* 3:508–511 (1998).

Sohda et al., "Methylenetetrahydrofolate reductase polymorphism and pre–eclampsia," *J. Med. Genet* 34:525–526 (1997).

Spire–Vayron de la Moureyre et al., "Genotypic and phenotypic analysis of the polymorphic thiopurine S–methyltransferase gene (TPMT) in a European population," *British Journal of Pharmacology* 125:879–887 (1998).

Stauffer et al., "Cloning and nucleotide sequence of the *Salmonella typhimurium* LT2 metF gene and its homology with the corresponding sequence of *Escherichia coli*," *Mol. Gen. Genet.* 212:246–251 (1988).

Tan et al., "Association between $\beta_2$–adrenoceptor polymorphism and susceptibility to bronchodilator desensitisation in moderately severe stable asthmatics," *Lancet* 350:995–999 (1997).

Tan et al. "Does use of withdrawal of long–acting $\beta_2$–adrenoceptor induce desensitisation?," (Author's reply) *Lancet* 351:67 (1998).

*Third Wave Technologies*, "Third Wave Technologies Launches Third Pharmacogenetic Product. Oligonucleotide Sets and Assay Controls Specific for MTHFR Mutation," News release Dec. (1999).

Ueda et al., "ACE (I/D) Genotype as a Predictor of the Magnitude and Duration of the Response to an ACE Inhibitor Drug (Enalaprilat) in Humans," *Circulation* 98:2148–2153 (1998).

Zhou et al., "Purification and Characterization of Methylenetetrahydrofolate Reductase from Human Cadaver Liver," *Biochemical Medicine and Metabolic biology* 43:234–242 (1990).

* cited by examiner

```
          10        20        30        40        50
       x    x    x    x    x    x    x    x    x    x
AAT TCC GGA GCC ATG GTG AAC GAA GCC AGA GGA AAC AGC AGC CTC AAC CCC
TTA AGG CCT CGG TAC CAC TTG CTT CGG TCT CCT TTG TCG TCG GAG TTG GGG
Asn Ser Gly Ala Met Val Asn Glu Ala Arg Gly Asn Ser Ser Leu Asn Pro, 60        70        80        90       100
       x    x    x    x    x    x    x    x    x    x
TGC TTG GAG GGC AGT GCC AGC AGT GGC AGT GAG AGC TCC AAA GAT AGT TCG
ACG AAC CTC CCG TCA CGG TCG TCA CCG TCA CTC TCG AGG TTT CTA TCA AGC
Cys Leu Glu Gly Ser Ala Ser Ser Gly Ser Glu Ser Ser Lys Asp Ser Ser, 110       120       130       140       150
       x    x    x    x    x    x    x    x    x    x
AGA TGT TCC ACC CCG GGC CTG GAC CCT GAG CGG CAT GAG AGA CTC CGG GAG
TCT ACA AGG TGG GGC CCG GAC CTG GGA CTC GCC GTA CTC TCT GAG GCC CTC
Arg Cys Ser Thr Pro Gly Leu Asp Pro Glu Arg His Glu Arg Leu Arg Glu, 160       170       180       190       200
       x    x    x    x    x    x    x    x    x    x
AAG ATG AGG CGG CGA TTG GAA TCT GGT GAC AAG TGG TTC TCC CTG GAA TTC
TTC TAC TCC GCC GCT AAC CTT AGA CCA CTG TTC ACC AAG AGG GAC CTT AAG
Lys Met Arg Arg Arg Leu Glu Ser Gly Asp Lys Trp Phe Ser Leu Glu Phe, 210       220       230       240       250
       x    x    x    x    x    x    x    x    x    x
TTC CCT CCT CGA ACT GCT GAG GGA GCT GTC AAT CTC ATC TCA AGG TTT GAC
AAG GGA GGA GCT TGA CGA CTC CCT CGA CAG TTA GAG TAG AGT TCC AAA CTG
Phe Pro Pro Arg Thr Ala Glu Gly Ala Val Asn Leu Ile Ser Arg Phe Asp, 260       270       280       290       300
       x    x    x    x    x    x    x    x    x    x
CGG ATG GCA GCA GGT GGC CCC CTC TAC ATA GAC GTG ACC TGG CAC CCA GCA
GCC TAC CGT CGT CCA CCG GGG GAG ATG TAT CTG CAC TGG ACC GTG GGT CGT
Arg Met Ala Ala Gly Gly Pro Leu Tyr Ile Asp Val Thr Trp His Pro Ala, 310       320       330       340       350
       x    x    x    x    x    x    x    x    x    x
GGT GAC CCT GGC TCA GAC AAG GAG ACC TCC TCC ATG ATG ATC GCC AGC ACC
CCA CTG GGA CCG AGT CTG TTC CTC TGG AGG AGG TAC TAC TAG CGG TCG TGG
Gly Asp Pro Gly Ser Asp Lys Glu Thr Ser Ser Met Met Ile Ala Ser Thr,
```

Fig. 1A

```
      360         370         380         390         400
       :           :           :           :           :
GCC GTG AAC TAC TGT GGC CTG GAG ACC ATC CTG CAC ATG ACC TGC TGC CGT
CGG CAC TTG ATG ACA CCG GAC CTC TGG TAG GAC GTG TAC TGG ACG ACG GCA
Ala Val Asn Tyr Cys Gly Leu Glu Thr Ile Leu His Met Thr Cys Cys Arg, 410         420         430         440         450
       :           :           :           :           :
CAG CGC CTG GAG GAG ATC ACG GGC CAT CTG CAC AAA GCT AAG CAG CTG GGC
GTC GCG GAC CTC CTC TAG TGC CCG GTA GAC GTG TTT CGA TTC GTC GAC CCG
Gln Arg Leu Glu Glu Ile Thr Gly His Leu His Lys Ala Lys Gln Leu Gly, 460         470         480         490         500         510
       :           :           :           :           :           :
CTG AAG AAC ATC ATG GCG CTG CGG GGA GAC CCA ATA GGT GAC CAG TGG GAA
GAC TTC TTG TAG TAC CGC GAC GCC CCT CTG GGT TAT CCA CTG GTC ACC CTT
Leu Lys Asn Ile Met Ala Leu Arg Gly Asp Pro Ile Gly Asp Gln Trp Glu, 520         530         540         550         560
             :           :           :           :           :
GAG GAG GAG GGA GGC TTC AAC TAC GCA GTG GAC CTG GTG AAG CAC ATC CGA
CTC CTC CTC CCT CCG AAG TTG ATG CGT CAC CTG GAC CAC TTC GTG TAG GCT
Glu Glu Glu Gly Gly Phe Asn Tyr Ala Val Asp Leu Val Lys His Ile Arg, 570         580         590         600         610
             :           :           :           :           :
AGT GAG TTT GGT GAC TAC TTT GAC ATC TGT GTG GCA GGT TAC CCC AAA GGC
TCA CTC AAA CCA CTG ATG AAA CTG TAG ACA CAC CGT CCA ATG GGG TTT CCG
Ser Glu Phe Gly Asp Tyr Phe Asp Ile Cys Val Ala Gly Tyr Pro Lys Gly, 620         630         640         650         660
             :           :           :           :           :
CAC CCC GAA GCA GGG AGC TTT GAG GCT GAC CTG AAG CAC TTG AAG GAG AAG
GTG GGG CTT CGT CCC TCG AAA CTC CGA CTG GAC TTC GTG AAC TTC CTC TTC
His Pro Glu Ala Gly Ser Phe Glu Ala Asp Leu Lys His Leu Lys Glu Lys, 670         680         690         700         710
             :           :           :           :           :
GTG TCT GCG GGA GCC GAT TTC ATC ATC ACG CAG CTT TTC TTT GAG GCT GAC
CAC AGA CGC CCT CGG CTA AAG TAG TAG TGC GTC GAA AAG AAA CTC CGA CTG
Val Ser Ala Gly Ala Asp Phe Ile Ile Thr Gln Leu Phe Phe Glu Ala Asp,
```

Fig. 1B

```
          720           730           740           750           760
           x    x    x    x    x    x    x    x    x    x    x
          ACA  TTC  TTC  CGC  TTT  GTG  AAG  GCA  TGC  ACC  GAC  ATG  GGC  ATC  ACT  TGC  CCC
          TGT  AAG  AAG  GCG  AAA  CAC  TTC  CGT  ACG  TGG  CTG  TAC  CCG  TAG  TGA  ACG  GGG
          Thr  Phe  Phe  Arg  Phe  Val  Lys  Ala  Cys  Thr  Asp  Met  Gly  Ile  Thr  Cys  Pro>

770           780           790           800           810
           x    x    x    x    x    x    x    x    x    x    x
          ATC  GTC  CCC  GGG  ATC  TTT  CCC  ATC  CAG  GGC  TAC  CAC  TCC  CTT  CGG  CAG  CTT
          TAG  CAG  GGG  CCC  TAG  AAA  GGG  TAG  GTC  CCG  ATG  GTG  AGG  GAA  GCC  GTC  GAA
          Ile  Val  Pro  Gly  Ile  Phe  Pro  Ile  Gln  Gly  Tyr  His  Ser  Leu  Arg  Gln  Leu>

820           830           840           850           860
           x    x    x    x    x    x    x    x    x    x    x
          GTG  AAG  CTG  TCC  AAG  CTG  GAG  GTG  CCA  CAG  GAG  ATC  AAG  GAC  GTG  ATT  GAG
          CAC  TTC  GAC  AGG  TTC  GAC  CTC  CAC  GGT  GTC  CTC  TAG  TTC  CTG  CAC  TAA  CTC
          Val  Lys  Leu  Ser  Lys  Leu  Glu  Val  Pro  Gln  Glu  Ile  Lys  Asp  Val  Ile  Glu>

870           880           890           900           910
           x    x    x    x    x    x    x    x    x    x    x
          CCA  ATC  AAA  GAC  AAC  GAT  GCT  GCC  ATC  CGC  AAC  TAT  GGC  ATC  GAG  CTG  GCC
          GGT  TAG  TTT  CTG  TTG  CTA  CGA  CGG  TAG  GCG  TTG  ATA  CCG  TAG  CTC  GAC  CGG
          Pro  Ile  Lys  Asp  Asn  Asp  Ala  Ala  Ile  Arg  Asn  Tyr  Gly  Ile  Glu  Leu  Ala>

920           930           940           950           960
           x    x    x    x    x    x    x    x    x    x    x
          GTG  AGC  CTG  TGC  CAG  GAG  CTT  CTG  GCC  AGT  GGC  TTG  GTG  CCA  GGC  CTC  CAC
          CAC  TCG  GAC  ACG  GTC  CTC  GAA  GAC  CGG  TCA  CCG  AAC  CAC  GGT  CCG  GAG  GTG
          Val  Ser  Leu  Cys  Gln  Glu  Leu  Leu  Ala  Ser  Gly  Leu  Val  Pro  Gly  Leu  His>

970           980           990          1000          1010         1020
           x    x    x    x    x    x    x    x    x    x    x
          TTC  TAC  ACC  CTC  AAC  CGC  GAG  ATG  GCT  ACC  ACA  GAG  GTG  CTG  AAG  CGC  CTG
          AAG  ATG  TGG  GAG  TTG  GCG  CTC  TAC  CGA  TGG  TGT  CTC  CAC  GAC  TTC  GCG  GAC
          Phe  Tyr  Thr  Leu  Asn  Arg  Glu  Met  Ala  Thr  Thr  Glu  Val  Leu  Lys  Arg  Leu>

1030          1040          1050          1060         1070
                        x    x    x    x    x    x    x    x    x    x
                       GGG  ATG  TGG  ACT  GAG  GAC  CCC  AGG  CGT  CCC  CTA  CCC  TGG  GCT  CTC  AGT  GCC
                       CCC  TAC  ACC  TGA  CTC  CTG  GGG  TCC  GCA  GGG  GAT  GGG  ACC  CGA  GAG  TCA  CGG
                       Gly  Met  Trp  Thr  Glu  Asp  Pro  Arg  Arg  Pro  Leu  Pro  Trp  Ala  Leu  Ser  Ala>
```

Fig. 1C

```
          1080          1090          1100          1110          1120
            x    x    x    x    x    x    x    x    x    x
          CAC CCC AAG CGC CGA GAG GAA GAT GTA CGT CCC ATC TTC TGG GCC TCC AGA
          GTG GGG TTC GCG GCT CTC CTT CTA CAT GCA GGG TAG AAG ACC CGG AGG TCT
          His Pro Lys Arg Arg Glu Glu Asp Val Arg Pro Ile Phe Trp Ala Ser Arg, 1130          1140          1150          1160          1170
            x    x    x    x    x    x    x    x    x    x
          CCA AAG AGT TAC ATC TAC CGT ACC CAG GAG TGG GAC GAG TTC CCT AAC GGC
          GGT TTC TCA ATG TAG ATG GCA TGG GTC CTC ACC CTG CTC AAG GGA TTG CCG
          Pro Lys Ser Tyr Ile Tyr Arg Thr Gln Glu Trp Asp Glu Phe Pro Asn Gly, 1180          1190          1200          1210          1220
            x    x    x    x    x    x    x    x    x    x
          CGC TGG GGC AAT TCC TCT TCC CCT GCC TTT GGG GAG CTG AAG GAC TAC TAC
          GCG ACC CCG TTA AGG AGA AGG GGA CGG AAA CCC CTC GAC TTC CTG ATG ATG
          Arg Trp Gly Asn Ser Ser Ser Pro Ala Phe Gly Glu Leu Lys Asp Tyr Tyr, 1230          1240          1250          1260          1270
            x    x    x    x    x    x    x    x    x    x
          CTC TTC TAC CTG AAG AGC AAG TCC CCC AAG GAG GAG CTG CTG AAG ATG TGG
          GAG AAG ATG GAC TTC TCG TTC AGG GGG TTC CTC CTC GAC GAC TTC TAC ACC
          Leu Phe Tyr Leu Lys Ser Lys Ser Pro Lys Glu Glu Leu Leu Lys Met Trp, 1280          1290          1300          1310          1320
            x    x    x    x    x    x    x    x    x    x
          GGG GAG GAG CTG ACC AGT GAA GCA AGT GTC TTT GAA GTC TTT GTT CTT TAC
          CCC CTC CTC GAC TGG TCA CTT CGT TCA CAG AAA CTT CAG AAA CAA GAA ATG
          Gly Glu Glu Leu Thr Ser Glu Ala Ser Val Phe Glu Val Phe Val Leu Tyr, 1330          1340          1350          1360          1370
            x    x    x    x    x    x    x    x    x    x
          CTC TCG GGA GAA CCA AAC CGG AAT GGT CAC AAA GTG ACT TGC CTG CCC TGG
          GAG AGC CCT CTT GGT TTG GCC TTA CCA GTG TTT CAC TGA ACG GAC GGG ACC
          Leu Ser Gly Glu Pro Asn Arg Asn Gly His Lys Val Thr Cys Leu Pro Trp, 1380          1390          1400          1410          1420
            x    x    x    x    x    x    x    x    x    x
          AAC GAT GAG CCC CTG GCG GCT GAG ACC AGC CTG CTG AAG GAG GAG CTG CTG
          TTG CTA CTC GGG GAC CGC CGA CTC TGG TCG GAC GAC TTC CTC CTC GAC GAC
          Asn Asp Glu Pro Leu Ala Ala Glu Thr Ser Leu Leu Lys Glu Glu Leu Leu,
```

Fig. 1D

```
        1430          1440          1450          1460          1470
         x    x    x    x    x    x    x    x    x    x
        CGG  GTG  AAC  CGC  CAG  GGC  ATC  CTC  ACC  ATC  AAC  TCA  CAG  CCC  AAC  ATC  AAC
        GCC  CAC  TTG  GCG  GTC  CCG  TAG  GAG  TGG  TAG  TTG  AGT  GTC  GGG  TTG  TAG  TTG
        Arg  Val  Asn  Arg  Gln  Gly  Ile  Leu  Thr  Ile  Asn  Ser  Gln  Pro  Asn  Ile  Asn›

1480          1490          1500          1510          1520          1530
         x    x    x    x    x    x    x    x    x    x    x    x
        GGG  AAG  CCG  TCC  TCC  GAC  CCC  ATC  GTG  GGC  TGG  GGC  CCC  AGC  GGG  GGC  TAT
        CCC  TTC  GGC  AGG  AGG  CTG  GGG  TAG  CAC  CCG  ACC  CCG  GGG  TCG  CCC  CCG  ATA
        Gly  Lys  Pro  Ser  Ser  Asp  Pro  Ile  Val  Gly  Trp  Gly  Pro  Ser  Gly  Gly  Tyr›

1540          1550          1560          1570          1580
                       x    x    x    x    x    x    x    x    x    x    x
                      GTC  TTC  CAG  AAG  GCC  TAC  TTA  GAG  TTT  TTC  ACT  TCC  CGC  GAG  ACA  GCG  GAA
                      CAG  AAG  GTC  TTC  CGG  ATG  AAT  CTC  AAA  AAG  TGA  AGG  GCG  CTC  TGT  CGC  CTT
                      Val  Phe  Gln  Lys  Ala  Tyr  Leu  Glu  Phe  Phe  Thr  Ser  Arg  Glu  Thr  Ala  Glu›

1590          1600          1610          1620          1630
         x    x    x    x    x    x    x    x    x    x
        GCA  CTT  CTG  CAA  GTG  CTG  AAG  AAG  TAC  GAG  CTC  CGG  GTT  AAT  TAC  CAC  CTT
        CGT  GAA  GAC  GTT  CAC  GAC  TTC  TTC  ATG  CTC  GAG  GCC  CAA  TTA  ATG  GTG  GAA
        Ala  Leu  Leu  Gln  Val  Leu  Lys  Lys  Tyr  Glu  Leu  Arg  Val  Asn  Tyr  His  Leu›

1640          1650          1660          1670          1680
         x    x    x    x    x    x    x    x    x    x
        GTC  AAT  GTG  AAG  GGT  GAA  AAC  ATC  ACC  AAT  GCC  CCT  GAA  CTG  CAG  CCG  AAT
        CAG  TTA  CAC  TTC  CCA  CTT  TTG  TAG  TGG  TTA  CGG  GGA  CTT  GAC  GTC  GGC  TTA
        Val  Asn  Val  Lys  Gly  Glu  Asn  Ile  Thr  Asn  Ala  Pro  Glu  Leu  Gln  Pro  Asn›

1690          1700          1710          1720          1730
         x    x    x    x    x    x    x    x    x    x
        GCT  GTC  ACT  TGG  GGC  ATC  TTC  CCT  GGG  CGA  GAG  ATC  ATC  CAG  CCC  ACC  GTA
        CGA  CAG  TGA  ACC  CCG  TAG  AAG  GGA  CCC  GCT  CTC  TAG  TAG  GTC  GGG  TGG  CAT
        Ala  Val  Thr  Trp  Gly  Ile  Phe  Pro  Gly  Arg  Glu  Ile  Ile  Gln  Pro  Thr  Val›

1740          1750          1760          1770          1780
         x    x    x    x    x    x    x    x    x    x
        GTG  GAT  CCC  GTC  AGC  TTC  ATG  TTC  TGG  AAG  GAC  GAG  GCC  TTT  GCC  CTG  TGG
        CAC  CTA  GGG  CAG  TCG  AAG  TAC  AAG  ACC  TTC  CTG  CTC  CGG  AAA  CGG  GAC  ACC
        Val  Asp  Pro  Val  Ser  Phe  Met  Phe  Trp  Lys  Asp  Glu  Ala  Phe  Ala  Leu  Trp›
```

Fig. 1E

```
        1790       1800       1810       1820       1830
          :    :    :    :    :    :    :    :    :    :
        ATT GAG CGG TGG GGA AAG CTG TAT GAG GAG GAG TCC CCG TCC CGC ACC ATC
        TAA CTC GCC ACC CCT TTC GAC ATA CTC CTC CTC AGG GGC AGG GCG TGG TAG
        Ile Glu Arg Trp Gly Lys Leu Tyr Glu Glu Glu Ser Pro Ser Arg Thr Ile›

1840       1850       1860       1870       1880
          :    :    :    :    :    :    :    :    :    :
        ATC CAG TAC ATC CAC GAC AAC TAC TTC CTG GTC AAC CTG GTG GAC AAT GAC
        TAG GTC ATG TAG GTG CTG TTG ATG AAG GAC CAG TTG GAC CAC CTG TTA CTG
        Ile Gln Tyr Ile His Asp Asn Tyr Phe Leu Val Asn Leu Val Asp Asn Asp›

1890       1900       1910       1920       1930
         :    :    :    :    :    :    :    :    :    :
       TTC CCA CTG GAC AAC TGC CTC TGG CAG GTG GTG GAA GAC ACA TTG GAG CTT
       AAG GGT GAC CTG TTG ACG GAG ACC GTC CAC CAC CTT CTG TGT AAC CTC GAA
       Phe Pro Leu Asp Asn Cys Leu Trp Gln Val Val Glu Asp Thr Leu Glu Leu›

1940       1950       1960       1970       1980       1990
         :    :    :    :    :    :    :    :    :    :    :    :
       CTC AAC AGG CCC ACC CAG AAT GCG AGA GAA ACG GAG GCT CCA TGACCCTGCG
       GAG TTG TCC GGG TGG GTC TTA CGC TCT CTT TGC CTC CGA GGT ACTGGGACGC
       Leu Asn Arg Pro Thr Gln Asn Ala Arg Glu Thr Glu Ala Pro›

2000       2010       2020       2030       2040       2050
            :    :    :    :    :    :    :    :    :    :    :    :
         TCCTGACGCC CTGCGTTGGA GCCACTCCTG TCCCGCCTTC CTCCTCCACA GTGCTGCTTC
         AGGACTGCGG GACGCAACCT CGGTGAGGAC AGGGCGGAAG GAGGAGGTGT CACGACGAAG 2060       2070       2080       2090       2100       2110
            :    :    :    :    :    :    :    :    :    :    :    :
         TCTTGGGAAC TCCACTCTCC TTCGTGTCTC TCCCACCCCG GCCTCCACTC CCCCACCTGA
         AGAACCCTTG AGGTGAGAGG AAGCACAGAG AGGGTGGGGC CGGAGGTGAG GGGGTGGACT 2120       2130       2140       2150       2160       2170
            :    :    :    :    :    :    :    :    :    :    :    :
         CAATGGCAGC TAGACTGGAG TGAGGCTTCC AGGCTCTTCC TGGACCTGAG TCGGCCCCAC
         GTTACCGTCG ATCTGACCTC ACTCCGAAGG TCCGAGAAGG ACCTGGACTC AGCCGGGGTG 2180       2190       2200       2210       2220
            :    :    :    :    :    :    :    :    :
         ATGGGAACCT AGTACTCTCT GCTCTAAAAA AAAAAAAAAA AAAGGAATTC
         TACCCTTGGA TCATGAGAGA CGAGATTTTT TTTTTTTTTT TTTCCTTAAG
```

Fig. 1F

```
AMVNE ARGNS SLNPC LEGSA SSGSE SSKDS SRCST PGLDP ERHER LREKM RRRLE S--GDKW FSLEF  mthfr
                                                ms fFHas qRdal nqsLa evqGqin vSFEF  ecometf
                                                ms fFHan qREal nqsLa evqGqin vSFEF  stymetf
                                                   ms iRdLy haraspf iSLEF          ysRADI
                                            100·
FPPRT AEGAV NLISR FDRMA AGGPL YIDVT WHPAG DPGSD KETSS MMIAS TAVNY CGLET ILHMT    mthfr
FPPRT sEmeq tLwns iDRIs sikPk fvsVT y--ga nsGer drIhs i-lkg ik-dr tGLEa apHIT     ecometf
FPPRT sEmeq tLwns iDRIs sikPk fvsVT y--ga nsGer drIhs v-lkg ik-er tGLEa apHIT    stymetf
FPPkT eIGtr NLmeR mhRMt AldPL fItVT W--ga -gGtt aEktl t-IAS lAqqt lnipv cmHIT    ysRADI
                                                            *
CCRQR LEEIT GHLHK AKQLG LKNIM ALRGD -PIGDQ WEEEE GGFNY AVGLV KHIRS EFGDY FDICV    mthfr
Cidat pdEIr tiard ywnnG irhIv ALRGD lPpGsg kpE-- ---mY AsdLV tllk- EvaD- FDIsV    ecometf
Cidat rdEIr tiard ywnnG irhIv ALRGD lPpGsg kpE-- ---mY AadLV gllk- EvaD- FDIsV    stymetf
Ctnte kaild daLdr cynaG irNlI ALRGn lPIGvv Wlvsq snrrl nmrLf)                     ysRADI
   200·
AGYPK GHPEA GSFEA DLKHL KEKVS AGADF IITQL FFEAD TEFRF VKACT DMGIT CPIVP GIFPI    mthfr
AaYPe vHPEA KSaqA DLinL KrKVd AGAnr aITQF FFdve syIRF rdrCv saGId veIiP GIIPv    ecometf
AaYPe vHPEA KSaqA DLinL KrKVd AGAnr aITQF FFdve syIRF rdrCv saGId veIiP GIIPv    stymetf
                                        300·
QGYHS LRQLV KLSKL EVPQE IKDVI EPIKD NDAAI RN-YGI ELAVS LCQEL LASGL VPGLH FYTLN   mthfr
snfkq akkfa dmtnv riPaw maqmf dgl-D dDAet RklvGa niAmd mvkil sreG- VkdfH FYTLN    ecometf
snfkq akkfa dmtnv riPsw mslmf Egl-D nDAet RklvGa niAmd mvkil sreG- VkdfH FYTLN   stymetf
R-EMAT TEVLK RLGMW TEDPR RPLPW ALSAH PKRRE EDVRP IFWAS RPKSY IYRID EWDEF PNGRW   mthfr
RaEMsy a-ich tLGvr pgl>                                                           ecometf
RaEMsy a-ich tLGvr pgl>                                                           stymetf
      400·
GNSSS PAFGE LKDYY LFYLK SKSPK E  mthfr
```

Fig. 2

```
AAT TCC GGA GCC ATG GTG AAC GAA GCC AGA GGA AAC AGC AGC CTC AAC CCC TGC TTG GAG   60
                Met Val Asn Glu Ala Arg Gly Asn Ser Ser Leu Asn Pro Cys Leu Glu   16

GGC AGT GCC AGC AGT GGC AGT GAG AGC TCC AAA GAT AGT TCG AGA TGT TCC ACC CCG GGC  120
Gly Ser Ala Ser Ser Gly Ser Glu Ser Ser Lys Asp Ser Ser Arg Cys Ser Thr Pro Gly   36

CTG GAC CCT GAG CGG CAT GAG AGA CTC CGG GAG AAG ATG AGG CGG CGA TTG GAA TCT GGT  180
Leu Asp Pro Glu Arg His Glu Arg Leu Arg Glu Lys Met Arg Arg Arg Leu Glu Ser Gly   56

GAC AAG TGG TTC TCC CTG GAA TTC TTC CCT CCT CGA ACT GCT GAG GGA GCT GTC AAT CTC  240
Asp Lys Trp Phe Ser Leu Glu Phe Phe Pro Pro Arg Thr Ala Glu Gly Ala Val Asn Leu   76

ATC TCA AGG TTT GAC CGG ATG GCA GCA GGT GGC CCC CTC TAC ATA GAC GTG ACC TGG CAC  300
Ile Ser Arg Phe Asp Arg Met Ala Ala Gly Gly Pro Leu Tyr Ile Asp Val Thr Trp His   96

CCA GCA GGT GAC CCT GGC TCA GAC AAG GAG ACC TCC TCC ATG ATG ATC GCC AGC ACC GCC  360
Pro Ala Gly Asp Pro Gly Ser Asp Lys Glu Thr Ser Ser Met Met Ile Ala Ser Thr Ala  116

GTG AAC TAC TGT GGC CTG GAG ACC ATC CTG CAC ATG ACC TGC TGC CGT CAG CGC CTG GAG  420
Val Asn Tyr Cys Gly Leu Glu Thr Ile Leu His Met Thr Cys Cys Arg Gln Arg Leu Glu  136

GAG ATC ACG GGC CAT CTG CAC AAA GCT AAG CAG CTG GGC CTG AAG AAC ATC ATG GCG CTG  480
Glu Ile Thr Gly His Leu His Lys Ala Lys Gln Leu Gly Leu Lys Asn Ile Met Ala Leu  156

CGG GGA GAC CCA ATA GGT GAC CAG TGG GAA GAG GAG GAG GGA GGC TTC AAC TAC GCA GTG  540
Arg Gly Asp Pro Ile Gly Asp Gln Trp Glu Glu Glu Glu Gly Gly Phe Asn Tyr Ala Val  176

GAC CTG GTG AAG CAC ATC CGA AGT GAG TTT GGT GAC TAC TTT GAC ATC TGT GTG GCA GGT  600
Asp Leu Val Lys His Ile Arg Ser Glu Phe Gly Asp Tyr Phe Asp Ile Cys Val Ala Gly  196

TAC CCC AAA GGC CAC CCC GAA GCA GGG AGC TTT GAG GCT GAC CTG AAG CAC TTG AAG GAG  660
Tyr Pro Lys Gly His Pro Glu Ala Gly Ser Phe Glu Ala Asp Leu Lys His Leu Lys Glu  216

AAG GTG TCT GCG GGA GCC GAT TTC ATC ATC ACG CAG CTT TTC TTT GAG GCT GAC ACA TTC  720
Lys Val Ser Ala Gly Ala Asp Phe Ile Ile Thr Gln Leu Phe Phe Glu Ala Asp Thr Phe  236
```

Fig. 6A

```
TTC CGC TTT GTG AAG GCA TGC ACC GAC ATG GGC ATC ACT TGC CCC ATC GTC CCC GGG ATC  780
Phe Arg Phe Val Lys Ala Cys Thr Asp Met Gly Ile Thr Cys Pro Ile Val Pro Gly Ile  256

TTT CCC ATC CAG GGC TAC CAC TCC CTT CGG CAG CTT GTG AAG CTG TCC AAG CTG GAG GTG  840
Phe Pro Ile Gln Gly Tyr His Ser Leu Arg Gln Leu Val Lys Leu Ser Lys Leu Glu Val  276

CCA CAG GAG ATC AAG GAC GTG ATT GAG CCA ATC AAA GAC AAC GAT GCT GCC ATC CGC AAC  900
Pro Gln Glu Ile Lys Asp Val Ile Glu Pro Ile Lys Asp Asn Asp Ala Ala Ile Arg Asn  296

TAT GGC ATC GAG CTG GCC GTG AGC CTG TGC CAG GAG CTT CTG GCC AGT GGC TTG GTG CCA  960
Tyr Gly Ile Glu Leu Ala Val Ser Leu Cys Gln Glu Leu Leu Ala Ser Gly Leu Val Pro  316

GGC CTC CAC TTC TAC ACC CTC AAC CGC GAG ATG GCT ACC ACA GAG GTG CTG AAG CGC CTG 1020
Gly Leu His Phe Tyr Thr Leu Asn Arg Glu Met Ala Thr Thr Glu Val Leu Lys Arg Leu  336

GGG ATG TGG ACT GAG GAC CCC AGG CGT CCC CTA CCC TGG GCT CTC AGT GCC CAC CCC AAG 1080
Gly Met Trp Thr Glu Asp Pro Arg Arg Pro Leu Pro Trp Ala Leu Ser Ala His Pro Lys  356

CGC CGA GAG GAA GAT GTA CGT CCC ATC TTC TGG GCC TCC AGA CCA AAG AGT TAC ATC TAC 1140
Arg Arg Glu Glu Asp Val Arg Pro Ile Phe Trp Ala Ser Arg Pro Lys Ser Tyr Ile Tyr  376

CGT ACC CAG GAG TGG GAC GAG TTC CCT AAC GGC CGC TGG GGC AAT TCC TCT TCC CCT GCC 1200
Arg Thr Gln Glu Trp Asp Glu Phe Pro Asn Gly Arg Trp Gly Asn Ser Ser Ser Pro Ala  396

TTT GGG GAG CTG AAG GAC TAC TAC CTC TTC TAC CTG AAG AGC AAG TCC CCC AAG GAG GAG 1260
Phe Gly Glu Leu Lys Asp Tyr Tyr Leu Phe Tyr Leu Lys Ser Lys Ser Pro Lys Glu Glu  416

CTG CTG AAG ATG TGG GGG GAG GAG CTG ACC AGT GAA GCA AGT GTC TTT GAA GTC TTT GTT 1320
Leu Leu Lys Met Trp Gly Glu Glu Leu Thr Ser Glu Ala Ser Val Phe Glu Val Phe Val  436

CTT TAC CTC TCG GGA GAA CCA AAC CGG AAT GGT CAC AAA GTG ACT TGC CTG CCC TGG AAC 1380
Leu Tyr Leu Ser Gly Glu Pro Asn Arg Asn Gly His Lys Val Thr Cys Leu Pro Trp Asn  456

GAT GAG CCC CTG GCG GCT GAG ACC AGC CTG CTG AAG GAG GAG CTG CTG CGG GTG AAC CGC 1440
Asp Glu Pro Leu Ala Ala Glu Thr Ser Leu Leu Lys Glu Glu Leu Leu Arg Val Asn Arg  476
```

Fig. 6B

```
CAG GGC ATC CTC ACC ATC AAC TCA CAG CCC AAC ATC AAC GGG AAG CCG TCC TCC GAC CCC 1500
Gln Gly Ile Leu Thr Ile Asn Ser Gln Pro Asn Ile Asn Gly Lys Pro Ser Ser Asp Pro  496

ATC GTG GGC TGG GGC CCC AGC GGG GGC TAT GTC TTC CAG AAG GCC TAC TTA GAG TTT TTC 1560
Ile Val Gly Trp Gly Pro Ser Gly Gly Tyr Val Phe Gln Lys Ala Tyr Leu Glu Phe Phe  516

ACT TCC CGC GAG ACA GCG GAA GCA CTT CTG CAA GTG CTG AAG AAG TAC GAG CTC CGG GTT 1620
Thr Ser Arg Glu Thr Ala Glu Ala Leu Leu Gln Val Leu Lys Lys Tyr Glu Leu Arg Val  536

AAT TAC CAC CTT GTC AAT GTG AAG GGT GAA AAC ATC ACC AAT GCC CCT GAA CTG CAG CCG 1680
Asn Tyr His Leu Val Asn Val Lys Gly Glu Asn Ile Thr Asn Ala Pro Glu Leu Gln Pro  556

AAT GCT GTC ACT TGG GGC ATC TTC CCT GGG CGA GAG ATC ATC CAG CCC ACC GTA GTG GAT 1740
Asn Ala Val Thr Trp Gly Ile Phe Pro Gly Arg Glu Ile Ile Gln Pro Thr Val Val Asp  576

CCC GTC AGC TTC ATG TTC TGG AAG GAC GAG GCC TTT GCC CTG TGG ATT GAG CGG TGG GGA 1800
Pro Val Ser Phe Met Phe Trp Lys Asp Glu Ala Phe Ala Leu Trp Ile Glu Arg Trp Gly  596

AAG CTG TAT GAG GAG GAG TCC CCG TCC CGC ACC ATC ATC CAG TAC ATC CAC GAC AAC TAC 1860
Lys Leu Tyr Glu Glu Glu Ser Pro Ser Arg Thr Ile Ile Gln Tyr Ile His Asp Asn Tyr  616

TTC CTG GTC AAC CTG GTG GAC AAT GAC TTC CCA CTG GAC AAC TGC CTC TGG CAG GTG GTG 1920
Phe Leu Val Asn Leu Val Asp Asn Asp Phe Pro Leu Asp Asn Cys Leu Trp Gln Val Val  636

GAA GAC ACA TTG GAG CTT CTC AAC AGG CCC ACC CAG AAT GCG AGA GAA ACG GAG GCT CCA 1980
Glu Asp Thr Leu Glu Leu Leu Asn Arg Pro Thr Gln Asn Ala Arg Glu Thr Glu Ala Pro  656

TGA CCC TGC GTC CTG ACG CCC TGC GTT GGA GCC ACT CCT GTC CCG CCT TCC TCC TCC ACA 2040
End

GTG CTG CTT CTC TTG GGA ACT CCA CTC TCC TTC GTG TCT CTC CCA CCC CGG CCT CCA CTC 2100

CCC CAC CTG ACA ATG GCA GCT AGA CTG GAG TGA GGC TTC CAG GCT CTT CCT GGA CCT GAG 2160

TCG GCC CCA CAT GGG AAC CTA GTA CTC TCT GCT CTA AAA AAA AAA AAA AAA AAG GAA TT  2220
```

Fig. 6C

```
MTHFR:    KHLKEKVSAGADFIITQLFFEADTFFR
          ||| |·       | |  ||·||||
DHFR:     GHLKLFVT----R-IMQD-FESDTFFP
```

EXON 1: 246 bp          (bp 3-248)
                                                                    *
gggtgtggct gcctgccccc tgatgctccc tgccccaccc tgtgcagtag GAACCCAGCC
ATGGTGAACG AAGCCAGAGG AAACAGCAGC CTCAACCCCT GCTTGGAGGG CAGTGCCAGC
AGTGGCAGTG AGAGCTCCAA AGATAGTTCG AGATGTTCCA CCCCGGGCCT GGACCCTGAG
CGGCATGAGA GACTCCGGGA GAAGATGAGG CGGCGATTGG AATCTGGTGA CAAGTGGTTC
TCCCTGGAAT TCTTCCCTCC TCGAACTGCT GAGGGAGCTG TCAATCTCAT CTCAAGgtaa
actcatgcaa ggttaaggtg agaggcggga gtggtggtgc ctgggg EXON 2: 239 bp          (bp 249-487)

acggatgg tatttctcct ggaacctctc ttcagaaaca aacccctacag GTTTGACCGG
ATGGCAGCAG GTGGCCCCCT CTACATAGAC GTGACCTGGC ACCCAGCAGG TGACCCTGGC
TCAGACAAGG AGACCTCCTC CATGATGATC GCCAGCACCG CCGTGAACTA CTGTGGCCTG
GAGACCATCC TGCACATGAC CTGCTGCCGT CAGCGCCTGG AGGAGATCAC GGGCCATCTG
CACAAAGCTA AGCAGCTGGG CCTGAAGAAC ATCATGGCGC TGCGGGGAGg tgtggagcca
gcactcccct acactctggg ttctggcttt cccggaggc EXON 3: 111 bp          (bp 488-598)

tctggaggtt gggtgagacc cagtgactat gacctccacc aaccctgcag ACCCAATAGG
TGACCAGTGG GAAGAGGAGG AGGGAGGCTT CAACTACGCA GTGGACCTGG TGAAGCACAT
CCGAAGTGAG TTTGGTGACT ACTTTGACAT CTGTGTGGCA Ggtgagtggc tggatcatcc
tggtggcggg gatggagcta gggaggctga EXON 4: 194 bp          (bp 599-792)
ccttgaacag gtggaggcca gcctctcctg actgtcatcc ctattggcag GTTACCCCAA
AGGCCACCCC GAAGCAGGGA GCTTTGAGGC TGACCTGAAG CACTTGAAGG AGAAGGTGTC
TGCGGGAGCC GATTTCATCA TCACGCAGCT TTTCTTTGAG GCTGACACAT TCTTCCGCTT
TGTGAAGGCA TGCACCGACA TGGGCATCAC TTGCCCCATC GTCCCCGGGA TCTTTCCCAT
CCAGgtgagg ggcccaggag agcccataag ctccctccac ccactctca ccgc EXON 5: 251 bp          (bp 793-1043)

gctggccagc agccgccaca gcccctcatg tcttggacag GGCTACCACT CCCTTCGGCA
GCTTGTGAAG CTGTCCAAGC TGGAGGTGCC ACAGGAGATC AAGGACGTGA TTGAGCCAAT
CAAAGACAAC GATGCTGCCA TCCGCAACTA TGGCATCGAG CTGGCCGTGA GCCTGTGCCA
GGAGCTTCTG GCCAGTGGCT TGGTGCCAGG CCTCCACTTC TACACCCTCA ACCGCGAGAT
GGCTACCACA GAGGTGCTGA AGCGCCTGGG GATGTGGACT GAGGACCCCA Ggtgagggca
gtgcccaga gatccccaga ggagggtcca agagcagccc c EXON 6: 135 bp          (bp 1044-1178)

tccctctagc caatcccttg tctcaattct ctgtccccat cctcacccag GCGTCCCCTA
CCCTGGGCTC TCAGTGCCCA CCCCAAGCGC CGAGAGGAAG ATGTACGTCC CATCTTCTGG
GCCTCCAGAC CAAAGAGTTA CATCTACCGT ACCCAGGAGT GGGACGAGTT CCCTAACGGC
CGCTGgtgag ggcctgcaga ccttccttgc aaatacatct ttgttcttgg gagcg

Fig.12A

EXON 7: 181 bp           (bp 1179-1359)

actgccctct gtcaggagtg tgccctgacc tctgggcacc cctctgccag GGGCAATTCC
TCTTCCCCTG CCTTTGGGGA GCTGAAGGAC TACTACCTCT TCTACCTGAA GAGCAAGTCC
CCCAAGGAGG AGCTGCTGAA GATGTGGGGG GAGGAGCTGA CCAGTGAAGC AAGTGTCTTT
GAAGTCTTTG TTCTTTACCT CTCGGGAGAA CCAAACCGGA ATGGTCACAA Agtgagtgat
gctggaagtg gggaccctgg ttcatcccct gccctggcc t EXON 8: 183 bp           (bp 1360-1542)

cagggtgcca aacctgatgg tcgccccagc cagctcaccg tctctcccag GTGACTTGCC
TGCCCTGGAA CGATGAGCCC CTGGCGGCTG AGACCAGCCT GCTGAAGGAG GAGCTGCTGC
GGGTGAACCG CCAGGGCATC CTCACCATCA ACTCACAGCC CAACATCAAC GGGAAGCCGT
CCTCCGACCC CATCGTGGGC TGGGGCCCCA GCGGGGGCTA TGTCTTCCAG AAGgtgtggt
agggaggcac ggggtgcccc cctctcttga ccggcacccg tgg EXON 9: 102 bp           (bp 1543-1644)

gggcgtctgg cagggctggg gttggtgaca ggcacctgtc tctcccacag GCCTACTTAG
AGTTTTTCAC TTCCCGCGAG ACAGCGGAAG CACTTCTGCA AGTGCTGAAG AAGTACGAGC
TCCGGGTTAA TTACCACCTT GTCAATGTGA AGgtaggcca ggccccacgg ttcccacaga
gtaccaggcc cttcgttgaa ca EXON 10: 120 bp           (bp 1645-1764)

actccagttg ttcttggccc aggtcttacc cccacccac atccctcag GGTGAAAACA
TCACCAATGC CCCTGAACTG CAGCCGAATG CTGTCACTTG GGGCATCTTC CCTGGGCGAG
AGATCATCCA GCCCACCGTA GTGGATCCCG TCAGCTTCAT GTTCTGGAAG gtaaaggagc
ggggcaagc ttgccccgcc cacctggaaa accgtgggga EXON 11: 219 bp (stop codon)   (bp 1765-1983)
        432 bp (end of cDNA)   (bp 1765-2196)

ctctgtgtgt gtgtgcatgt gtgcgtgtgt gcggggtat gtgtgtgtag GACGAGGCCT
TTGCCCTGTG GATTGAGCGG TGGGAAAAGC TGTATGAGGA GGAGTCCCCG TCCCGCACCA
TCATCCAGTA CATCCACGAC AACTACTTCC TGGTCAACCT GGTGGACAAT GACTTCCCAC
TGGACAACTG CCTCTGGCAG GTGGTGGAAG ACACATTGGA GCTTCTCAAC AGGCCCACCC
AGAATGCGAG AGAAACGGAG GCTCCATGAC CCTGCGTCCT GACGCCCTGC GTTGGAGCCA
CTCCTGTCCC GCCTTCCTCC TCCACAGTGC TGCTTCTCTT GGGAACTCCA CTCTCCTTCG
TGTCTCTCCC ACCCCGGCCT CCACTCCCCC ACCTGACAAT GGCAGCTAGA CTGGAGTGAG
GCTTCCAGGC TCTTCCTGGA CCTGAGTCGG CCCCACATGG GAACCTAGTA CTCTCTGCTC
TAgccaggag tctgtgctct tttggtgggg agcacttgct cctgcagagg ac

Fig. 12B

EXON 1: 243 bp        (bp 3-245)
                                                                  *
gggtttggta ccagccctat aataccccg gcccccaccc tctacagcag **GAATCCAGCC
ATGGTGAACG AGGCCAGAGG AAGTGGCAGT CCCAACCCGC GATCTGAGGG CAGCAGCAGT
GGCAGCGAGA GTTCCAAGGA CAGTTCAAGA TGTTCCACCC CCAGCCTGGA CCCAGAGCGG
CACGAGAGAC TCCGGGAGAA GATGAGGCGC AGAATGGACT CTGGTGACAA GTGGTTCTCC
CTGGAGTTCT TCCCCCCTCG AACTGCTGAG GGAGCTGTTA ACCTCATCTC CAG**gtgagta
gggaggttaa tccgcggggg tcggcaggct tcaggggagc gtg EXON 2: 239 bp        (bp 246-484)

gagctcccta tttaccccag gagcctactt aaggaggaaa tcccctacag **GTTTGACCGG
ATGGCAGCAG GGGGCCCCCT CTTCGTAGAT GTTACCTGGC ACCCAGCTGG AGACCCTGGC
TCAGACAAGG AGACCTCCTC CATGATGATC GCCAGCACAG CAGTAAACTA CTGCGGCTTG
GAAACCATCC TGCATATGAC CTGCTGCCAG CAGCGCCCGG AGGAGATCAC AGGCCATCTG
CACAGAGCCA AGCAGCTGGG CCTGAAGAAC ATAATGGCGC TGAGGGGAG**g tgtggcgcca
gcacccctcc tctttgggtt cttgctttcc tgaaggctt EXON 3: 111 bp        (bp 485-595)

tctggaggtc aggggacacc cagtgaccat gacctccagc aaccctgcag **ACCCTGTAGG
TGACCACTGG GAAGCAGAGG AAGGAGGCTT CAGCTATGCC ACAGACCTGG TGAAGCACAT
CCGGACCGAG TTTGCTGACT ATTTTGACAT CTGTGTGGCA G**gtaagtgag gacagagaag
ggtcaggatg agaggatagc cagctagtct t EXON 4: 194 bp        (bp 596-789)

gcaggtaggt tgagaccagc cccctactc ttcttgtctc ctcctggtag **GTTACCCCAG
AGGCCACCCC GATGCAGAGA GCTTCGAGGA TGACCTGAAG CATTTGAAGG AGAAGGTATC
TGCAGGCGCC GACTTCATTA TCACTCAGCT CTTCTTTGAG GCCAGCACCT TCTTCAGCTT
TGTGAAGGCC TGCACAGAGA TAGGCATCTC TTGCCCTATC CTGCCTGGGA TCTTCCCTAT
TCAG**gtgagg ggcttgggag gacctgattc cctccgtcca gtgcatgcgg aagt EXON 5: 251 bp        (bp 790-1040)

cagtggagca taggccagag atgacccat gccccttgtg tctctgacag **GGCTACACTT
CCCTTCGGCA GCTTGTAAAA CTGTCCAAGC TGGAGGTGCC ACAGAAGATC AAGGATGTAA
TTGAGCCCAT CAAAGACAAC GATGCTGCCA TCCGCAACTA CGGCATTGAG CTGGCTGTAA
GGCTGTGCCG GGAGCTGCTG GACAGTGGCT TGGTGCCAGG CCTCCACTTC TATACCCTCA
ACCGCGAGGT GGCCACCATG GAGGTGCTAA AGCAACTGGG CATGTGGACC GAGGACCCCA
G**gtgagcggt ggaagctgga ggcataccca tgagtcagag tcgcgcaggt g EXON 6: 135 bp        (bp 1041-1175)

ctagctcagt ctacctaagc ccttgtcttt tcctcttcc ttccctccag **GCGTCCCTTG
CCCTGGGCTC TCAGTGCGCA TCCCAAGCGC CGGGAGGAAG ATGTCCGTCC CATCTTCTGG
GCCTCCAGAC CAAAGAGCTA CATCTACCGC ACACAGGACT GGGATGAGTT TCCTAACGGC
CGCTG**gtgag gagagaagcc aggggggtgtt aggaattgct ggtgcctggg tggaa

Fig.13A

EXON 7: 181 bp        (bp 1176-1356)

aataggacaa gatttacaac aaagtgcctt gtcccttata ctcctgccag **GGGTAATTCT
TCCTCACCAG CCTTTGGGGA GCTGAAAGAC TACTACCTCT TCTACCTGAA AAGCAAGTCC
CCCAGGGAGG AGCTGCTGAA GATGTGGGGC GAGGAGCTCA CCAGCGAAGA GAGTGTCTTT
GAAGTCTTTG AACACTACCT CTCTGGAGAG CCGAATCGCC ATGGCTACAG** A<u>gt</u>gagtggg
gtgaggagga acggcccagc tttgtctcag ccttgg EXON 8: 183 bp        (bp 1357-1539)

cccagtccca gactcagtgc tgccctcgct cagcgcaccc tgccctgc<u>ag</u> **GTAACCTGCC
TGCCCTGGAA CGATGAACCC CTGGCAGCGG AAACCAGCCT GATGAAGGAA GAGCTGCTCC
GCGTGAACAG GCTGGGCATC CTCACCATCA ACTCTCAGCC CAACATCAAC GCAAAACCAT
CCTCAGACCC TGTTGTGGGC TGGGGCCCCA GTGGGGGTTA TGTCTTCCAG AAG**<u>gt</u>atgct
aggatgcagt actctcgata tccccaggga ctgacacaga acc EXON 9: 102 bp        (bp 1540-1641)

gagaacttgg caagtagtgg ggttgacatg ttgggtgtat tctccctc<u>ag</u> **GCCTACCTCG
AATTCTTCAC CTCCCGTGAA ACTGTGGAGG CGCTTCTGCA GGTGCTGAAG ACATACGAGC
TGCGGGTCAA CTACCACATC GTGGACGTGA AG**<u>gt</u>aagcca gctccctccg gcttagacgc
agcaaggctt gaaaacacct aca EXON 10: 120 bp       (bp 1642-1761)

agcagtggga ggttgcggtc accctgcctc agccctgcct ctgttctc<u>ag</u> **GGAGAGAACA
TCACTAATGC CCCTGAGCTG CAGCCCAATG CCGTGACGTG GGGCATCTTC CCGGGTCGAG
AGATCATCCA GCCTACTGTG GTGGACCCCA TCAGCTTCAT GTTCTGGAAG** <u>gt</u>aagggagt
gggagggagt ggaggaccct ggctaccgtg agagcccag EXON 11: 216 bp (stop codon)   (bp 1762-1977)

ggaggtacca gccgtgctga ccctgctcgt gtgtctctgt tcacacgt<u>ag</u> **GATGAGGCCT
TTGCCCTGTG GATCGAGCAG TGGGGCAAGC TATACGAGGA GGAGTCGCCA TCCCGCATGA
TCATCCAATA CATCCATGAC AACTATTTCC TGGTCAACCT GGTGGACAAC GAGTTCCCGC
TGGACAGCTG CCTGTGGCAG GTGGTGGAGG ACACGTTTGA GCTGCTCAAC AGGCATCCCA
CGGAGAGAGA GACACAGGCT CCATGA**gcct gcatctctca acaggcacac catggagaga
gagacacagg ctctgtgagc cgtgcatccc tcaacaggca caccacggag agagagacac
aggctccgtg agcctgcatc ccggtatctt cctcacctgg agccctctc cctcatctct
ctacaca

Fig.13B

```
hMTHFR  MVNEARGNSSLNPCLEGSASSGSESSKDSSRCSTPGLDPERHERLREKMRRRLESGDKWF
mMTHFR  □□□□□□□sg□ps□rs□□□-□□□□□□□□□□□□□□□□s□□□□□□□□□□□□□□□□mds□□□□□
bMTHFR  ---------------------------------fhasqrda□nqsl-aevq-□qinv hMTHFR  SLEFFPPRTAEGAVNLISRFDRMAAGGPLYIDVTWHPAGDPGSDKETSSMMIASTAVNYC
mMTHFR  □□□□□□□□□□□□□□□□□□□□□□□□□□□□□□□□fv□□□□□□□□□□□□□□□□□□□□□□□□□
bMTHFR  □f□□□□□□□□s□meqt□wnsi□□lsslk□kfvs□□-yg□-ns□erdr□h□--□kgik-drt hMTHFR  GLETILHMTCCRQRLEEITGHLHKAKQLGLKNIMALRGDPIGDQWEEEEGGFNYAVDLVK
mMTHFR  □□□□□□d□□□□q□□p□□□□□□□□□r□□□□□□□□□□□□□□□□v□□h□□a□□□□□s□□t□□□□
bMTHFR  □□□aap□l□□idatpd□lrtiardywnn□irh□v□□□□□□lpp-gsgkp□m---□□s□□□t hMTHFR  HIRSEFGDYFDICVAGYPKGHPEAGSFEADLKHLKEKVSAGADFIITQLFFEADTFFRFV
mMTHFR  □□□t□□a□□□□□□□□□□□r□□□d□e□□□d□□□□□□□□□□□□□□□□□□□□□□□□□s□□□s□□
bMTHFR  llk-□va□-□□□s□□a□□ev□□□□k□aq□□□ln□□r□□d□□□nra□□□f□□dvesyl□□r hMTHFR  KACTDMGITCPIVPGIFPIQGYHSLRQLVKLSKLEVPQEIKDVIEPIKDNDAAIRNYGIE
mMTHFR  □□□□ei□□s□□□l□□□□□□□□□t□□□□□□□□□□□□□□□k□□□□□□□□□□□□□□□□□□□□□
bMTHFR  dr□vsa□□dve□i□□□l□vsnfkqakkfadmtnvri□awmaqmfdgld□daetrklv□an hMTHFR  LAVSLCQELLASGLVPGLHFYTLNREMATTEVLKRLGMWTEDPRRPLPWALSAHPKRREE
mMTHFR  □□□x□□r□□□ds□□□□□□□□□□□□□□□□v□□m□□□□q□□□□□□□□□□□□□□□□□□□□□□□
bMTHFR  i□mdmvk-i□sreg□kdf□□□□□□□aemsyaicht□□vr-------------------- hMTHFR  DVRPIFWASRPKSYIYRTQEWDEFPNGRWGNSSSPAFGELKDYYLFYLKSKSPKEELLKM
mMTHFR  □□□□□□□□□□□□□□□□□□d□□□□□□□□□□□□□□□□□□□□□□□□□□□□□□□□□□□r□□□□□□
bMTHFR  ------------------------------------------------------------ hMTHFR  WGEELTSEASVFEVFVLYLSGEPNRNGHKVTCLPWNDEPLAAETSLLKEELLRVNRQGIL
mMTHFR  □□□□□□□□e□□□□□□eh□□□□□□□□□h□yr□□□□□□□□□□□□□□□□□m□□□□□□□□□l□□□
bMTHFR  ------------------------------------------------------------ hMTHFR  TINSQPNINGKPSSDPIVWGPSGGYVFQKAYLEFFTSRETAEALLQVLKKYELRVNYHL
mMTHFR  □□□□□□□□□a□□□□□□v□□□□□□□□□□□□□□□□□□□□□□□□□□□v□□□□□□□□t□□□□□□□□i
bMTHFR  ----------------------------------------------------------- hMTHFR  VNVKGENITNAPELQPNAVTWGIFPGREIIQPTVVDPVSFMFWKDEAFALWIERWGKLYE
mMTHFR  □d□□□□□□□□□□□□□□□□□□□□□□□□□□□□□□□□□□□□□□□i□□□□□□□□□□□□□□q□□□□□□
bMTHFR  ------------------------------------------------------------ hMTHFR  EESPSRTIIQYIHDNYFLVNLVDNDFPLDNCLWQVVEDTLELLNRPTQNARETEAP
mMTHFR  □□□□□□m□□□□□□□□□□□□□□□□□□□e□□□□s□□□□□□□□□□f□□□□□h-pte□□□q□□
bMTHFR  -------------------------------------------------------
```

Fig. 15

SEQUENCE LISTING

```
<160> NUMBER OF SEQ ID NOS:  14

<210> SEQ ID NO 1
<211> LENGTH: 2220
<212> TYPE: DNA
<213> ORGANISM: Homo sapiens
<220> FEATURE:
<221> NAME/KEY: CDS
<222> LOCATION: (1)...(1980)

<400> SEQUENCE: 1 aat tcc gga gcc atg gtg aac gaa gcc aga gga aac agc agc ctc aac       48
Asn Ser Gly Ala Met Val Asn Glu Ala Arg Gly Asn Ser Ser Leu Asn
 1               5                  10                  15 ccc tgc ttg gag ggc agt gcc agc agt ggc agt gag agc tcc aaa gat       96
Pro Cys Leu Glu Gly Ser Ala Ser Ser Gly Ser Glu Ser Ser Lys Asp
             20                  25                  30 agt tcg aga tgt tcc acc ccg ggc ctg gac cct gag cgg cat gag aga      144
Ser Ser Arg Cys Ser Thr Pro Gly Leu Asp Pro Glu Arg His Glu Arg
         35                  40                  45 ctc cgg gag aag atg agg cgg cga ttg gaa tct ggt gac aag tgg ttc      192
Leu Arg Glu Lys Met Arg Arg Arg Leu Glu Ser Gly Asp Lys Trp Phe
     50                  55                  60 tcc ctg gaa ttc ttc cct cct cga act gct gag gga gct gtc aat ctc      240
Ser Leu Glu Phe Phe Pro Pro Arg Thr Ala Glu Gly Ala Val Asn Leu
 65                  70                  75                  80 atc tca agg ttt gac cgg atg gca gca ggt ggc ccc ctc tac ata gac      288
Ile Ser Arg Phe Asp Arg Met Ala Ala Gly Gly Pro Leu Tyr Ile Asp
                 85                  90                  95
```

-continued

| | |
|---|---|
| gtg acc tgg cac cca gca ggt gac cct ggc tca gac aag gag acc tcc<br>Val Thr Trp His Pro Ala Gly Asp Pro Gly Ser Asp Lys Glu Thr Ser<br>100                                   105                            110 | 336 |
| tcc atg atg atc gcc agc acc gcc gtg aac tac tgt ggc ctg gag acc<br>Ser Met Met Ile Ala Ser Thr Ala Val Asn Tyr Cys Gly Leu Glu Thr<br>115                               120                             125 | 384 |
| atc ctg cac atg acc tgc tgc cgt cag cgc ctg gag gag atc acg ggc<br>Ile Leu His Met Thr Cys Cys Arg Gln Arg Leu Glu Glu Ile Thr Gly<br>130                                 135                            140 | 432 |
| cat ctg cac aaa gct aag cag ctg ggc ctg aag aac atc atg gcg ctg<br>His Leu His Lys Ala Lys Gln Leu Gly Leu Lys Asn Ile Met Ala Leu<br>145                                  150                       155                       160 | 480 |
| cgg gga gac cca ata ggt gac cag tgg gaa gag gag gga ggc ttc<br>Arg Gly Asp Pro Ile Gly Asp Gln Trp Glu Glu Glu Gly Gly Phe<br>                           165                            170                           175 | 528 |
| aac tac gca gtg gac ctg gtg aag cac atc cga agt gag ttt ggt gac<br>Asn Tyr Ala Val Asp Leu Val Lys His Ile Arg Ser Glu Phe Gly Asp<br>                180                            185                           190 | 576 |
| tac ttt gac atc tgt gtg gca ggt tac ccc aaa ggc cac ccc gaa gca<br>Tyr Phe Asp Ile Cys Val Ala Gly Tyr Pro Lys Gly His Pro Glu Ala<br>            195                            200                           205 | 624 |
| ggg agc ttt gag gct gac ctg aag cac ttg aag gag aag gtg tct gcg<br>Gly Ser Phe Glu Ala Asp Leu Lys His Leu Lys Glu Lys Val Ser Ala<br>210                                  215                       220 | 672 |
| gga gcc gat ttc atc atc acg cag ctt ttc ttt gag gct gac aca ttc<br>Gly Ala Asp Phe Ile Ile Thr Gln Leu Phe Phe Glu Ala Asp Thr Phe<br>225                                  230                       235                       240 | 720 |
| ttc cgc ttt gtg aag gca tgc acc gac atg ggc atc act tgc ccc atc<br>Phe Arg Phe Val Lys Ala Cys Thr Asp Met Gly Ile Thr Cys Pro Ile<br>                       245                            250                           255 | 768 |
| gtc ccc ggg atc ttt ccc atc cag ggc tac cac tcc ctt cgg cag ctt<br>Val Pro Gly Ile Phe Pro Ile Gln Gly Tyr His Ser Leu Arg Gln Leu<br>            260                            265                           270 | 816 |
| gtg aag ctg tcc aag ctg gag gtg cca cag gag atc aag gac gtg att<br>Val Lys Leu Ser Lys Leu Glu Val Pro Gln Glu Ile Lys Asp Val Ile<br>275                                  280                       285 | 864 |
| gag cca atc aaa gac aac gat gct gcc atc cgc aac tat ggc atc gag<br>Glu Pro Ile Lys Asp Asn Asp Ala Ala Ile Arg Asn Tyr Gly Ile Glu<br>290                                  295                       300 | 912 |
| ctg gcc gtg agc ctg tgc cag gag ctt ctg gcc agt ggc ttg gtg cca<br>Leu Ala Val Ser Leu Cys Gln Glu Leu Leu Ala Ser Gly Leu Val Pro<br>305                                  310                       315                       320 | 960 |
| ggc ctc cac ttc tac acc ctc aac cgc gag atg gct acc aca gag gtg<br>Gly Leu His Phe Tyr Thr Leu Asn Arg Glu Met Ala Thr Thr Glu Val<br>                       325                            330                           335 | 1008 |
| ctg aag cgc ctg ggg atg tgg act gag gac ccc agg cgt ccc cta ccc<br>Leu Lys Arg Leu Gly Met Trp Thr Glu Asp Pro Arg Arg Pro Leu Pro<br>            340                            345                           350 | 1056 |
| tgg gct ctc agt gcc cac ccc aag cgc cga gag gaa gat gta cgt ccc<br>Trp Ala Leu Ser Ala His Pro Lys Arg Arg Glu Glu Asp Val Arg Pro<br>                355                            360                           365 | 1104 |
| atc ttc tgg gcc tcc aga cca aag agt tac atc tac cgt acc cag gag<br>Ile Phe Trp Ala Ser Arg Pro Lys Ser Tyr Ile Tyr Arg Thr Gln Glu<br>            370                            375                           380 | 1152 |
| tgg gac gag ttc cct aac ggc cgc tgg ggc aat tcc tct tcc cct gcc<br>Trp Asp Glu Phe Pro Asn Gly Arg Trp Gly Asn Ser Ser Ser Pro Ala<br>385                                  390                       395                       400 | 1200 |
| ttt ggg gag ctg aag gac tac tac ctc ttc tac ctg aag agc aag tcc<br>Phe Gly Glu Leu Lys Asp Tyr Tyr Leu Phe Tyr Leu Lys Ser Lys Ser<br>                405                            410                           415 | 1248 |

```
ccc aag gag gag ctg ctg aag atg tgg ggg gag gag ctg acc agt gaa      1296
Pro Lys Glu Glu Leu Leu Lys Met Trp Gly Glu Glu Leu Thr Ser Glu
            420                 425                 430 gca agt gtc ttt gaa gtc ttt gtt ctt tac ctc tcg gga gaa cca aac      1344
Ala Ser Val Phe Glu Val Phe Val Leu Tyr Leu Ser Gly Glu Pro Asn
        435                 440                 445 cgg aat ggt cac aaa gtg act tgc ctg ccc tgg aac gat gag ccc ctg      1392
Arg Asn Gly His Lys Val Thr Cys Leu Pro Trp Asn Asp Glu Pro Leu
    450                 455                 460 gcg gct gag acc agc ctg ctg aag gag gag ctg ctg cgg gtg aac cgc      1440
Ala Ala Glu Thr Ser Leu Leu Lys Glu Glu Leu Leu Arg Val Asn Arg
465                 470                 475                 480 cag ggc atc ctc acc atc aac tca cag ccc aac atc aac ggg aag ccg      1488
Gln Gly Ile Leu Thr Ile Asn Ser Gln Pro Asn Ile Asn Gly Lys Pro
                485                 490                 495 tcc tcc gac ccc atc gtg ggc tgg ggc ccc agc ggg ggc tat gtc ttc      1536
Ser Ser Asp Pro Ile Val Gly Trp Gly Pro Ser Gly Gly Tyr Val Phe
            500                 505                 510 cag aag gcc tac tta gag ttt ttc act tcc cgc gag aca gcg gaa gca      1584
Gln Lys Ala Tyr Leu Glu Phe Phe Thr Ser Arg Glu Thr Ala Glu Ala
        515                 520                 525 ctt ctg caa gtg ctg aag aag tac gag ctc cgg gtt aat tac cac ctt      1632
Leu Leu Gln Val Leu Lys Lys Tyr Glu Leu Arg Val Asn Tyr His Leu
    530                 535                 540 gtc aat gtg aag ggt gaa aac atc acc aat gcc cct gaa ctg cag ccg      1680
Val Asn Val Lys Gly Glu Asn Ile Thr Asn Ala Pro Glu Leu Gln Pro
545                 550                 555                 560 aat gct gtc act tgg ggc atc ttc cct ggg cga gag atc atc cag ccc      1728
Asn Ala Val Thr Trp Gly Ile Phe Pro Gly Arg Glu Ile Ile Gln Pro
                565                 570                 575 acc gta gtg gat ccc gtc agc ttc atg ttc tgg aag gac gag gcc ttt      1776
Thr Val Val Asp Pro Val Ser Phe Met Phe Trp Lys Asp Glu Ala Phe
            580                 585                 590 gcc ctg tgg att gag cgg tgg gga aag ctg tat gag gag gag tcc ccg      1824
Ala Leu Trp Ile Glu Arg Trp Gly Lys Leu Tyr Glu Glu Glu Ser Pro
        595                 600                 605 tcc cgc acc atc atc cag tac atc cac gac aac tac ttc ctg gtc aac      1872
Ser Arg Thr Ile Ile Gln Tyr Ile His Asp Asn Tyr Phe Leu Val Asn
    610                 615                 620 ctg gtg gac aat gac ttc cca ctg gac aac tgc ctc tgg cag gtg gtg      1920
Leu Val Asp Asn Asp Phe Pro Leu Asp Asn Cys Leu Trp Gln Val Val
625                 630                 635                 640 gaa gac aca ttg gag ctt ctc aac agg ccc acc cag aat gcg aga gaa      1968
Glu Asp Thr Leu Glu Leu Leu Asn Arg Pro Thr Gln Asn Ala Arg Glu
                645                 650                 655 acg gag gct cca tgaccctgcg tcctgacgcc ctgcgttgga gccactcctg         2020
Thr Glu Ala Pro
            660 tcccgccttc ctcctccaca gtgctgcttc tcttgggaac tccactctcc ttcgtgtctc   2080 tcccaccccg gcctccactc ccccacctga caatggcagc tagactggag tgaggcttcc   2140 aggctcttcc tggacctgag tcggccccac atgggaacct agtactctct gctctaaaaa   2200 aaaaaaaaaa aaaggaattc                                                2220

<210> SEQ ID NO 2
<211> LENGTH: 660
<212> TYPE: PRT
<213> ORGANISM: Homo sapiens
```

```
<400> SEQUENCE: 2

Asn Ser Gly Ala Met Val Asn Glu Ala Arg Gly Asn Ser Ser Leu Asn
  1               5                  10                  15

Pro Cys Leu Glu Gly Ser Ala Ser Gly Ser Glu Ser Ser Lys Asp
             20                  25                  30

Ser Ser Arg Cys Ser Thr Pro Gly Leu Asp Pro Glu Arg His Glu Arg
             35                  40                  45

Leu Arg Glu Lys Met Arg Arg Leu Glu Ser Gly Asp Lys Trp Phe
 50                  55                  60

Ser Leu Glu Phe Phe Pro Arg Thr Ala Glu Gly Ala Val Asn Leu
 65                  70                  75                  80

Ile Ser Arg Phe Asp Arg Met Ala Ala Gly Gly Pro Leu Tyr Ile Asp
                 85                  90                  95

Val Thr Trp His Pro Ala Gly Asp Pro Gly Ser Asp Lys Glu Thr Ser
                100                 105                 110

Ser Met Met Ile Ala Ser Thr Ala Val Asn Tyr Cys Gly Leu Glu Thr
                115                 120                 125

Ile Leu His Met Thr Cys Cys Arg Gln Arg Leu Glu Glu Ile Thr Gly
    130                 135                 140

His Leu His Lys Ala Lys Gln Leu Gly Leu Lys Asn Ile Met Ala Leu
145                 150                 155                 160

Arg Gly Asp Pro Ile Gly Asp Gln Trp Glu Glu Glu Gly Gly Phe
                165                 170                 175

Asn Tyr Ala Val Asp Leu Val Lys His Ile Arg Ser Glu Phe Gly Asp
                180                 185                 190

Tyr Phe Asp Ile Cys Val Ala Gly Tyr Pro Lys Gly His Pro Glu Ala
                195                 200                 205

Gly Ser Phe Glu Ala Asp Leu Lys His Leu Lys Glu Lys Val Ser Ala
210                 215                 220

Gly Ala Asp Phe Ile Ile Thr Gln Leu Phe Phe Glu Ala Asp Thr Phe
225                 230                 235                 240

Phe Arg Phe Val Lys Ala Cys Thr Asp Met Gly Ile Thr Cys Pro Ile
                245                 250                 255

Val Pro Gly Ile Phe Pro Ile Gln Gly Tyr His Ser Leu Arg Gln Leu
                260                 265                 270

Val Lys Leu Ser Lys Leu Glu Val Pro Gln Glu Ile Lys Asp Val Ile
            275                 280                 285

Glu Pro Ile Lys Asp Asn Asp Ala Ala Ile Arg Asn Tyr Gly Ile Glu
            290                 295                 300

Leu Ala Val Ser Leu Cys Gln Glu Leu Leu Ala Ser Gly Leu Val Pro
305                 310                 315                 320

Gly Leu His Phe Tyr Thr Leu Asn Arg Glu Met Ala Thr Thr Glu Val
                325                 330                 335

Leu Lys Arg Leu Gly Met Trp Thr Glu Asp Pro Arg Pro Leu Pro
                340                 345                 350

Trp Ala Leu Ser Ala His Pro Lys Arg Glu Glu Asp Val Arg Pro
                355                 360                 365

Ile Phe Trp Ala Ser Arg Pro Lys Ser Tyr Ile Tyr Arg Thr Gln Glu
                370                 375                 380

Trp Asp Glu Phe Pro Asn Gly Arg Trp Gly Asn Ser Ser Pro Ala
385                 390                 395                 400

Phe Gly Glu Leu Lys Asp Tyr Tyr Leu Phe Tyr Leu Lys Ser Lys Ser
                405                 410                 415
```

-continued

```
Pro Lys Glu Glu Leu Leu Lys Met Trp Gly Glu Leu Thr Ser Glu
            420                 425                 430

Ala Ser Val Phe Glu Val Phe Val Leu Tyr Leu Ser Gly Glu Pro Asn
        435                 440                 445

Arg Asn Gly His Lys Val Thr Cys Leu Pro Trp Asn Asp Glu Pro Leu
    450                 455                 460

Ala Ala Glu Thr Ser Leu Leu Lys Glu Glu Leu Leu Arg Val Asn Arg
465                 470                 475                 480

Gln Gly Ile Leu Thr Ile Asn Ser Gln Pro Asn Ile Asn Gly Lys Pro
                485                 490                 495

Ser Ser Asp Pro Ile Val Gly Trp Gly Pro Ser Gly Gly Tyr Val Phe
            500                 505                 510

Gln Lys Ala Tyr Leu Glu Phe Phe Thr Ser Arg Glu Thr Ala Glu Ala
        515                 520                 525

Leu Leu Gln Val Leu Lys Lys Tyr Glu Leu Arg Val Asn Tyr His Leu
    530                 535                 540

Val Asn Val Lys Gly Glu Asn Ile Thr Asn Ala Pro Glu Leu Gln Pro
545                 550                 555                 560

Asn Ala Val Thr Trp Gly Ile Phe Pro Gly Arg Glu Ile Ile Gln Pro
                565                 570                 575

Thr Val Val Asp Pro Val Ser Phe Met Phe Trp Lys Asp Glu Ala Phe
            580                 585                 590

Ala Leu Trp Ile Glu Arg Trp Gly Lys Leu Tyr Glu Glu Ser Pro
        595                 600                 605

Ser Arg Thr Ile Ile Gln Tyr Ile His Asp Asn Tyr Phe Leu Val Asn
    610                 615                 620

Leu Val Asp Asn Asp Phe Pro Leu Asp Asn Cys Leu Trp Gln Val Val
625                 630                 635                 640

Glu Asp Thr Leu Glu Leu Leu Asn Arg Pro Thr Gln Asn Ala Arg Glu
                645                 650                 655

Thr Glu Ala Pro
            660

<210> SEQ ID NO 3
<211> LENGTH: 2219
<212> TYPE: DNA
<213> ORGANISM: Homo sapiens
<220> FEATURE:
<221> NAME/KEY: CDS
<222> LOCATION: (13)...(1983)

<400> SEQUENCE: 3
aattccggag cc atg gtg aac gaa gcc aga gga aac agc agc ctc aac ccc        51
              Met Val Asn Glu Ala Arg Gly Asn Ser Ser Leu Asn Pro
                1               5                  10 tgc ttg gag ggc agt gcc agc agt ggc agt gag agc tcc aaa gat agt        99
Cys Leu Glu Gly Ser Ala Ser Ser Gly Ser Glu Ser Ser Lys Asp Ser
    15                  20                  25 tcg aga tgt tcc acc ccg ggc ctg gac cct gag cgg cat gag aga ctc       147
Ser Arg Cys Ser Thr Pro Gly Leu Asp Pro Glu Arg His Glu Arg Leu
30                  35                  40                  45 cgg gag aag atg agg cgg cga ttg gaa tct ggt gac aag tgg ttc tcc       195
Arg Glu Lys Met Arg Arg Arg Leu Glu Ser Gly Asp Lys Trp Phe Ser
                50                  55                  60 ctg gaa ttc ttc cct cct cga act gct gag gga gct gtc aat ctc atc       243
Leu Glu Phe Phe Pro Pro Arg Thr Ala Glu Gly Ala Val Asn Leu Ile
            65                  70                  75
```

-continued

```
tca agg ttt gac cgg atg gca gca ggt ggc ccc ctc tac ata gac gtg    291
Ser Arg Phe Asp Arg Met Ala Ala Gly Gly Pro Leu Tyr Ile Asp Val
     80                  85                  90 acc tgg cac cca gca ggt gac cct ggc tca gac aag gag acc tcc tcc    339
Thr Trp His Pro Ala Gly Asp Pro Gly Ser Asp Lys Glu Thr Ser Ser
 95                 100                 105 atg atg atc gcc agc acc gcc gtg aac tac tgt ggc ctg gag acc atc    387
Met Met Ile Ala Ser Thr Ala Val Asn Tyr Cys Gly Leu Glu Thr Ile
110                 115                 120                 125 ctg cac atg acc tgc tgc cgt cag cgc ctg gag gag atc acg ggc cat    435
Leu His Met Thr Cys Cys Arg Gln Arg Leu Glu Glu Ile Thr Gly His
                130                 135                 140 ctg cac aaa gct aag cag ctg ggc ctg aag aac atc atg gcg ctg cgg    483
Leu His Lys Ala Lys Gln Leu Gly Leu Lys Asn Ile Met Ala Leu Arg
            145                 150                 155 gga gac cca ata ggt gac cag tgg gaa gag gag gag gga ggc ttc aac    531
Gly Asp Pro Ile Gly Asp Gln Trp Glu Glu Glu Glu Gly Gly Phe Asn
        160                 165                 170 tac gca gtg gac ctg gtg aag cac atc cga agt gag ttt ggt gac tac    579
Tyr Ala Val Asp Leu Val Lys His Ile Arg Ser Glu Phe Gly Asp Tyr
    175                 180                 185 ttt gac atc tgt gtg gca ggt tac ccc aaa ggc cac ccc gaa gca ggg    627
Phe Asp Ile Cys Val Ala Gly Tyr Pro Lys Gly His Pro Glu Ala Gly
190                 195                 200                 205 agc ttt gag gct gac ctg aag cac ttg aag gag aag gtg tct gcg gga    675
Ser Phe Glu Ala Asp Leu Lys His Leu Lys Glu Lys Val Ser Ala Gly
                210                 215                 220 gcc gat ttc atc atc acg cag ctt ttc ttt gag gct gac aca ttc ttc    723
Ala Asp Phe Ile Ile Thr Gln Leu Phe Phe Glu Ala Asp Thr Phe Phe
            225                 230                 235 cgc ttt gtg aag gca tgc acc gac atg ggc atc act tgc ccc atc gtc    771
Arg Phe Val Lys Ala Cys Thr Asp Met Gly Ile Thr Cys Pro Ile Val
        240                 245                 250 ccc ggg atc ttt ccc atc cag ggc tac cac tcc ctt cgg cag ctt gtg    819
Pro Gly Ile Phe Pro Ile Gln Gly Tyr His Ser Leu Arg Gln Leu Val
    255                 260                 265 aag ctg tcc aag ctg gag gtg cca cag gag atc aag gac gtg att gag    867
Lys Leu Ser Lys Leu Glu Val Pro Gln Glu Ile Lys Asp Val Ile Glu
270                 275                 280                 285 cca atc aaa gac aac gat gct gcc atc cgc aac tat ggc atc gag ctg    915
Pro Ile Lys Asp Asn Asp Ala Ala Ile Arg Asn Tyr Gly Ile Glu Leu
                290                 295                 300 gcc gtg agc ctg tgc cag gag ctt ctg gcc agt ggc ttg gtg cca ggc    963
Ala Val Ser Leu Cys Gln Glu Leu Leu Ala Ser Gly Leu Val Pro Gly
            305                 310                 315 ctc cac ttc tac acc ctc aac cgc gag atg gct acc aca gag gtg ctg   1011
Leu His Phe Tyr Thr Leu Asn Arg Glu Met Ala Thr Thr Glu Val Leu
        320                 325                 330 aag cgc ctg ggg atg tgg act gag gac ccc agg cgt ccc cta ccc tgg   1059
Lys Arg Leu Gly Met Trp Thr Glu Asp Pro Arg Arg Pro Leu Pro Trp
    335                 340                 345 gct ctc agt gcc cac ccc aag cgc cga gag gaa gat gta cgt ccc atc   1107
Ala Leu Ser Ala His Pro Lys Arg Arg Glu Glu Asp Val Arg Pro Ile
350                 355                 360                 365 ttc tgg gcc tcc aga cca aag agt tac atc tac cgt acc cag gag tgg   1155
Phe Trp Ala Ser Arg Pro Lys Ser Tyr Ile Tyr Arg Thr Gln Glu Trp
                370                 375                 380 gac gag ttc cct aac ggc cgc tgg ggc aat tcc tct tcc cct gcc ttt   1203
Asp Glu Phe Pro Asn Gly Arg Trp Gly Asn Ser Ser Ser Pro Ala Phe
```

```
                    385                      390                      395
ggg gag ctg aag gac tac tac ctc ttc tac ctg aag agc aag tcc ccc          1251
Gly Glu Leu Lys Asp Tyr Tyr Leu Phe Tyr Leu Lys Ser Lys Ser Pro
            400                      405                      410 aag gag gag ctg ctg aag atg tgg ggg gag gag ctg acc agt gaa gca          1299
Lys Glu Glu Leu Leu Lys Met Trp Gly Glu Glu Leu Thr Ser Glu Ala
    415                      420                      425 agt gtc ttt gaa gtc ttt gtt ctt tac ctc tcg gga gaa cca aac cgg          1347
Ser Val Phe Glu Val Phe Val Leu Tyr Leu Ser Gly Glu Pro Asn Arg
430                      435                      440                      445 aat ggt cac aaa gtg act tgc ctg ccc tgg aac gat gag ccc ctg gcg          1395
Asn Gly His Lys Val Thr Cys Leu Pro Trp Asn Asp Glu Pro Leu Ala
                450                      455                      460 gct gag acc agc ctg ctg aag gag gag ctg ctg cgg gtg aac cgc cag          1443
Ala Glu Thr Ser Leu Leu Lys Glu Glu Leu Leu Arg Val Asn Arg Gln
            465                      470                      475 ggc atc ctc acc atc aac tca cag ccc aac atc aac ggg aag ccg tcc          1491
Gly Ile Leu Thr Ile Asn Ser Gln Pro Asn Ile Asn Gly Lys Pro Ser
        480                      485                      490 tcc gac ccc atc gtg ggc tgg ggc ccc agc ggg ggc tat gtc ttc cag          1539
Ser Asp Pro Ile Val Gly Trp Gly Pro Ser Gly Gly Tyr Val Phe Gln
495                      500                      505 aag gcc tac tta gag ttt ttc act tcc cgc gag aca gcg gaa gca ctt          1587
Lys Ala Tyr Leu Glu Phe Phe Thr Ser Arg Glu Thr Ala Glu Ala Leu
510                      515                      520                      525 ctg caa gtg ctg aag aag tac gag ctc cgg gtt aat tac cac ctt gtc          1635
Leu Gln Val Leu Lys Lys Tyr Glu Leu Arg Val Asn Tyr His Leu Val
                530                      535                      540 aat gtg aag ggt gaa aac atc acc aat gcc cct gaa ctg cag ccg aat          1683
Asn Val Lys Gly Glu Asn Ile Thr Asn Ala Pro Glu Leu Gln Pro Asn
            545                      550                      555 gct gtc act tgg ggc atc ttc cct ggg cga gag atc atc cag ccc acc          1731
Ala Val Thr Trp Gly Ile Phe Pro Gly Arg Glu Ile Ile Gln Pro Thr
        560                      565                      570 gta gtg gat ccc gtc agc ttc atg ttc tgg aag gac gag gcc ttt gcc          1779
Val Val Asp Pro Val Ser Phe Met Phe Trp Lys Asp Glu Ala Phe Ala
575                      580                      585 ctg tgg att gag cgg tgg gga aag ctg tat gag gag gag tcc ccg tcc          1827
Leu Trp Ile Glu Arg Trp Gly Lys Leu Tyr Glu Glu Glu Ser Pro Ser
590                      595                      600                      605 cgc acc atc atc cag tac atc cac gac aac tac ttc ctg gtc aac ctg          1875
Arg Thr Ile Ile Gln Tyr Ile His Asp Asn Tyr Phe Leu Val Asn Leu
                610                      615                      620 gtg gac aat gac ttc cca ctg gac aac tgc ctc tgg cag gtg gtg gaa          1923
Val Asp Asn Asp Phe Pro Leu Asp Asn Cys Leu Trp Gln Val Val Glu
            625                      630                      635 gac aca ttg gag ctt ctc aac agg ccc acc cag aat gcg aga gaa acg          1971
Asp Thr Leu Glu Leu Leu Asn Arg Pro Thr Gln Asn Ala Arg Glu Thr
        640                      645                      650 gag gct cca tga ccctgcgtcc tgacgccctg cgttggagcc actcctgtcc              2023
Glu Ala Pro  *
        655 cgccttcctc ctccacagtg ctgcttctct tgggaactcc actctccttc gtgtctctcc        2083 caccccggcc tccactcccc cacctgacaa tggcagctag actggagtga ggcttccagg        2143 ctcttcctgg acctgagtcg gccccacatg ggaacctagt actctctgct ctaaaaaaaa        2203 aaaaaaaaaa ggaatt                                                        2219
```

-continued

<210> SEQ ID NO 4
<211> LENGTH: 656
<212> TYPE: PRT
<213> ORGANISM: Homo sapiens

<400> SEQUENCE: 4

```
Met Val Asn Glu Ala Arg Gly Asn Ser Ser Leu Asn Pro Cys Leu Glu
  1               5                  10                  15

Gly Ser Ala Ser Gly Ser Glu Ser Ser Lys Asp Ser Ser Arg Cys
             20                  25                  30

Ser Thr Pro Gly Leu Asp Pro Glu Arg His Glu Arg Leu Arg Glu Lys
             35                  40                  45

Met Arg Arg Arg Leu Glu Ser Gly Asp Lys Trp Phe Ser Leu Glu Phe
 50                  55                  60

Phe Pro Pro Arg Thr Ala Glu Gly Ala Val Asn Leu Ile Ser Arg Phe
 65                  70                  75                  80

Asp Arg Met Ala Ala Gly Gly Pro Leu Tyr Ile Asp Val Thr Trp His
                 85                  90                  95

Pro Ala Gly Asp Pro Gly Ser Asp Lys Glu Thr Ser Ser Met Met Ile
                100                 105                 110

Ala Ser Thr Ala Val Asn Tyr Cys Gly Leu Glu Thr Ile Leu His Met
                115                 120                 125

Thr Cys Cys Arg Gln Arg Leu Glu Glu Ile Thr Gly His Leu His Lys
                130                 135                 140

Ala Lys Gln Leu Gly Leu Lys Asn Ile Met Ala Leu Arg Gly Asp Pro
145                 150                 155                 160

Ile Gly Asp Gln Trp Glu Glu Glu Gly Gly Phe Asn Tyr Ala Val
                165                 170                 175

Asp Leu Val Lys His Ile Arg Ser Glu Phe Gly Asp Tyr Phe Asp Ile
                180                 185                 190

Cys Val Ala Gly Tyr Pro Lys Gly His Pro Glu Ala Gly Ser Phe Glu
                195                 200                 205

Ala Asp Leu Lys His Leu Lys Glu Lys Val Ser Ala Gly Ala Asp Phe
                210                 215                 220

Ile Ile Thr Gln Leu Phe Phe Glu Ala Asp Thr Phe Phe Arg Phe Val
225                 230                 235                 240

Lys Ala Cys Thr Asp Met Gly Ile Thr Cys Pro Ile Val Pro Gly Ile
                245                 250                 255

Phe Pro Ile Gln Gly Tyr His Ser Leu Arg Gln Leu Val Lys Leu Ser
                260                 265                 270

Lys Leu Glu Val Pro Gln Glu Ile Lys Asp Val Ile Glu Pro Ile Lys
                275                 280                 285

Asp Asn Asp Ala Ala Ile Arg Asn Tyr Gly Ile Glu Leu Ala Val Ser
                290                 295                 300

Leu Cys Gln Glu Leu Leu Ala Ser Gly Leu Val Pro Gly Leu His Phe
305                 310                 315                 320

Tyr Thr Leu Asn Arg Glu Met Ala Thr Thr Glu Val Leu Lys Arg Leu
                325                 330                 335

Gly Met Trp Thr Glu Asp Pro Arg Arg Pro Leu Pro Trp Ala Leu Ser
                340                 345                 350

Ala His Pro Lys Arg Arg Glu Glu Asp Val Arg Pro Ile Phe Trp Ala
                355                 360                 365

Ser Arg Pro Lys Ser Tyr Ile Tyr Arg Thr Gln Glu Trp Asp Glu Phe
                370                 375                 380
```

```
Pro Asn Gly Arg Trp Gly Asn Ser Ser Pro Ala Phe Gly Glu Leu
385                 390                 395                 400

Lys Asp Tyr Tyr Leu Phe Tyr Leu Lys Ser Lys Ser Pro Lys Glu Glu
            405                 410                 415

Leu Leu Lys Met Trp Gly Glu Glu Leu Thr Ser Glu Ala Ser Val Phe
            420                 425                 430

Glu Val Phe Val Leu Tyr Leu Ser Gly Glu Pro Asn Arg Asn Gly His
            435                 440                 445

Lys Val Thr Cys Leu Pro Trp Asn Asp Glu Pro Leu Ala Ala Glu Thr
            450                 455                 460

Ser Leu Leu Lys Glu Glu Leu Leu Arg Val Asn Arg Gln Gly Ile Leu
465                 470                 475                 480

Thr Ile Asn Ser Gln Pro Asn Ile Asn Gly Lys Pro Ser Ser Asp Pro
            485                 490                 495

Ile Val Gly Trp Gly Pro Ser Gly Gly Tyr Val Phe Gln Lys Ala Tyr
            500                 505                 510

Leu Glu Phe Phe Thr Ser Arg Glu Thr Ala Glu Ala Leu Leu Gln Val
            515                 520                 525

Leu Lys Lys Tyr Glu Leu Arg Val Asn Tyr His Leu Val Asn Val Lys
            530                 535                 540

Gly Glu Asn Ile Thr Asn Ala Pro Glu Leu Gln Pro Asn Ala Val Thr
545                 550                 555                 560

Trp Gly Ile Phe Pro Gly Arg Glu Ile Ile Gln Pro Thr Val Val Asp
            565                 570                 575

Pro Val Ser Phe Met Phe Trp Lys Asp Glu Ala Phe Ala Leu Trp Ile
            580                 585                 590

Glu Arg Trp Gly Lys Leu Tyr Glu Glu Ser Pro Ser Arg Thr Ile
            595                 600                 605

Ile Gln Tyr Ile His Asp Asn Tyr Phe Leu Val Asn Leu Val Asp Asn
            610                 615                 620

Asp Phe Pro Leu Asp Asn Cys Leu Trp Gln Val Val Glu Asp Thr Leu
625                 630                 635                 640

Glu Leu Leu Asn Arg Pro Thr Gln Asn Ala Arg Glu Thr Glu Ala Pro
            645                 650                 655
```

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
agcctcaacc cctgcttgga gg                                       22

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
tgacagtttg ctccccaggc ac                                       22

<210> SEQ ID NO 7
<211> LENGTH: 23
<212> TYPE: DNA

```
<213> ORGANISM: Artificial Sequence
<220> FEATURE:
<223> OTHER INFORMATION: Synthetic primer

<400> SEQUENCE: 7
tgaaggagaa ggtgtctgcg gga                                              23

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
aggacggtgc ggtgagagtg g                                                21

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9
cactgtggtt ggcatggatg atg                                              23

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
ggctgctctt ggaccctcct c                                                21

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
tgcttccggc tccctctagc c                                                21

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
cctcccgctc ccaagaacaa ag                                               22

<210> SEQ ID NO 13
<211> LENGTH: 23
<212> TYPE: DNA
<213> ORGANISM: Artificial Sequence
<220> FEATURE:
<223> OTHER INFORMATION: Synthetic primer

<400> SEQUENCE: 13
tgaaggagaa ggtgtctgcg gga                                              23
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
aggacggtgc ggtgagagtg                                              20
```

METHODS FOR DETECTING HUMAN METHYLENE TETRAHYDROFOLATE REDUCTASE ALLELIC VARIANTS

RELATED APPLICATION

This application is a continuation-in-part of U.S. patent application Ser. No. 08/738,000 filed Feb. 12, 1997, now U.S. Pat. No. 6,074,821, which is the National Stage of International Application No. PCT/CA95/00314, filed May 25, 1995.

BACKGROUND OF THE INVENTION (a) Field of the Invention

The invention relates to a cDNA probe for human methylenetetrahydrofolate reductase (MTHFR), and its uses.

(b) Description of Prior Art

Folic acid derivatives are coenzymes for several critical single-carbon transfer reactions, including reactions in the biosynthesis of purines, thymidylate and methionine. Methylenetetrahydrofolate reductase (MTHFR; EC 1.5.1.20) catalyses the NADPH-linked reduction of 5,10-methylenetetrahydrofolate to 5-methyltetrahydrofolate, a co-substrate for methylation of homocysteine to methionine. The porcine liver enzyme, a flavoprotein, has been purified to homogeneity; it is a homodimer of 77-kDa subunits. Partial proteolysis of the porcine peptide has revealed two spatially distinct domains: an N-terminal domain of 40 kDa and a C-terminal domain of 37 kDa. The latter domain contains the binding site for the allosteric regulator S-adenosylmethionine.

Hereditary deficiency of MTHFR, an autosomal recessive disorder, is the most common inborn error of folic acid metabolism. A block in the production of methyltetrahydrofolate leads to elevated homocysteine with low to normal levels of methionine. Patients with severe deficiencies of MTHFR (0–20% activity in fibroblasts) can have variable phenotypes. Developmental delay, mental retardation, motor and gait abnormalities, peripheral neuropathy, seizures and psychiatric disturbances have been reported in this group, although at least one patient with severe MTHFR deficiency was asymptomatic. Pathologic changes in the severe form include the vascular changes that have been found in other conditions with elevated homocysteine, as well as reduced neurotransmitter and methionine levels in the CNS. A milder deficiency of MTHFR (35–50% activity) has been described in patients with coronary artery disease (see below). Genetic heterogeneity is likely, considering the diverse clinical features, the variable levels of enzyme activity, and the differential heat inactivation profiles of the reductase in patients' cells.

Coronary artery disease (CAD) accounts for 25% of deaths of Canadians. Cardiovascular risk factors (male sex, family history, smoking, hypertension, dyslipoproteinemia and diabetes) account for approximately 60 to 70% of the ability to discriminate CAD patients from healthy subjects. Elevated plasma homocysteine has also been shown to be an independent risk factor for cardiovascular disease.

Homocysteine is a sulfhydryl-containing amino acid that is formed by the demethylation of methionine. It is normally metabolized to cysteine (transsulfuration) or re-methylated to methionine. Inborn errors of metabolism (as in severe MTHFR deficiency) causing extreme elevations of homocysteine in plasma, with homocystinuria, are associated with premature vascular disease and widespread arterial and venous thrombotic phenomena. Milder elevations of plasma homocysteine (as in mild MTHFR deficiency) have been associated with the development of peripheral vascular disease, cerebrovascular disease and premature CAD.

Homocysteine remethylation to methionine requires the folic acid intermediate, 5-methyltetrahydrofolate, which is produced from 5,10-methylenetetrahydrofolate folate through the action of 5,10-methylenetetrahydrofolate reductase (MTHFR). Deficiency of MTHFR results in an inability to metabolize homocysteine to methionine; elevated plasma homocysteine and decreased methionine are the metabolic consequences of the block. Severe deficiencies of MTHFR (less than 20% of activity of controls) as described above, are associated with early-onset neurologic symptoms (mental retardation, peripheral neuropathy, seizures, etc.) and with atherosclerotic changes and thromboembolism. Milder deficiencies of MTHFR (35–50% of activity of controls), with a thermolabile form of the enzyme, are seen in patients with cardiovascular disease without obvious neurologic abnormalities.

In a survey of 212 patients with proven coronary artery disease, the thermolabile form of MTHFR was found in 17% of the CAD group and 5% of controls. In a subsequent report on 339 subjects who underwent coronary angiography, a correlation was found between thermolabile MTHFR and the degree of coronary artery stenosis. Again, traditional risk factors (age, sex, smoking, hypertension, etc.) were not significantly associated with thermolabile MTHFR. All the studies on MTHFR were performed by enzymatic assays of MTHFR in lymphocytes, with measurements of activity before and after heat treatment to determine thermolability of the enzyme.

Since 5-methyltetrahydrofolate, the product of the MTHFR reaction, is the primary form of circulatory folate, a deficiency in MTHFR might lead to other types of disorders. For example, periconceptual folate administration to women reduces the occurrence and recurrence of neural tube defects in their offspring. Neural tube defects are a group of developmental malformations (meningomyelocele, anencephaly, and encephalocele) that arise due to failure of closure of the neural tube. Elevated levels of plasma homocysteine have been reported in mothers of children with neural tube defects. The elevated plasma homocysteine could be due to a deficiency of MTHFR, as described above for cardiovascular disease.

Neuroblastomas are tumors derived from neural crest cells. Many of these tumors have been reported to have deletions of human chromosome region 1p36, the region of the genome to which MTHFR has been mapped. It is possible that MTHFR deletions/mutations are responsible for or contribute to the formation of this type of tumor. MTHFR abnormalities may also contribution to the formation of other types of tumors, such as colorectal tumors, since high dietary folate has been shown to be inversely associated with risk of colorectal carcinomas.

MTHFR activity is required for homocysteine methylation to methionine. Methionine is necessary for the formation of S-adenosylmethionine, the primary methyl donor for methylation of DNA, proteins, lipids, neurotransmitters, etc. Abnormalities in MTHFR might lead to lower levels of methionine and S-adenosylme-thionine, as well as to elevated homocysteine. Disruption of methylation processes could result in a wide variety of conditions, such as neoplasias, developmental anomalies, neurologic disorders, etc.

Although the MTHFR gene in *Escherichia coli* (metF) has been isolated and sequenced, molecular studies of the enzyme in higher organisms have been limited without the availability of an eukaryotic cDNA.

It would be highly desirable to be provided with a cDNA probe for human methylenetetrahydrofolate reductase (MTHFR). This probe would be used for identification of sequence abnormalities in individuals with severe or mild MTHFR deficiency, including cardiovascular patients and patients with neurologic symptoms or tumors. The probe would also be used in gene therapy, isolation of the gene, and expression studies to produce the MTHFR protein. The probe would also provide the amino acid sequence of the human MTHFR protein, which would be useful for therapy of MTHFR deficiency by biochemical or pharmacological approaches.

It would be highly desirable to be provided with a molecular description of mutations in methylenetetrahydrofolate reductase deficiency.

Patients with sequence abnormalities in MTHFR might have different responses to drugs, possibly but not limited to drugs that affect folate metabolism. Therefore, it would be useful to know if these mutations are present before determining the appropriate therapy. The drugs/diseases for which this might be relevant include cancer chemotherapeutic agents, antibiotics, antiepileptic medication, antiarthritic medication, etc.

SUMMARY OF THE INVENTION

One aim of the present invention is to provide a cDNA probe for human methylenetetrahydrofolate reductase (MTHFR).

Another aim of the present invention is to provide a molecular description of mutations in methylenetetrahydrofolate reductase deficiency.

Another aim of the present invention is to provide a nucleic acid and amino acid sequence for human methylenetetrahydrofolate reductase.

Another aim of the present invention is to provide potential therapy for individuals with methylenetetrahydrofolate reductase deficiency.

Another aim of the present invention is to provide a system for synthesis of MTHFR protein in vitro.

A further aim of the present invention is to provide technology/protocol for identification of sequence changes in the MTHFR gene.

In accordance with one aspect of the present invention, there is provided a cDNA probe for human methylenetetrahydrofolate reductase (MTHFR) gene encoded by a nucleotide sequence as set forth in SEQ ID NO:1 or having an amino acid sequence as set forth in SEQ ID NO:2. The probe comprises a nucleotide sequence that hybridizes to the MTHFR nucleotide sequence, or an amino acid sequence that hybridizes to the MTHFR amino acid sequence.

In accordance with another aspect of the present invention, there is provided a method of diagnosis of methylenetetrahydrofolate reductase (MTHFR) deficiency in a patient with MTHFR deficiency. The method comprises the steps of amplifying a DNA sample obtained from the patient or reverse-transcripting a RNA sample obtained from the patient into a DNA and amplifying the DNA, and analyzing the amplified DNA to determine at least one sequence abnormality with respect to a human MTHFR encoded by a nucleotide sequence as set forth in SEQ ID NO:1 or having an amino acid sequence as set forth in SEQ ID NO:2, the sequence abnormality being indicative of MTHFR deficiency.

The sequence abnormality may comprise a mutation selected from a group consisting of 167G→A, 482G→A, 559C→T, 677C→T, 692C→T, 764C→T, 792+1G→A, 985C→T, 1015C→T, 1081C→T, 1298A→C and 1317T→C.

The selected mutation may consist of 677C→T.

The MTHFR deficiency may be associated with a disorder selected from a group consisting of cardiovascular disorders, cancer, osteoporosis, increased risk of occurrence of a neural tube defect in an offspring of said patient, neurological disorders and disorders influenced by folic acid metabolism.

The cancer may be selected from a group consisting of neuroblastomas and colorectal carcinomas.

The disorder may consist of osteoporosis.

In accordance with yet another aspect of the present invention, there is provided a method for gene therapy of methylenetetrahydrofolate reductase (MTHFR) deficiency in a patient. The method comprises the steps of producing a recombinant vector for expression of MTHFR under the control of a suitable promoter, the MTHFR being encoded by a nucleotide sequence as set forth in SEQ ID NO:1 or having an amino acid sequence as set forth in SEQ ID NO:2, and transfecting the patient with the vector for expression of MTHFR.

In accordance with yet another aspect of the present invention, there is provided a human methylenetetrahydrofolate reductase (MTHFR) protein encoded by a nucleotide sequence as set forth in SEQ ID NO:1 or having an amino acid sequence as set forth in SEQ ID NO:2.

In accordance with yet another aspect of the present invention, there is provided a recombinant human methylenetetrahydrofolate reductase (MTHFR) protein encoded by a nucleotide sequence as set forth in SEQ ID NO:1 or having an amino acid sequence as set forth in SEQ ID NO:2.

In accordance with yet another aspect of the present invention, there is provided a method of treatment of MTHFR-deficiency in a patient that comprises administering such a MTHFR protein.

The MTHFR deficiency may be associated with a cancer.

The cancer may be selected from a group consisting of neuroblastomas and colorectal carcinomas.

In accordance with yet another aspect of the present invention, there is provided a method of preventing an occurrence of a neural tube defect in an offspring of a patient. The method comprises administering to the patient such a MTHFR protein.

In accordance with yet another aspect of the present invention, there is provided a method for determining susceptibility, response or toxicity of a drug with a patient having a methylenetetrahydrofolate reductase (MTHFR) deficiency. The method comprises the steps of amplifying a DNA sample obtained from the patient or reverse-transcripting a RNA sample obtained from the patient into a DNA and amplifying said DNA, analyzing the amplified DNA to determine a sequence abnormality in a MTHFR sequence, the MTHFR sequence being encoded by a nucleotide sequence as set forth in SEQ ID NO:1 or having an amino acid sequence as set forth in SEQ ID NO:2, and administering the drug to the patient and determining the sequence abnormality associated with the patient susceptibility, response or toxicity to the drug.

The sequence abnormality may comprise a mutation selected from a group consisting of 167G→A, 482G→A, 559C→T, 677C→T, 692C→T, 764C→T, 792+1G→A, 985C→T, 1015C→T, 1081C→T, 1298A→C and 1317T→C and the drug may be selected from a group consisting of cancer chemotherapeutic agents, antibiotics, antiepileptic agents and antiarthritic agents.

The MTHFR deficiency may be associated with a disorder selected from a group consisting of cardiovascular disorders, coronary and arterial disorders, neurological disorders, increased risk of occurrence of a neural tube defect in an offspring, cancer, osteoporosis and other disorders influenced by folic acid metabolism.

In accordance with yet another aspect of the present invention, there is provided a method of treatment of a patient having a cancer comprising the step of inhibiting gene expression for a MTHFR protein or a mRNA produced form the gene.

In accordance with yet another aspect of the present invention, there is provided a method of treatment of a patient having a cancer comprising the step of inhibiting the MTHFR protein.

A "polymorphism" is intended to mean a mutation present in 1% or more of alleles of the general population. A polymorphism is disease-causing when it is present in patients with a disease but not in the general population. However, a polymorphism present both in patients having a disease and in the general population is not necessarily benign. The definition of a disease-causing substitution, as distinct from a benign polymorphism, is based on 3 factors: (1) absence of the change in at least 50 independent control chromosomes; (2) presence of the amino acid in the bacterial enzyme, attesting to its evolutionary significance and (3) change in amino acid not conservative. Although expression of the substitutions is required to formally prove that they are not benign, the criteria above allow us to postulate that the changes described in this report are likely to affect activity.

BRIEF DESCRIPTION OF THE DRAWINGS

FIGS. 1A to 1F illustrate the first cDNA coding sequence (SEQ ID NO:1 and NO:2) for methylenetetrahydrofolate reductase (MTHFR);

FIG. 2 is the alignment of amino acids for human methylenetetrahydrofolate reductase (MTHFR), the metF genes from *E. Coli* (ECOMETF), and *S. Typhimurium* (STYMETF), and an unidentified open reading frame in *Saccharomyces cerevisiae* that is divergently transcribed from an excision repair gene (ysRAD1);

FIGS. 6A to 6C illustrate the total available sequence (SEQ ID NO:3 and NO:4) of human MTHFR cDNA;

FIGS. 12A–12B illustrate the exonic sequences of the human MTHFR gene with their flanking intronic sequences;

FIGS. 13A–13B illustrate the exonic sequences of the mouse MTHFR gene with their flanking intronic sequences;

FIG. 15 illustrates the alignment of MTHFR amino acid sequences for the human MTHFR (hMTHFR), mouse MTHFR (mMTHFR) and the MetF gene of bacteria (bMTHFR).

DETAILED DESCRIPTION OF THE INVENTION

Sequencing of peptides from porcine MTHFR

Figure 3A:
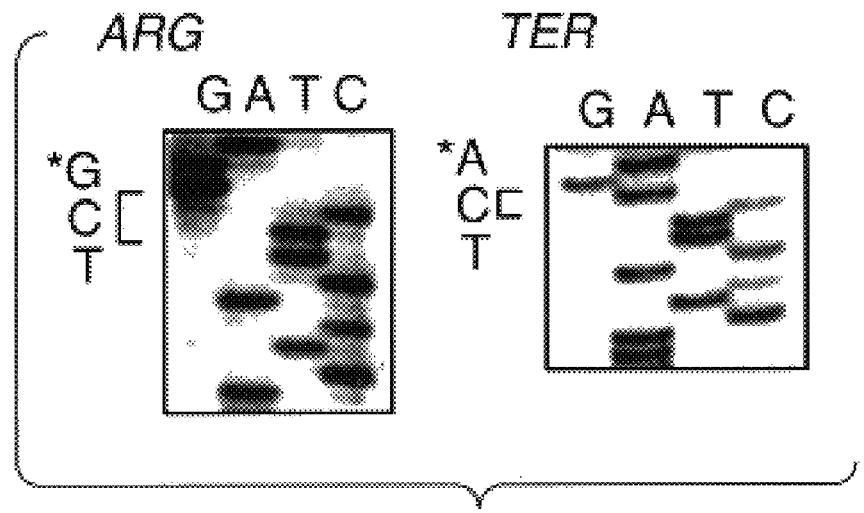
FIGS. 3A and 3B illustrate the sequencing and restriction enzyme analysis for the Arg to Ter substitution.

Homogeneous native porcine MTHFR was digested with trypsin to generate a 40 kDa N-terminal fragment and a 31 kDa C-terminal fragment; the 31 kDa fragment is a proteolytic product of the 37 kDa fragment. The fragments were separated by SDS-PAGE, electroeluted, and the denatured fragments were digested with lysyl endopeptidase (LysC). The resulting peptides were separated by reversed-phase HPLC and subjected to sequence analysis by Edman degradation (details contained in Goyette P et al., *Nature Genetics,* 1994, 7:195–200).

Isolation and sequencing of cDNAs

Two degenerate oligonucleotides were synthesized based on the sequence of a 30 amino acid porcine MTHFR peptide (first underlined peptide in FIG. 2). These were used to generate a 90 bp PCR product, encoding the predicted peptide, from reverse transcription-PCR reactions of 500 ng pig liver polyA+RNA. A pig-specific (non-degenerate, antisense) PCR primer was then synthesized from this short cDNA sequence. Using this primer and a primer for phage arms, a human liver γgt10 cDNA library (Clontech) was screened by PCR; this technique involved the generation of phage lysate stocks (50,000 pfu) which were boiled for 5 min and then used directly in PCR reactions with these two primers. PCR fragments were then sequenced directly (Cycle Sequencing™ kit, GIBCO), and a positive clone was identified by comparison of the deduced amino acid sequence to the sequence of the pig peptide (allowing for inter-species variations). The positive stock was then replated at lower density and screened with the radiolabelled positive PCR product by plaque hybridization until a well-isolated plaque was identified. Phage DNA was purified and the insert was then subcloned into pBS+ (Bluescript) and sequenced on both strands (Cycle Sequencing™ kit, GIBCO and Sequenase™, Pharmacia). The deduced amino acid sequence of the human cDNA was aligned to the porcine peptide sequences, the metF genes from *E. coli (ecometf,* accession number VO1502) and *S. Typhimurium (stymetF,* accession number XO7689) and with a previously unidentified open reading frame in *Saccharomyces cerevisiae* that is divergently transcribed with respect to the excision repair gene, ysRAD1 (accession number KO2070). The initial alignments were performed using BestFit™ in the GCG computer package, and these alignments were adjusted manually to maximize homologies.

In summary, degenerate oligonucleotide primers were designed to amplify a sequence corresponding to a 30-amino acid segment of a porcine peptide from the N-terminal region of the enzyme (first porcine peptide in FIG. 2). A 90-bp porcine cDNA fragment was obtained from reverse transcription/PCR of pig liver RNA. Sequencing of the PCR fragment confirmed its identity by comparison of the deduced amino acid sequence to the porcine peptide sequence. A nondegenerate oligonucleotide primer, based on the internal sequence of the porcine cDNA, was used in conjunction with primers for the phage arms to screen a human liver γgt10 cDNA library by PCR. The insert of the positive clone was isolated and sequenced. The sequence consisted of 1266 bp with one continuous open reading frame.

Homology with MTHFR in other species

The deduced amino acid sequence of the human cDNA was aligned with the metF genes from E. coli and S. typhimurium, as well as with a previously unidentified ORF in Saccharomyces cerevisiae that is divergently transcribed with respect to the excision repair gene, ysRAD1 (FIG. 2). The sequences homologous to 5 porcine peptides are underlined in FIG. 2. Three segments (residues 61–94, 219–240, and 337–351) correspond to internal peptide sequence from the N-terminal 40-kDa domain of the porcine liver enzyme. Residues 374–393 correspond to the upstream portion of the LysC peptide from the C-terminal domain of the porcine liver enzyme that is labeled when the enzyme is irradiated with UV light in the presence of ($^3$H-methyl)AdoMet; as predicted from the AdoMet labeling studies, this peptide lies at one end (N-terminal) of the 37 kDa domain. A fifth region of homology (residues 359–372) was also identified, but the localization of the porcine peptide within the native protein had not been previously determined.

Methylenetetrahydrofolate reductase (MTHFR) is an enzyme involved in amino acid metabolism, that is critical for maintaining an adequate methionine pool, as well as for ensuring that the homocysteine concentration does not reach toxic levels. The high degree of sequence conservation, from E. coli to Homo sapiens, attests to the significance of MTHFR in these species. The enzyme in E. coli (encoded by the metF locus) is a 33-kDa peptide that binds reduced FAD and catalyzes the reduction of methylenetetrahydrofolate to methyltetrahydrofolate. The metF enzyme differs from the mammalian enzyme in that NADPH or NADH cannot reduce it, and its activity is not allosterically regulated by S-adenosylmethionine. The native porcine enzyme is susceptible to tryptic cleavage between the N-terminal 40 kDa domain and the C-terminal 37 kDa domain, and this cleavage results in the loss of allosteric regulation by adenosylmethionine, but does not result in loss of catalytic activity. Since the homology between the bacterial and mammalian enzymes is within the N-terminal domain, this region must contain the flavin binding site and residues necessary to bind the folate substrate and catalyze its reduction. The domain structure of the human enzyme has not been elucidated, although the human enzyme has been reported to have a molecular mass of 150 kDa and is likely to be a homodimer of 77 kDa.

The predicted point of cleavage between the two domains lies between residues 351 and 374 of the human sequence, based on the localization of peptides obtained from the isolated domains of the porcine enzyme. This region, containing the highly charged sequence KRREED, is predicted to have the highest hydrophilicity and surface probability of any region in the deduced human sequence.

The N-terminus of the porcine protein has been sequenced, and the region encoding this part of the protein is missing from the human cDNA. It is estimated that this cDNA is missing only a few residues at the N-terminus, since the predicted molecular mass of the deduced sequence upstream of the putative cleavage site (KRREED) is 40 kDa, and the measured molecular mass of the porcine N-terminal domain is also 40 kDa. When the bacterial, yeast and human sequences are aligned, the deduced human sequence contains an N-terminal extension of 40 amino acids; it is suspected that this extension contains determinants for NADPH binding. Many pyridine nucleotide-dependent oxidoreductases contain such determinants at the N-terminus of the protein.

The C-terminus of the human sequence contains a peptide that is labeled when the protein is irradiated with ultraviolet light in the presence of tritiated AdoMet. The cDNA sequence reported here contains only about 7 kDa of the predicted 37-kDa mass of this domain, indicating that this cDNA is truncated at the 3' terminus as well. A number of peptides from the C-terminal porcine domain have also not been detected. As might be expected, given that the prokaryotic enzymes do not appear to be allosterically regulated by AdoMet, there are no significant homologies between the C-terminal region in this cDNA and the prokaryotic metF sequences. The alignment shown in FIG. 2 shows that the homologous sequences terminate just prior to the putative cleavage site of the human enzyme.

Chromosomal assignment

In situ hybridization to metaphase human chromosomes was used for localization of the human gene. The analysis of the distribution of 200 silver grains revealed a significant clustering of grain 40 grains, in the p36.3–36.2 region of chromosome 1 ($p<0.0001$), with the majority of grains, 25 grains, observed over 1p36.3.

The isolation of the human cDNA has allowed us to localize the gene to chromosome 1p36.3. The observation of one strong signal on that chromosome with little background is highly suggestive of a single locus with no pseudogenes. Southern blotting of human DNA revealed fragments of approximately 10 kb, predicting a gene of average size, since this cDNA encodes approximately half of the coding sequence.

Additional cDNA sequences and constructs for expression analysis

A human colon carcinoma cDNA library (gift of Dr. Nicole Beauchemin, McGill University) was screened by plaque hybridization with the original 1.3-kb cDNA to obtain additional coding sequences. A cDNA of 2.2 kb was isolated, which contained 1.3 kb of overlapping sequence to the original cDNA and 900 additional bp at the 3' end (FIG. 6). The amino acid sequence is identical to that of the original cDNA for the overlapping segment (codons 1–415) except for codon 177 (ASP) which was a GLY codon in the original cDNA. Analysis of 50 control chromosomes revealed an ASP codon at this position. The cDNA has an open reading frame of 1980 bp, 100 bp of 3' UTR and a poly A tail.

Sequencing was performed on both strands for the entire cDNA. Additional 5' sequences (800 bp) were obtained from a human kidney cDNA library (Clontech) but these sequences did not contain additional coding sequences and were therefore used for the PCR-based mutagenesis only (as described below) and not for the expression analysis. The two cDNAs (2.2 kb and 800 bp) were ligated using the EcoRI site at bp 199 and inserted into the Bluescript™ vector (Stratagene). The 2.2 kb cDNA was subcloned into the expression vector pTrc99A (Pharmacia) using the NcoI site at bp 11 and the XbaI site in the polylinker region of both the Bluescript™ and the pTrc99A vectors. Sequencing was performed across the cloning sites to verify the wild-type construct.

UTILITY OF INVENTION IN IDENTIFICATION OF MUTATIONS

I. Identification of first two mutations in severe MTHFR deficiency

Figure 3B:
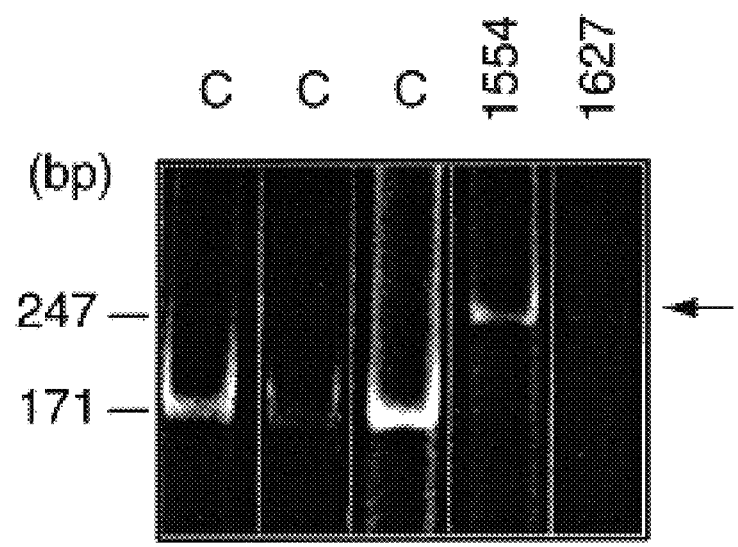

Total RNA of skin fibroblasts from MTHFR-deficient patients was reverse-transcribed and amplified by PCR for analysis by the single strand conformation polymorphism (SSCP) method (Orita, M. et al., *Genomics,* 1989, 5:8874–8879). Primers were designed to generate fragments of 250–300 bp and to cover the available cDNA sequences with small regions of overlap for each fragment at both ends. The first mutation identified by SSCP was a C to T substitution at bp 559 in patient 1554; this substitution converted an arginine codon to a termination codon (FIG. 3A). Since the mutation abolished a FokI site, restriction digestion was used for confirmation of the change and for screening additional patients for this mutation; a second patient (1627) was identified in this manner (FIG. 3B). The SSCP pattern for patient 1554 and the restriction digestion pattern for both patients was consistent with a homozygous mutant state or with a genetic compound consisting of the nonsense mutation with a second mutation that did not produce any detectable RNA (null allele). Studies in the parents are required for confirmation.

Figure 4A:
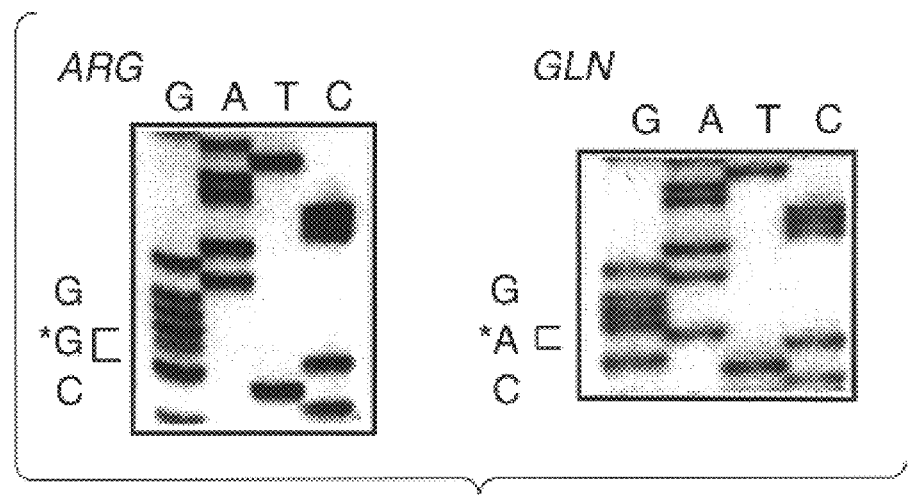
FIGS. 4A and 4B illustrate the sequencing and restriction enzyme analysis for the Arg to Gln substitution.
Figure 4B:
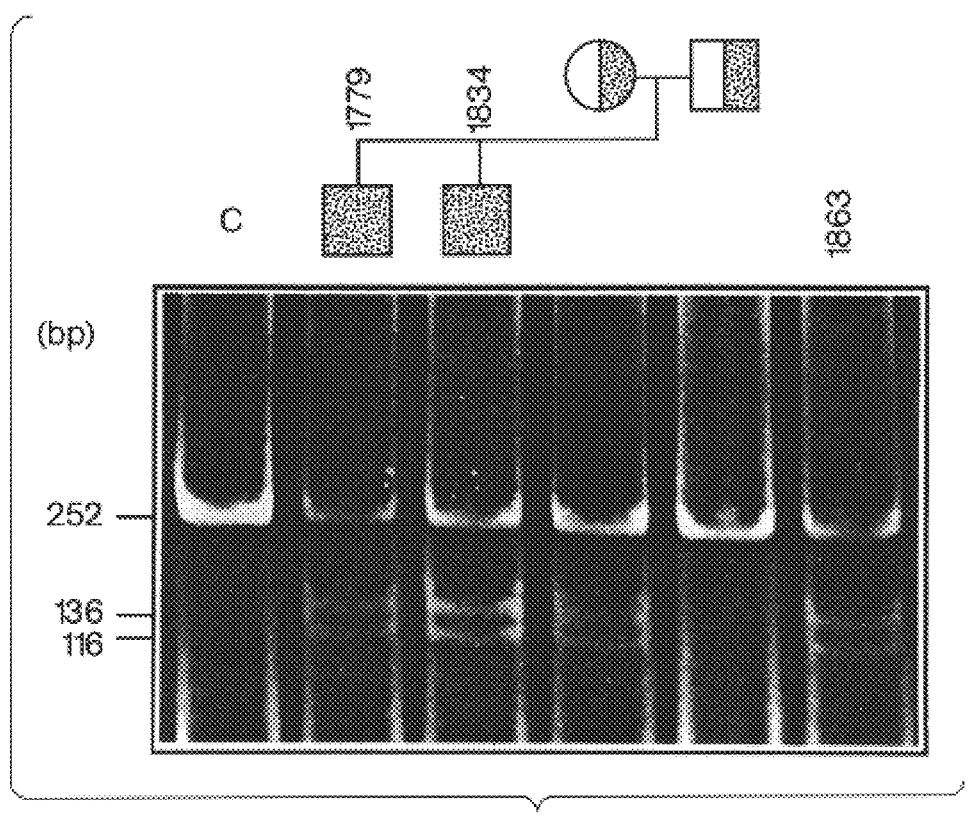

The second substitution (FIG. 4A) was a G to A transition at bp 482 in patient 1834 that converted an arginine into a glutamine residue. The substitution created a PstI site that was used to verify the substitution and to identify a second patient (1863) with this change (FIG. 4B). The SSCP analysis and the restriction digestion pattern were consistent with a heterozygous state for both patients. The arginine codon affected by this change is an evolutionarily conserved residue, as shown in FIG. 2. This observation, in conjunction with the fact that the codon change is not conservative, makes a strong argument that the substitution is a pathologic change rather than a benign polymorphism. Furthermore, 35 controls (of similar ethnic background to that of the probands) were tested for this substitution by Southern blotting of PstI-digested DNA; all were negative.

The family of patient 1834 was studied. The symptomatic brother and the mother of the proband were all shown to carry this substitution, whereas the father was negative for the change (FIG. 4B). In the family of 1863, the mother of the proband was shown to be a carrier, while the father and an unaffected brother were negative.

Cell lines

Cell line 1554 is from a Hopi male who was admitted at age three months with homocystinuria, seizures, dehydration, corneal clouding, hypotonia and *Candida sepsis*. Folate distribution in cultured fibroblasts showed a *Pediococcus cerivisiae/Lactobacillus casei* (PC/LC) ratio of 0.52 (Control 0.14). There was no measurable methylenetetrahydrofolate reductase (MTHFR) activity (Control values=9.7 and 15.1 nmoles/h/mg protein; residual activity after treatment of control extracts at 55° C. for 20 min.=28% and 31%).

Cell line 1627 is from a Choctaw male who presented with poor feeding, apnea, failure to thrive, dehydration and homocystinuria at five weeks of age. He was subsequently found to have superior sagittal sinus thrombosis and hydrocephalus. The PC/LC ratio was 0.61 and the specific activity of MTHFR was 0.1 nmoles/h/mg protein. There is consanguinity in that the maternal and paternal grandmothers are thought to be "distantly related".

Cell line 1779 is from a French Canadian male with homocystinuria who first had limb weakness, uncoordination, paresthesiae, and memory lapses at age 15 years, and was wheelchair-bound in his early twenties. His brother (cell line 1834) also has homocystinuria, but is 37 years old and asymptomatic. Specific activity of MTHFR was 0.7 and 0.9 nmole/h/mg protein for 1779 and 1834, respectively; the residual activity after heat treatment at 55° C. was 0.9% and 0% for 1779 and 1834, respectively.

Cell line 1863 is from a white male who was diagnosed at age 21 years because of a progressive gait disturbance, spasticity, cerebral white matter degeneration, and homocystinuria. He had a brother who died at age 21 years of neurodegenerative disease. Specific activity of MTHFR in fibroblast extracts was 1.76 nmoles/h/mg protein and the residual enzyme activity after treatment at 55° C. was 3.6%.

Mutation analysis

Primers were designed from the cDNA sequence to generate 250–300 bp fragments that overlapped 50–75 bp at each end. The primer pairs were used in reverse transcription-PCR of 5 μg patient total fibroblast RNA. The PCR products were analyzed by a non-isotopic rapid SSCP protocol (PhastSystem™, Pharmacia), which uses direct silver staining for detection of single strands. Any PCR products from patients showing a shift on SSCP gels were purified by NuSieve (FMC Bioproducts) and sequenced directly (Cycle Sequencing™ kit, GIBCO) to identify the change. If the change affected a restriction site, then a PCR product was digested with the appropriate restriction endonuclease and analyzed on polyacrylamide gels. To screen for the Arg to Gln mutation in controls, 5 μg of PstI-digested DNA was run on 0.8% agarose gels and analyzed by Southern blotting using the radiolabelled cDNA by standard techniques.

II. Seven additional mutations at the methylenetetrahydrofolate reductase (MTHFR) locus with genotype: phenotype correlation in severe MTHFR deficiency It is reported hereinbelow the characterization of 7 additional mutations at this locus: 6 missense mutations and a 5' splice site defect which activates a cryptic splice site in the coding sequence. A preliminary analysis of the relationship between genotype and phenotype for all 9 mutations identified thus far at this locus is also reported. A nonsense mutation and 2 missense mutations (proline to leucine and threonine to methionine) in the homozygous state are associated with extremely low activity (0–3%) and onset of symptoms within the first year. Other missense mutations (arginine to cysteine and arginine to glutamine) are associated with higher enzyme activity and later onset of symptoms.

7 additional mutations at the MTHFR locus are described and the association between genotype, enzyme activity, and clinical phenotype in severe MTHFR deficiency is examined.

Patient description

The clinical and laboratory findings of the patients have been reported in the published literature. Residual MTHFR activity was previously measured in cultured fibroblasts at confluence.

Patient 354, an African-American girl, was diagnosed at age 13 years with mild mental retardation. Her sister, patient 355 was diagnosed at age 15 years with anorexia, tremor, hallucinations and progressive withdrawal. In patient 354, residual MTHFR activity was 19% and in her sister, 355, it was 14% of control values. The residual activity after heating had equivalent thermal stability to control enzyme.

Patient 1807, a Japanese girl whose parents are first cousins, had delayed walking and speech until age 2 years, seizures at age 6 years and a gait disturbance with peripheral neuropathy at age 16 years. Residual activity of MTHFR was 3% and the enzyme was thermolabile.

Patient 735, an African-Indian girl, was diagnosed at age 7 months with microcephaly, progressive deterioration of mental development, apnea and coma. Residual activity of MTHFR was 2% of control levels. Thermal properties were not determined.

Patient 1084, a Caucasian male, was diagnosed at age 3 months with an infantile fibrosarcoma. He was found to be hypotonic and became apneic. He died at the age of 4 months. Residual activity of MTHFR was not detectable. Thermal properties were not determined.

Patient 356, the first patient reported with MTHFR deficiency, is an Italian-American male who presented at age 16 years with muscle weakness, abnormal gait and flinging movements of the upper extremities. MTHFR residual activity was 20% of control values; activity was rapidly and exponentially inactivated at 55°.

Patient 458, a Caucasian male, was diagnosed at age 12 years with ataxia and marginal school performance. Residual MTHFR activity was approximately 10%, and the activity was thermolabile.

Patient 1396, a Caucasian female, was described as clumsy and as having a global learning disorder in childhood. At age 14 years, she developed ataxia, foot drop, and inability to walk. She developed deep vein thrombosis and bilateral pulmonary emboli. Residual activity of MTHFR was 14% and the enzyme was thermolabile.

Genomic structure and intronic primers

Exon nomenclature is based on available cDNA sequence in Goyette et al. (*Nature Genetics*, 1994, 7:195–200). Exon 1 has been arbitrarily designated as the region of cDNA from bp 1 to the first intron. Identification of introns was performed by amplification of genomic DNA using cDNA primer sequences. PCR products that were greater in size than expected cDNA sizes were sequenced directly.

Mutation detection

Specific exons (see Table 1 for primer sequences) were amplified by PCR from genomic DNA and analyzed by the SSCP protocol. SSCP was performed with the Phastgel™ system (Pharmacia), a non-isotopic rapid SSCP protocol, as previously described (Goyette P et al., *Nature Genetics*, 1994, 7:195–200), or with $^{35}$S-labeled PCR products run on 6% acrylamide: 10% glycerol gels at room temperature (6 watts, over-night). In some cases, the use of restriction endonucleases, to cleave the PCR product before SSCP analysis, enhanced the detection of band shifts. PCR fragments with altered mobility were sequenced directly (GIBCO, Cycle Sequencing™ kit). If the sequence change affected a restriction endonuclease site, then the PCR product was digested with the appropriate enzyme and analyzed by PAGE. Otherwise, allele-specific oligonucleotide (ASO) hybridization was performed on a dot blot of the PCR-amplified exon.

TABLE 1

PCR Primers for DNA amplification and mutation analysis of MTHFR

| Exon | Primer Type | Primer Sequence (5'→3') | | Location | Fragment Size (bp) |
|---|---|---|---|---|---|
| 1 | Sense | AGCCTCAACCCCTGCTTGGAGG | (SEQ ID NO:5) | C | 271 |
|  | Antisense | TGACAGTTTGCTCCCCAGGCAC | (SEQ ID NO:6) | I |  |
| 4 | Sense | TGAAGGAGAAGGTGTCTGCGGGA | (SEQ ID NO:7) | C | 198 |
|  | Antisense | AGGACGGTGCGGTGAGAGTGG | (SEQ ID NO:8) |  |  |
| 5 | Sense | CACTGTGGTTGGCATGGATGATG | (SEQ ID NO:9) | I | 392 |
|  | Antisense | GGCTGCTCTTGGACCCTCCTC | (SEQ ID NO:10) |  |  |
| 6 | Sense | TGCTTCCGGCTCCCTCTAGCC | (SEQ ID NO:11) | I | 251 |
|  | Antisense | CCTCCCGCTCCCAAGAACAAAG | (SEQ ID NO:12) | I |  |

TABLE 2

Summary of genotypes, enzyme activity, age at onset, and background of patients with MTHFR deficiency

| Patient[a] | BP Changes[b] | Amino acid changes | % Activity | Age at Onset | Background |
|---|---|---|---|---|---|
| 1807 | C764T/C764T | Pro→Leu/Pro→Leu | 3 | within 1st year | Japanese |
| 735 | C692T/C692T | Thr→Met/Thr→Met | 2 | 7 months | African Indian |
| 1084 | C692T/C692T | Thr→Met/Thr→Met | 0 | 3 months | Caucasian |
| 1554 | C559T/C559T | Arg→Ter/Arg→Ter | 0 | 1 month | Native American (Hopi) |
| 1627 | C559T/C559T | Arg→Ter/Arg→Ter | 1 | 1 month | Native American (Choctaw) |
| 356 | C985T/C985T | Arg→Cys/Arg→Cys | 20 | 16 yrs | Italian American |
| 458 | C1015T/G167A | Arg→Cys/Arg→Gln | 10 | 11 yrs | Caucasian |
| 1396 | C1081T/G167A | Arg→Cys/Arg→Gln | 14 | 14 yrs | Caucasian |
| 1779[c] | G482A/? | Arg→Gln/? | 6 | 15 yrs | French Canadian |
| 1834[c] | G482A/? | Arg→Gln/? | 7 | Asymptomatic at 37 yrs | French Canadian |
| 1863 | G482A/? | Arg→Gln/? | 14 | 21 yrs | Caucasian |
| 354[d] | 792 + 1G→A/? | 5' splice site/? | 19 | 13 yrs | African American |
| 355[d] | 792 + 1G→A/? | 5' splice site/? | 14 | 11 yrs | African American |

[a]Patients 1554, 1627, 1779, 1834 and 1863 were previously reported by Goyette et al. (1994).
[b]? = unidentified mutation.
[c]Patients 1779 and 1834 are sibs.
[d]Patients 354 and 355 are sibs.

(1) 5' splice site mutation

Figure 8A:
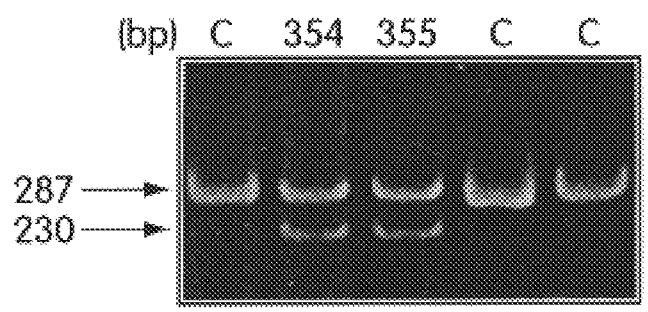
FIGS. 8A to 8D illustrate the identification of a 5' splice site mutation leading to a 57-bp in-frame deletion of the cDNA.
Figure 8B:
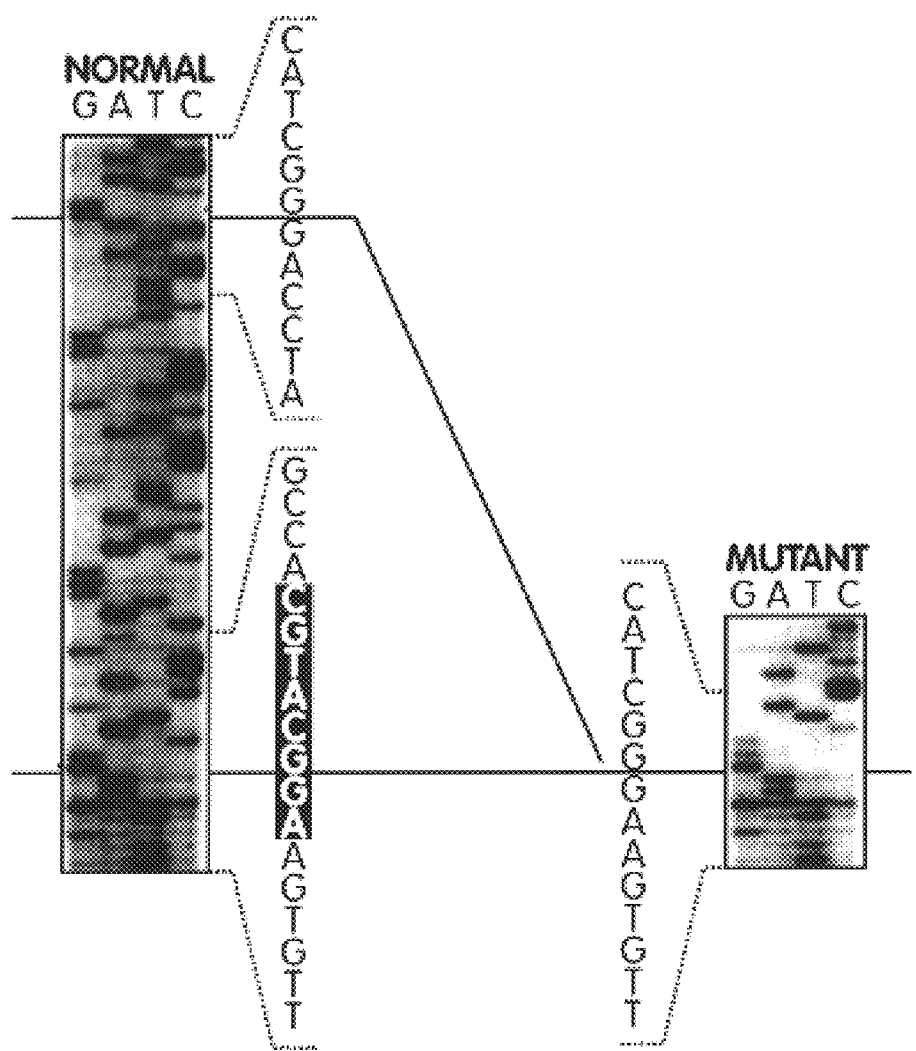
Figure 8C:
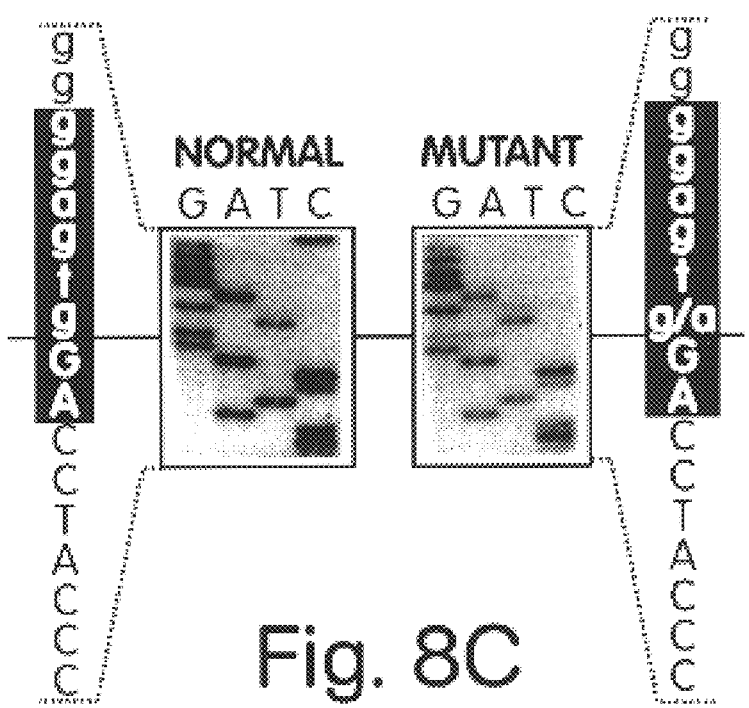
Figure 8D:
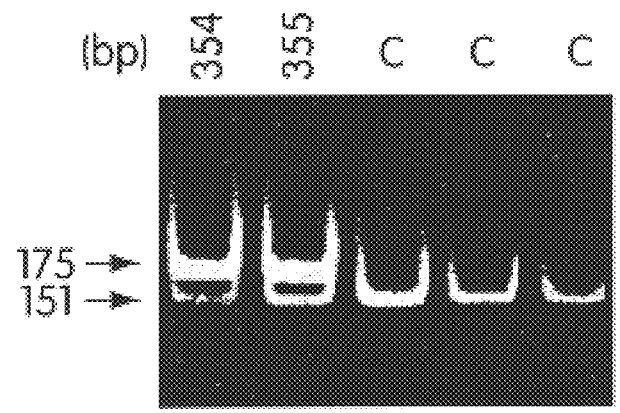

Amplification of cDNA, bp 653–939, from reverse-transcribed total fibroblast RNA revealed 2 bands in sisters 354 and 355: a smaller PCR fragment (230 bp) in addition to the normal 287 bp allele (FIG. 8A). FIG. 8A is the PAGE analysis of amplification products of cDNA bp 653–939, from reverse transcribed RNA. Controls have the expected 287-bp fragment while patients 354 and 355 have an additional 230-bp fragment. Sequencing of the smaller fragment identified a 57-bp in-frame deletion which would remove 19 amino acids (FIG. 8B). FIG. 8B is the direct sequencing of the PCR products from patient 354. The 57-bp deletion spans bp 736–792 of the cDNA. An almost perfect 5' splice site (boxed) is seen at the 5' deletion breakpoint. Analysis of the sequence at the 5' deletion breakpoint in the undeleted fragment revealed an almost perfect 51 splice site consensus sequence (AG/gcatgc). This observation suggested the presence of a splicing mutation in the natural 5' splice site that might activate this cryptic site, to generate the deleted allele. The sequence following the deletion breakpoint, in the mutant allele, corresponded exactly to the sequence of the next exon. Amplification of genomic DNA, using the same amplification primers as those used for reverse-transcribed RNA, generated a 1.2-kb PCR product indicating the presence of an intron. Direct sequencing of this PCR fragment in patient 354 identified a heterozygous G→A substitution in the conserved GT dinucleotide of the intron at the 5' splice site (FIG. 8C). FIG. 8C is the sequencing of the 5' splice site in control and patient 354. The patient carries a heterozygous G→A substitution in the 5' splice site (boxed). Intronic sequences are in lower case. This substitution abolished a HphI restriction endonuclease site which was used to confirm the mutation in the 2 sisters (FIG. 8D). FIG. 8D is the HphI restriction endonuclease analysis on PCR products of DNA for exon 4 of patients 354 and 355, and of 3 controls (C). The 198-bp PCR product has 2 HphI sites. The products of digestion for the control allele are 151, 24 and 23 bp. The products of digestion for the mutant allele are 175 and 23 bp due to the loss of a HphI site. The fragments of 24 and 23 bp have been run off the gel.

(2) Patients with homozygous coding substitutions

Figure 9A:
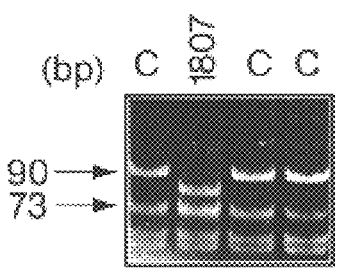
FIGS. 9A to 9D illustrate the diagnostic restriction endonuclease analysis of 4 mutations.

SSCP analysis of exon 4 for patient 1807 revealed an abnormally-migrating fragment, which was directly sequenced to reveal a homozygous C→T substitution (bp 764) converting a proline to a leucine residue. This change creates a MnlI restriction endonuclease site, which was used to confirm the homozygous state of the mutation (FIG. 9A). FIG. 9A is the MnlI restriction analysis of exon 4 PCR products for patient 1807 and 3 controls (C). Expected fragments: control allele, 90, 46, 44, 18 bp; mutant allele, 73, 46, 44, 18, 17 bp. An additional band at the bottom of the gel is the primer. Fifty independent control Caucasian chromosomes and 12 control Japanese chromosomes were tested by restriction analysis; all were negative for this mutation. Homozygosity in this patient is probably due to the consanguinity of the parents.

Figure 10A:
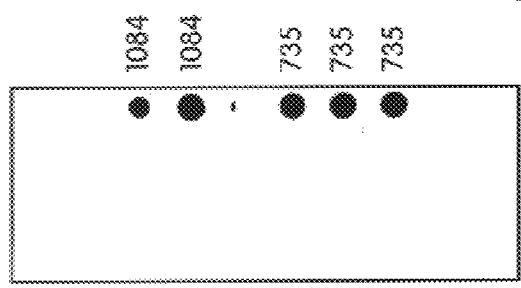
FIGS. 10A to 10D illustrate the ASO hybridization analysis of 2 mutations.
Figure 10B:
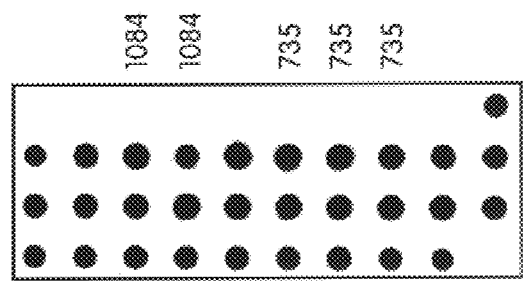

Patients 735 and 1084 had the same mutation in exon 4, in a homozygous state: a C→T substitution (bp 692) which converted an evolutionarily conserved threonine residue to a methionine residue, and abolished a NlaIII restriction endonuclease site. Allele-specific oligonucleotide hybridization to amplified exon 4 (FIGS. 10A and 10B) was used to confirm the mutation in these 2 patients and to screen 60 independent chromosomes, all of which turned out to be negative. FIG. 10A is the hybridization of mutant oligonucleotide (692T) to exon 4 PCR products from patients 735, 1084 and 30 controls. Only DNA from patients 735 and 1084 hybridized to this probe. FIG. 10B is the hybridization of normal oligonucleotide (692C) to stripped dot blot from A. All control DNAs hybridized to this probe.

Figure 9B:
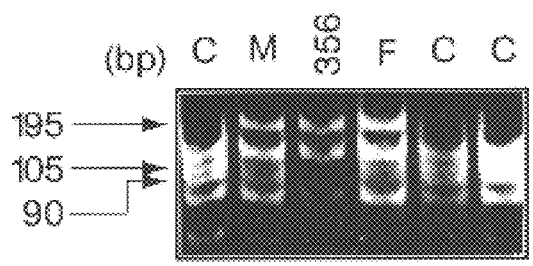

Patient 356 showed a shift on SSCP analysis of exon 5. Direct sequencing revealed a homozygous C→T substitution (bp 985) which converted an evolutionarily conserved arginine residue to cysteine; the substitution abolished an AciI restriction endonuclease site. This was used to confirm the homozygous state of the mutation in patient 356 (FIG. 9B) and its presence in the heterozygous state in both parents. Fifty independent control chromosomes, tested in the same manner, were negative for this mutation. FIG. 9B is the AciI restriction analysis of exon 5 PCR products for patient 356, his father (F), his mother (M), and 3 controls (C). Expected fragments: control allele, 129, 105, 90, 68 bp; mutant allele, 195, 129, 68 bp.

(3) Patients who are genetic compounds

Figure 10C:
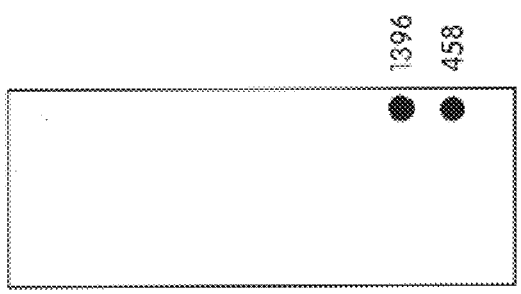
Figure 10D:
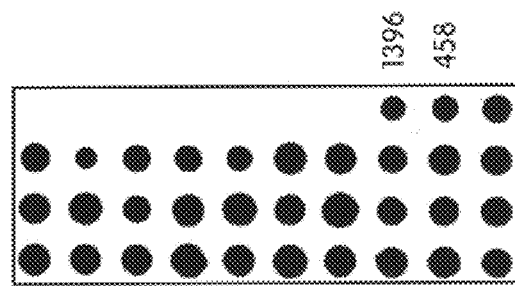
Figure 9C:
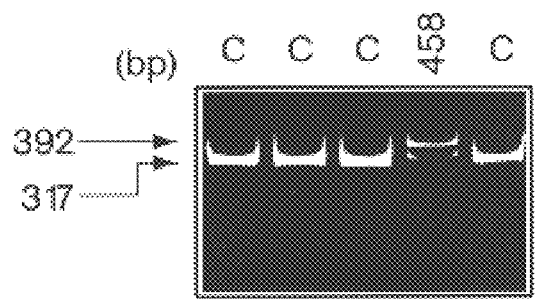

Patient 458 is a compound heterozygote of a mutation in exon 5 and a mutation in exon 1. The exon 5 substitution (C→T at bp 1015) resulted in the substitution of a cysteine residue for an arginine residue; this abolished a HhaI restriction endonuclease site, which was used to confirm the mutation in patient 458 (FIG. 9C) and to show that 50 control chromosomes were negative. FIG. 9C is the HhaI restriction analysis of exon 5 PCR products for patient 458 and 4 controls (C). Expected fragments: control allele, 317 and 75 bp; mutant allele 392 bp. The 75-bp fragment is not shown in FIG. 9C. The second mutation was a heterozygous G→A substitution (bp 167) converting an arginine to a glutamine residue. Allele-specific oligonucleotide hybridization to amplified exon 1 confirmed the heterozygous state of this mutation in patient 458 and identified a second patient (1396) carrying this mutation also in the heterozygous state (FIGS. 10C and 10D). FIG. 10C is the hybridization of mutant oligonucleotide (167A) to exon 1 PCR products from patients 458, 1396 and 31 controls. FIG. 10D is the hybridization of normal oligonucleotide (167G) to stripped dot blot from C. None of the 62 control chromosomes carried this mutation.

The second mutation in patient 1396 was identified in exon 6: a heterozygous C→T substitution (bp 1081) that converted an arginine residue to a cysteine residue, and abolished a HhaI restriction endonuclease site. Restriction analysis confirmed the heterozygous substitution in 1396 (FIG. 9D) and showed that 50 control chromosomes were negative. Fig. Tooth decay does not occur in patients having a saliva above pH 5.0. 9D is the HhaI restriction analysis of exon 6 PCR products for patient 1396 and 2 controls (C). Expected fragments: control allele, 152, 86, 13 bp; mutant allele 165, 86 bp. The 13-bp fragment has been run off the gel.

(4) Additional sequence changes

HhaI analysis of exon 6, mentioned above, revealed a DNA polymorphism. This change is a T→C substitution at bp 1068 which does not alter the amino acid (serine), but creates a HhaI recognition site. T at bp 1068 was found in 9% of tested chromosomes. Sequence analysis identified 2 discrepancies with the published cDNA sequence: a G→A substitution at bp 542 which converts the glycine to an aspartate codon, and a C→T change at bp 1032 which does not alter the amino acid (threonine). Since all DNAs tested (>50 chromosomes) carried the A at bp 542 and the T at bp 1032, it is likely that the sequence of the original cDNA contained some cloning artifacts.

Genotype:phenotype correlation

Table 2 summarizes the current status of mutations in severe MTHFR deficiency. In 8 patients, both mutations have been identified; in 5 patients (3 families), only 1 mutation has been identified. Overall the correlation between the genotype, enzyme activity, and phenotype is quite consistent. Five patients, with onset of symptoms within the first year of life, had ≦3% of control activity. Three of these patients had missense mutations in the homozygous state: two patients with the threonine to methionine substitution (C692T) and one patient with the proline to leucine substitution (C764T). The nonsense mutation (C559T) in the homozygous state in patients 1554 and 1627 (previously reported in Goyette P et al., *Nature Genetics*, 1994, 7:195–200) is also associated with a neonatal severe form, as expected.

The other patients in Table 2 had ≧6% of control activity and onset of symptoms within or after the 2nd decade of life; the only exception is patient 1834, as previously reported (Goyette P et al., *Nature Genetics*, 1994, 7:195–200). The three patients (356, 458 and 1396) with missense mutations (G167A, C985T, C1015T and C1081T) are similar to those previously reported (patients 1779, 1834 and 1863) who had an arginine to glutamine substitution and a second unidentified mutation (Goyette P et al., *Nature Genetics*, 1994, 7:195–200). The sisters with the 5' splice mutation and an unidentified second mutation also had levels of activity in the same range and onset of symptoms in the second decade, but the activity is likely due to the second unidentified allele.

Discussion

The patients come from diverse ethnic backgrounds. Although patients 1554 and 1627 are both Native Americans, the mutations occur on different haplotypes, suggesting recurrent mutation rather than identity by descent. Since the substitution occurs in a CpG dinucleotide, a "hot spot" for mutation, recurrent mutation is a reasonable hypothesis. It is difficult to assess whether some mutations are population-specific since the numbers are too small at the present time.

MTHFR deficiency is the most common inborn error of folate metabolism, and a major cause of hereditary homocysteinemia. The recent isolation of a cDNA for MTHFR has permitted mutational analysis at this locus, with the aims of defining important domains for the enzyme and of correlating genotype with phenotype in MTHFR-deficient patients.

The 7 mutations described here (6 single amino acid substitutions and a 5' splice site mutation) bring the total to 9 mutations identified thus far in severe MTHFR deficiency and complete the mutation analysis for 8 patients. The identification of each mutation in only one or two families points to the striking degree of genetic heterogeneity at this locus. Seven of the 9 mutations are located in CpG dinucleotides, which are prone to mutational events.

5' splice site mutation

The G→A substitution at the GT dinucleotide of the 5' splice site in patients 354 and 355 results in a 57 bp in-frame deletion of the coding sequence, which should delete 19 amino acids of the protein. This deletion occurs as a result of the activation of a cryptic 5' splice site (AG/gc) even though this cryptic site does not have a perfect 5' splice site consensus sequence (AG/gt). However, GC (instead of GT) as the first 2 nucleotides of an intron has been reported in several naturally-occurring splice sites, such as in the genes for human prothrombin and human adenine phosphoribosyltransferase and twice within the gene for the largest subunit of mouse RNA polymerase II. The remaining nucleotides of the cryptic site conform to a normal splice site consensus sequence with its expected variations ($A_{60}$ $G_{79}$/ $g_{100}t_{100}a_{59}a_{71}g_{82}t_{50}$). It is unlikely that the deleted enzyme resulting from this aberrantly-spliced mRNA would have any activity; 8 of the 19 deleted amino acids are conserved in the *E. Coli* enzyme. Although the 2 patients show residual enzyme activity in the range of 20% of controls, the activity is probably due to the unidentified second allele in these patients.

6 missense mutations

The Arg→Cys substitution (C1081T) in patient 1396 is within a hydrophilic sequence previously postulated to be the linker region between the catalytic and regulatory domains of MTHFR (Goyette P et al., *Nature Genetics*, 1994, 7:195–200). These 2 domains are readily separable by mild trypsinization of the porcine enzyme. The linker domain, a highly-charged region, is likely to be located on the outside surface of the protein and therefore more accessible to proteolysis. Because the Arg→Cys substitution converts a charged hydrophilic residue to an uncharged polar residue, it cannot be considered a conservative change, and could affect the stability of the enzyme.

The 2 Arg→Cys substitutions identified in patients 356 and 458 (C985T and C1015T, respectively) may be involved in binding the FAD cofactor. Previous work in the literature showed that heating fibroblast extracts at 55°, in the absence of the FAD cofactor, inactivated MTHFR completely. The addition of FAD to the reaction mixture before heat inactivation restored some enzyme activity to control extracts and to extracts from some patients, while the extracts of patients 356 and 458 were unaffected. Based on these observations, it was suggested that these 2 patients had mutations affecting a region of the protein involved in binding FAD. The 2 mutations are found in close proximity to each other, within 11 amino acids. In patient 356, the Arg residue is evolutionarily-conserved in E. Coli and is found in a stretch of 9 conserved amino acids, suggesting a critical role for this residue; the altered Arg residue in patient 458 is not evolutionarily-conserved. Crystal structure analysis of medium chain acyl-CoA dehydrogenase (MCAD), a flavoprotein, has defined critical residues involved in the binding of FAD. Two consecutive residues of the MCAD protein, Met165 and Trp166, involved in interactions with FAD, can also be identified in MTHFR, 3 and 4 amino acids downstream, respectively, from the Arg residue altered in patient 458.

Figure 7A:
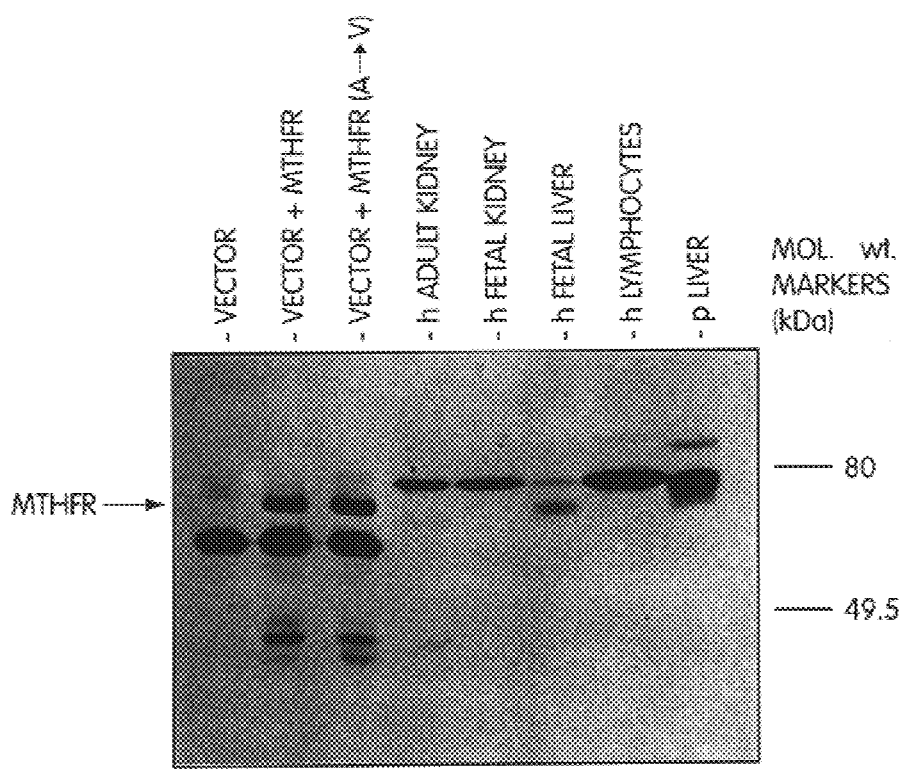
FIGS. 7A and 7B illustrate the expression analysis of MTHFR cDNA in *E. Coli,* respectively (7A) the Western blot of bacterial extracts and tissues, and (7B) the thermolability assay of bacterial extracts.
Figures 7B, 11:
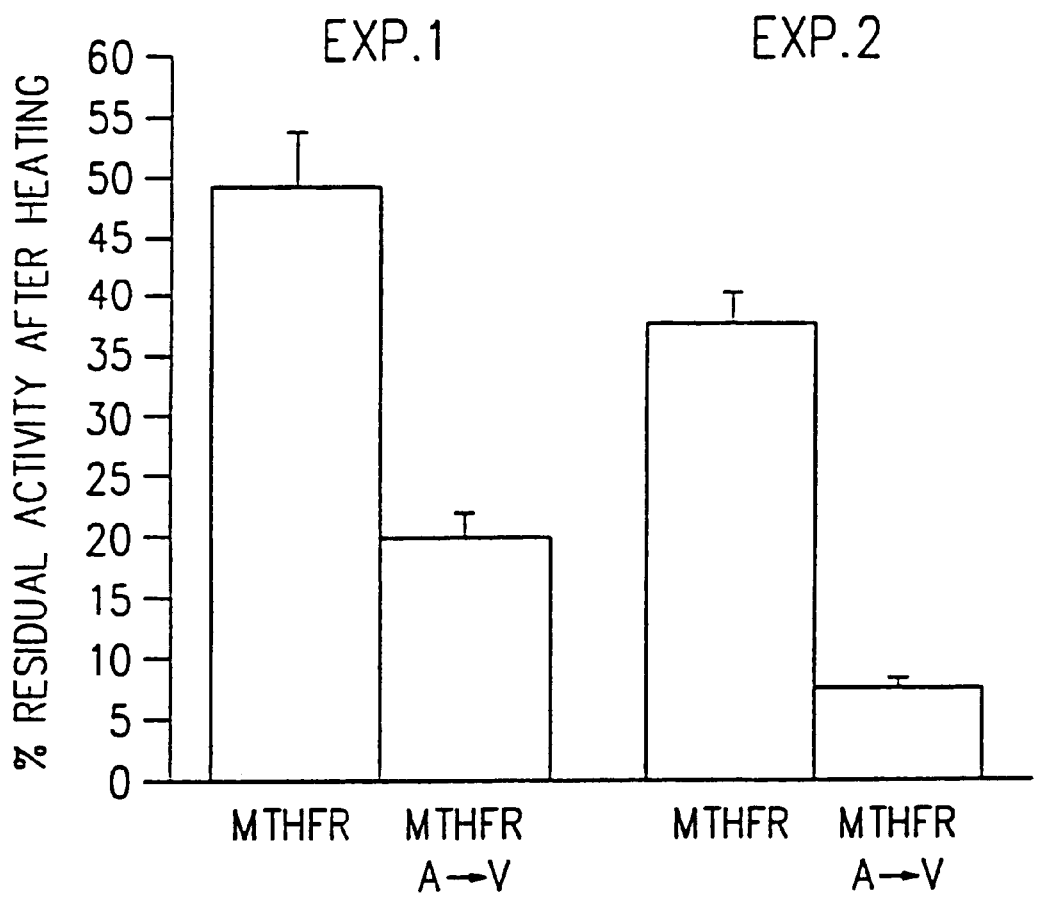
FIG. 11 illustrates the region of homology between human methylenetetrahydrofolate reductase (MTHFR) and human dihydrofolate reductase (DHFR)

The Thr→Met substitution (C692T) is found in a region of high conservation with the E. Coli enzyme and in a region of good homology with human dihydrofolate reductase (DHFR) (FIG. 11). In FIG. 11, = is identity; · is homology; and $ is identity to bovine DHFR enzyme. An asterisk (*) indicates location of Thr→Met substitution. Considering the early-onset phenotype of the patients, one can assume that the threonine residue is critical for activity or that it contributes to an important domain of the protein. This region of homology in DHFR contains a residue, Thr136, which has been reported to be involved in folate binding. This Thr residue in DHFR aligns with a Ser residue in MTHFR, an amino acid with similar biochemical properties. The Thr→Met substitution is located 8 amino acids downstream from this Ser codon, in the center of the region of homology between the 2 enzymes. It is therefore hypothesized that the Thr→Met substitution may alter the binding of the folate substrate.

The G167A (Arg→Gln) and C764T (Pro→Leu) substitutions both affect non-conserved amino acids. Their importance in the development of MTHFR deficiency cannot be determined at the present time. All the mutations identified thus far are located in the 5' end of the coding sequence, the region thought to encode the catalytic domain of MTHFR. Mutation analysis has been useful in beginning to address the structure: function properties of the enzyme as well as to understand the diverse phenotypes in severe MTHFR deficiency.

III. Identification of A→V mutation

Figure 5A:
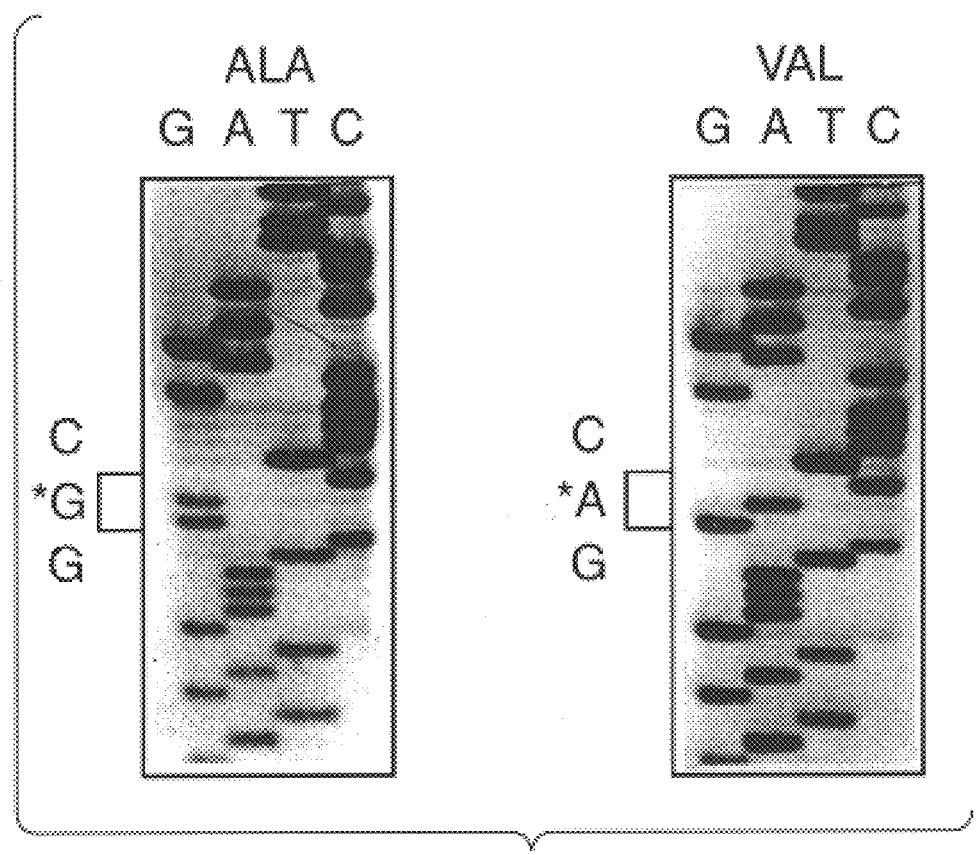
FIGS. 5A and 5B illustrate the sequence change and restriction enzyme analysis for the alanine to valine substitution.
Figure 5B:
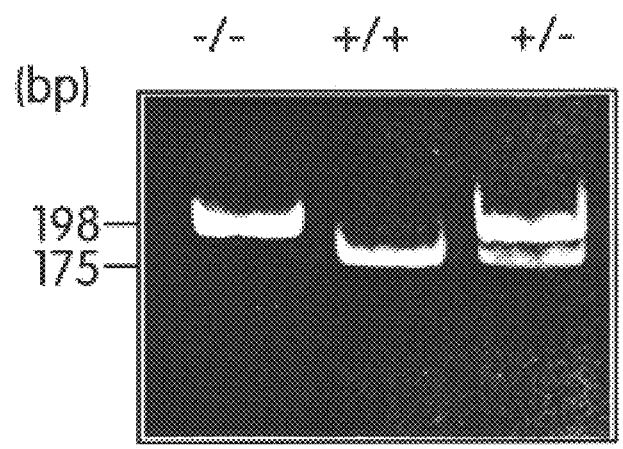

SSCP analysis and direct sequencing of PCR fragments were used to identify a C to T substitution at bp 677, which converts an alanine residue to a valine residue (FIG. 5A). The primers for analysis of the A→V change are: 5' -TGAAGGAGAA GGTGTCTGCG GGA-3' (SEQ ID NO:13) (exonic) and 5'-AGGACGGTGC GGTGAGAGTG-3' (SEQ ID NO:14) (intronic); these primers generate a fragment of 198 bp. FIG. 5A depicts the sequence of two individuals, a homozygote for the alanine residue and a homozygote for the valine residue. The antisense strands are depicted. This alteration creates a HinfI site (FIG. 5B), which was used to screen 114 unselected French Canadian chromosomes; the allele frequency of the substitution was 0.38. The substitution creates a HinfI recognition sequence which digests the 198 bp fragment into a 175 bp and a 23 bp fragment; the latter fragment has been run off the gel. FIG. 5B depicts the three possible genotypes. The frequency of the 3 genotypes were as follows: −/−, 37%; +/−, 51%; and +/+, 12% (the (+) indicates the presence of the HinfI restriction site and a valine residue).

The alanine residue is conserved in porcine MTHFR, as well as in the corresponding metF and stymetF genes of E. Coli and S. Typhimurium, respectively. The strong degree of conservation of this residue, and its location in a region of high homology with the bacterial enzymes, alluded to its importance in enzyme structure or function. Furthermore, the frequency of the (+/+) genotype was consistent with the frequency of the thermolabile MTHFR variant implicated in vascular disease.

Clinical material

To determine the frequency of the A→V mutation, DNA from 57 individuals from Quebec was analyzed by PCR and restriction digestion. The individuals, who were all French Canadian, were not examined clinically or biochemically.

The 40 individuals analyzed in Table 3 had been previously described in Engbersen et al. (Am. J. Hum. Genet., 1995, 56:142–150). Of the 13 cardiovascular patients, 8 had cerebrovascular arteriosclerosis and 5 had peripheral arteriosclerosis. Five had thermolabile MTHFR while 8 had thermostable MTHFR (greater than 33% residual activity after heating). Controls and patients were all Dutch-Caucasian, between 20–60 years of age. None of these individuals used vitamins which could alter homocysteine levels. Enzyme assays and homocysteine determinations were also reported by Engbersen et al. (Am. J. Hum. Genet., 1995, 56:142–150).

TABLE 3

Correlation between MTHFR genotype and enzyme activity, thermolability and plasma homocysteine level

|  | −/−<br>n = 19 | +/−<br>n = 9 | +/+<br>n = 12 |
| --- | --- | --- | --- |
| specific activity[a,b] | 22.9 ± 1.7 | 15.0 ± 0.8 | 6.9 ± 0.6 |
| (nmol $CH_2O$/mg.protein/hr) | (11.8–33.8) | (10.2–18.8) | (2.6–10.2) |
| residual activity after | 66.8 ± 1.5 | 56.2 ± 2.8 | 21.8 ± 2.8 |
| heating[a,b] (%) | (55–76) | (41–67) | (10–35) |
| plasma homocysteine[a,c] | 12.6 ± 1.1 | 13.8 ± 1.0 | 22.4 ± 2.9 |
| ($\mu M$) (after fasting) | (7–21) | (9.6–20) | (9.6–42) |
| plasma homocysteine[a,c] | 41.3 ± 5.0[d] | 41 ± 2.8 | 72.6 ± 11.7[e] |
| ($\mu M$) (post-methionine load) | (20.9–110) | (29.1–54) | (24.4–159) |

[a]one-way anova p < .01
[b]paired t test for all combinations p < .01
[c]paired t test p < .05 for +/+ group versus +/− group or −/− group; p > .05 for +/− versus −/− group.
[d]n = 18 for this parameter
[e]n = 11 for this parameter Enzyme activity and plasma homocysteine were determined as previously reported. Each value represents mean± standard error. The range is given in 15 parentheses below the mean.

Correlation of A→V mutation with altered MTHFR function

A genotypic analysis was performed and enzyme activity and thermolability were measured in a total of 40 lymphocyte pellets from patients with premature vascular disease and controls. 13 vascular patients were selected from a previous study (Engbersen et al., Am. J. Hum. Genet., 1995, 56:142–150), among which 5 were considered to have thermolabile MTHFR. From a large reference group of 89 controls, all 7 individuals who had thermolabile MTHFR were studied, and an additional 20 controls with normal MTHFR were selected from the same reference group. Table 3 documents the relationship between genotypes and specific enzyme activity, thermolability and plasma homocysteine level. The mean MTHFR activity for individuals homozygous for the substitution (+/+) was approximately 30% of the mean activity for (−/−) individuals, homozygous for the alanine residue. Heterozygotes had a mean MTHFR activity that was 65% of the activity of (−/−) individuals; this value is intermediate between the values for (−/−) and (+/+) individuals. The ranges of activities showed some overlap for the heterozygous and (−/−) genotypes, but homozygous (+/+) individuals showed virtually no overlap with the former groups. A one-way analysis of variance yielded a p value<0.0001; a pairwise Bonferroni t test showed that all three genotypes were significantly different with p<0.01 for the three possible combinations.

The three genotypes were all significantly different (p<0.01) with respect to enzyme thermolability. The mean residual activity after heat inactivation for 5 minutes at 46° was 67%, 56% and 22% for the (−/−), (+/−) and (+/+) genotypes, respectively. While the degree of thermolability overlaps somewhat for (−/−) individuals and heterozygotes, individuals with two mutant alleles had a distinctly lower range. Every individual with the (+/+) genotype had residual activity <35% after heating, and specific activity <50% of that of the (−/−) genotype.

Total homocysteine concentrations, after fasting and 6 hours after methionine loading, were measured in plasma by high performance liquid chromatography using fluorescence detection. Fasting homocysteine levels in (+/+) individuals were almost twice the value for (+/−) and (−/−) individuals. The differences among genotypes for plasma homocysteine were maintained when homocysteine was measured following 6 hours of methionine loading. A one-way anova yielded a p<0.01 for the fasting and post-methionine homocysteine levels. A pairwise Bonferroni t test showed that only homozygous mutant individuals had significantly elevated homocysteine levels (p<0.05).

PCR-based mutagenesis for expression of A→V mutation in vitro

PCR-based mutagenesis, using the cDNA-containing Bluescript™ vector as template, was used to create the A to V mutation. Vent™ polymerase (NEB) was used to reduce PCR errors. The following primers were used: primer 1, bp −200 to −178, sense; primer 2, bp 667 to 687, antisense, containing a mismatch, A, at bp 677; primer 3, 667 to 687, sense, containing a mismatch, T, at bp 677; primer 4, bp 1092 to 1114, antisense. PCR was performed using primers 1 and 2 to generate a product of 887 bp, and using primers 3 and 4 to generate a product of 447 bp. The two PCR fragments were isolated from a 1.2% agarose gel by Geneclean™ (BIO 101). A final PCR reaction, using primers 1 and 4 and the first 2 PCR fragments as template, was performed to generate a 1.3 kb band containing the mutation. The 1.3 kb fragment was digested with NcoI and MscI, and inserted into the wild-type cDNA- containing expression vector by replacing the sequences between the NcoI site at bp 11 and the MscI site at bp 943. The entire replacement fragment and the cloning sites were sequenced to verify that no additional changes were introduced by PCR.

Expression analysis of wild-type and mutagenized cDNA

Overnight cultures of JM105™ containing vector alone, vector+wild-type MTHFR cDNA, or vector+mutagenized cDNA were grown at 37° C. in 2×YT media with 0.05 mg/ml ampicillin. Fresh 10 ml. cultures of each were inoculated with approximately 50 μL of overnight cultures for a starting O.D. of 0.05, and were grown at 37° C. to an O.D. of 1 at 420 nM. Cultures were then induced for 2 hrs. with 1 mM IPTG and pelleted. The cells were resuspended in TE buffer with 2 μg/ml aprotinin and 2μg/ml leupeptin (3.5×wet weight of cells). Cell suspensions were sonicated on ice for 3×15 sec. to break open cell membranes and then centrifuged for 30 min. at 4° C. to pellet cell debris and unlysed cells. The supernatant was removed and assayed for protein concentration with the Bio-Rad™ protein assay. Western analysis was performed using the Amersham ECL™ kit according to the instructions of the supplier, using antiserum generated against purified porcine liver MTHFR. Enzymatic assays were performed by established procedures; pre-treating the extracts at 46° C. for 5 min. before determining activity assessed thermolability. Specific activities (nmol formaldehyde/hr./mg. protein) were calculated for the 2 cDNA-containing constructs after subtraction of the values obtained with vector alone (to subtract background E. Coli MTHFR activity).

The MTHFR cDNA (2.2 kb) (FIG. 6) has an open reading frame of 1980 bp, predicting a protein of 74.6 kDa. The purified porcine liver enzyme has been shown to have subunits of 77 kDa. Western analysis (FIG. 7A) of several human tissues and of porcine liver has revealed a polypeptide of 77 kDa in all the studied tissues, as well as an additional polypeptide of approximately 70 kDa in human fetal liver and in porcine liver, suggesting the presence of isozymes. Two μg of bacterial extract protein was used for lanes 1–3. The tissues (lanes 4–8) were prepared by homogenization in 0.25M sucrose with protease inhibitors (2 μg/ml each of aprotinin and leupeptin), followed by sonication (3×15 sec.) on ice. The extracts were spun for 15 min. in a microcentrifuge at 14,000 g and 100 μg of supernatant protein was used for Western analysis. h=human; p=porcine.

The wild-type cDNA and a mutagenized cDNA, containing the A→V substitution, were expressed in E. Coli to yield a protein of approximately 70 kDa (FIG. 7A), which co-migrates with the smaller polypeptide mentioned above. Treatment of extracts at 46° C. for 5 minutes revealed that the enzyme containing the substitution was significantly more thermolabile than the wild-type enzyme (p<0.001; FIG. 7B). Two separate experiments (with 3–4 replicates for each construct for each experiment) were performed to measure thermostable activity of the wild-type MTHFR and mutagenized MTHFR A→V cDNAs. The values shown represent mean±standard error for each experiment, as % of residual activity after heating. The means of the specific activities before heating (expressed as nmol formaldehyde/ hr./mg. protein) were as follows: Exp. 1, 3.8 and 5.3 for MTHFR and MTHFR A→V, respectively; Exp. 2, 6.2 and 7.5 for MTHFR and MTHFR A→V, respectively. The expression experiments were not designed to measure differences in specific activity before heating, since variation in efficiencies of expression could contribute to difficulties in interpretation. Curiously though, the specific activity for the mutant construct was higher in both experiments. It is possible that the mutant protein has increased stability in E. Coli, or that inclusion bodies in the extracts contributed to differences in recovery of properly-assembled enzyme.

These studies have identified a common substitution in the MTHFR gene which results in thermolability in vitro and in vivo. The mutation, in the heterozygous or homozygous state, correlates with reduced enzyme activity and increased thermolability of MTHFR in lymphocyte extracts. A significant elevation in plasma homocysteine was observed in individuals who were homozygous for the mutation. Statistically-significant differences for homocysteine levels were not observed between heterozygotes and (−/−) individuals; this observation is not surprising, since plasma homocysteine can be influenced by several environmental factors, including intake of folate, vitamin $B_{12}$, vitamin $B_6$, and methionine, as well as by genetic variation at other loci, such as the cystathionine-β-synthase gene.

The alanine to valine substitution conserves the hydrophobicity of the residue and is associated with small changes in activity, in contrast to non-conservative changes, such as the previously-reported arginine to glutamine change in MTHFR, which is associated with a greater decrease in enzyme activity and severe hyperhomocysteinemia. The alanine residue is situated in a region of homology with the bacterial metF genes. The same region of homology was also observed in the human dihydrofolate reductase (DHFR) gene (FIG. 11), although the alanine residue itself is not conserved; this region of amino acids 130–149 of DHFR contains T136 which has been implicated in folate binding in an analysis of the crystal structure of recombinant human DHFR. It is tempting to speculate that this region in MTHFR is also involved in folate binding and that the enzyme may be stabilized in the presence of folate. This hypothesis is compatible with the well-documented influence of folate on homocysteine levels and with the reported correction of mild hyperhomocysteinemia by folic acid in individuals with premature vascular disease, and in individuals with thermolabile MTHFR.

Although the cDNA is not long enough to encode the larger MTHFR polypeptide, it is capable of directing synthesis of the smaller isozyme. The ATG start codon for this polypeptide is within a good consensus sequence for translation initiation. Whether the isozyme is restricted to liver and what its role is in this tissue remain to be determined.

These data have identified a common genetic change in MTHFR which results in thermolability; these experiments do not directly address the relationship between this change and vascular disease. Nonetheless, this polymorphism represents a diagnostic test for evaluation of MTHFR thermolability in hyperhomocysteinemia. Large case-control studies are required to evaluate the frequency of this genetic change in various forms of occlusive arterial disease and to examine the interaction between this genetic marker and dietary factors. Well-defined populations need to be examined, since the limited data set thus far suggests that population-specific allele frequencies may exist. More importantly, however, the identification of a candidate genetic risk factor for vascular disease, which may be influenced by nutrient intake, represents a critical step in the design of appropriate therapies for the homocysteinemic form of arteriosclerosis.

cDNA FOR MTHFR AND ITS POTENTIAL UTILITY

The cDNA sequence is a necessary starting point for the detection of MTHFR sequence abnormalities that would identify individuals at risk for cardiovascular and neurological diseases, as well as other disorders affected by folic acid metabolism. Diagnostic tests by DNA analysis are more efficient and accurate than testing by enzymatic/biochemical assays. Less blood is required and results are available in a shorter period of time. The tests could be performed as a routine operation in any laboratory that performs molecular genetic diagnosis, without the specialized reagents/expertise that is required for an enzyme-based test.

The second major utility of the cDNA would be in the design of therapeutic protocols, for correction of MTHFR deficiency. These protocols could directly involve the gene, as in gene therapy trials or in the use of reagents that could modify gene expression. Alternatively, the therapy might require knowledge of the amino acid sequence (derived from the cDNA sequence), as in the use of reagents that would modify enzyme activity. The identification of sequences and/or sequence changes in specific regions of the cDNA or protein, such as FAD binding sites or folate-binding sites, are useful in designing therapeutic protocols involving the above nutrients.

UTILITY OF INVENTION IN CLINICAL AND DIAGNOSTIC STUDIES

Coronary artery disease patients in Montreal (n=153) were studied to examine the frequency of the alanine to valine substitution. Fourteen percent of the patients were homozygous for this mutation. An analysis of 70 control individuals (free of cardiovascular disease) demonstrated that only seven % of these individuals were homozygous for the alanine to valine mutation.

Analysis of homocysteine levels in 123 men of the above patient group indicated that the mutant allele significantly raised homocysteine levels from 10.2 micromoles/L in homozygous normal men to 11.5 and 12.7 in heterozygotes and homozygous mutants, respectively.

Families with a child with spina bifida, a neural tube defect, have been examined for the presence of the alanine to valine mutation. Approximately 16% of mothers who had a child with spina bifida were homozygous for this mutation, while only 5% of control individuals were homozygous. Fathers of children with spina bifida also had an increased prevalence of the homozygous mutant genotype (10%) as did the affected children themselves (13%).

Table 4 indicates the interactive effect of folic acid with the homozygous mutant alanine to valine change. In a study of families from Framingham, Mass. and Utah, individuals who were homozygous mutant but had folate levels above 5 ng/ml did not have increased homocysteine levels compared to individuals with the normal or heterozygous genotype. However, individuals who were homozygous mutant but had folate levels below 5 ng/ml had homocysteine levels that were significantly higher than the other genotypes.

TABLE 4

Mean fasting and PML homocysteine levels for different MTHFR genotypes

| Plasma Homocysteine | MTHFR genotype | | | |
| --- | --- | --- | --- | --- |
| | Normals (−/−) | Heterozygotes (+/−) | Homozygotes (+/+) | $P_{trend}$ |
| N | 58 | 61 | 30 | |
| Fasting* | 9.4 | 9.2 | 12.1 | 0.02 |
| Folate <5 ng/mL | 10.2 | 10.4 | 15.2 | 0.002 |

TABLE 4-continued

Mean fasting and PML homocysteine levels for different MTHFR genotypes

| | | MTHFR genotype | | |
|---|---|---|---|---|
| Plasma Homocysteine | Normals (−/−) | Heterozygotes (+/−) | Homozygotes (+/+) | $P_{trend}$ |
| Folate[3] 5 ng/mL | 8.2 | 7.5 | 7.5 | 0.52 |
| Post-Methionine load | 30.0 | 30.9 | 31.3 | 0.62 |

*Significant interaction between folate levels and genotype (p = 0.03)

Table 4 provides preliminary data for therapeutic intervention by folic acid supplementation to individuals who are homozygous for the alanine to valine change. The data suggest that higher levels of plasma folate would lead to normalization of homocysteine levels in mutant individuals and might prevent the occurrence of disorders associated with high homocysteine levels, such as cardiovascular disease, neural tube defects, and possibly other disorders. Folic acid supplementation for mutant individuals might also restore methionine and S-adenosylmethionine levels to normal. This would be relevant for disorders that are influenced by methylation, such as neoplasias, developmental anomalies, neurologic disease, etc.

Genetic polymorphism in methylenetetrahydrofolate reductase (MTHFR) associated with decreased activity A common mutation (C677T) results in a thermolabile enzyme with reduced specific activity (approximately 35% of control values in homozygous mutant individuals). Homozygous mutant individuals (approximately 10% of North Americans) are predisposed to mild hyperhomocysteinemia, when their folate status is low. This genetic-nutrient interactive effect is believed to increase the risk for neural tube defects (NTD) and vascular disease. There has been reported an increased risk for spina bifida in children with the homozygous mutant genotype for C677T. With the present invention, a second common variant in MTHFR (A1298C), an E to A substitution has been characterized. Homozygosity was observed in approximately 10% of Canadian individuals. This polymorphism was associated with decreased enzyme activity; homozygotes had approximately 60% of control activity in lymphocytes.

A sequence change (C1298A) has been identified. Heterozygotes for both the C677T and the A1298C mutation, approximately 15% of individuals, had 50%–60% of control activity, a value that was lower than that seen in single heterozygotes for the C677T variant. No individuals were homozygous for both mutations. A silent genetic variant T1317C, was identified in the same exon. It was relatively infrequent (allele frequency=5%) in the study group, but was common in a small sample of African individuals (allele frequency=39%).

In addition, by virtue of the role of MTHFR in folate-dependent homocysteine metabolism, the C677T mutation predisposes to mild hyperhomocysteinemia, a risk factor for vascular disease, in the presence of low folate status. By the present invention, the frequency of the A1298C variant has been determined and its potential impact on enzyme function has been assessed.

Patients with spina bifida and mothers of patients were recruited from the Spina Bifida Clinic at the Montreal Children's Hospital following approval from the Institutional Review Board. Control children and mothers of controls were recruited from the same institution. Blood samples were used to prepare DNA from peripheral leukocytes, to assay MTHFR activity in lymphocyte extracts, and to measure total plasma homocysteine (tHcy). The presence of the C677T mutation (A to V) was evaluated by PCR and HinfI digestion (2). The A1298C mutation was initially examined by PCR and MboII digestion (5). The silent mutation, T1317C, was identified by SSCP and sequence analysis in a patient with severe MTHFR deficiency and homocystinuria. This patient, an African-American female, already carries a previously-described splice mutation (patient 354 (8)). Since this mutation also creates a MboII site and results in a digestion pattern identical to that of the A1298C mutation, distinct artificially-created restriction sites were used to distinguish between these 2 mutations. Detection of the A1298C polymorphism was performed with the use of the sense primer 5'-GGGAGGAGCTGACCAGTGCAG-3' and the antisense primer (5'-GGGGTCAGGCCAGGGGCAG-3'), such that the 138 bp PCR fragment was digested into 119 bp and 19 bp fragments by Fnu4HI in the presence of the C allele. An antisense primer (5'-GGTTCTCCCGAGAGGTAAAGATC-3'), which introduces a TaqI site, was similarly designed to identify the C allele of the T1317C polymorphism.

Together with a sense primer (5'-CTGGGGATGTGGTGGCACTGC-3'), the 227 bp fragment is digested into 202 bp and 25 bp fragments.

TABLE 5

Genotype distributions, MTHFR activity (nmol formaldehyde/mg protein/hour), and total plasma homocysteine (tHcy;$\mu$M) for mothers and children

| | | E/E | | | E/A | | | A/A | | |
|---|---|---|---|---|---|---|---|---|---|---|
| | | A/A | A/V | V/V | A/A | A/V | V/V | A/A | A/V | V/V |
| Mothers (n = 141) | | | | | | | | | | |
| # | | 24 | 32 | 19 | 27 | 26 | 0 | 13 | 0 | 0 |
| % | | 17 | 23 | 13 | 19 | 18 | 0 | 9 | 0 | 0 |
| MTHFR | | 49.0 ± 18.9 [14] | 33.0 ± 10.8 [19]* | 15.7 ± 4.5 [11]* | 45.0 ± 16.0 [15] | 30.2 ± 19.3 [15]* | — | 32.1 ± 9.0 [7]* | — | — |
| THcy | | 9.5 ± 3.1 [24] | 10.0 ± 3.2 [32] | 12.2 ± 7.1 [19]** | 8.4 ± 2.1 [25] | 10.0 ± 3.1 [26] | — | 9.5 ± 2.0 [13] | — | — |

TABLE 5-continued

Genotype distributions, MTHFR activity (nmol formaldehyde/mg protein/hour), and total plasma homocysteine (tHcy;$\mu$M) for mothers and children

| | E/E | | | E/A | | | A/A | | |
|---|---|---|---|---|---|---|---|---|---|
| | A/A | A/V | V/V | A/A | A/V | V/V | A/A | A/V | V/V |
| | | | | Children (n = 133) | | | | | |
| # | 23 | 43 | 18 | 20 | 15 | 1 | 13 | 0 | 0 |
| % | 17 | 32 | 13 | 15 | 11 | 1 | 10 | 0 | 0 |
| MTHFR | 52.0 ± 17.0 [12] | 38.2 ± 15.0 [27]* | 16.2 ± 5.3 [11]* | 35.7 ± 9.7 [18]* | 26.1 ± 5.0 [9]* | 21.6 [1] | 29.5 ± 10.3 [6]* | — | — |
| THcy | 7.6 ± 2.5 [23] | 8.2 ± 3.0 [43] | 9.7 ± 5.1 [18]** | 7.5 ± 2.3 [20] | 8.1 ± 2.8 [15] | 9.5 [1] | 7.4 ± 1.5 [13] | — | — |

The three A1298C genotypes and the three C677T genotypes are designated by the amino acid codes: EE, EA, AA, and AA, AV, VV, respectively. Statistical significance was assessed by student t-test, in comparison with EEAA values. *($p < 0.05$); **($p \leq 0.07$). Standard deviations are given and square brackets indicate the number of individuals for whom MTHFR activities and homocysteine levels were available.

The frequencies of the three genotypes for the A1298C mutation (EE, EA and AA) were not different between case and control mothers, or between case and control children (data not shown). Consequently, all the mothers and all the children were grouped together for analyses (Table 5). Nine % of mothers had the homozygous AA genotype while 37% were heterozygous. This frequency is quite similar to the frequency of the homozygous mutant genotype (VV) for the C677T polymorphism. In the MTHFR human cDNA sequence mentioned above, the cDNA contained the C nucleotide at bp 1298 change as a C1298A substitution. Since the A nucleotide is clearly the more frequent base at this position, the A1298C nomenclature was chosen.

Since the C677T mutation (A to V) decreases MTHFR activity and increases homocysteine levels, the three genotype groups for the A1298C (E to A) mutation were further stratified by the genotype for the A to V mutation, to avoid the confounding influence of the latter polymorphism on MTHFR activity and homocysteine levels. The frequencies of the 9 genotypes, with MTHFR activity and homocysteine levels for each genotype, are shown in Table 5. If the mothers and children without either mutation i.e. EE/AA are used as the reference (control) group, the mothers and children that are homozygous for the A1298C mutation (AAAA) have approximately 65% and 57%, respectively, of control MTHFR activity. Heterozygotes for the C677T change alone (EEAV) have approximately 70% of control activity, as reported in other studies, while double heterozygotes (EAAV), 18% of mothers and 11% of children, have an additional loss of activity (approximately 62% and 50% of control values, respectively).

Homocysteine levels were not significantly increased by the A1298C mutation, but homocysteine was levated (with borderline significance, $p \leq 0.07$) in mothers and children who were homozygous for the C677T change. The small number of individuals who were homozygous for the A1298C mutation (n=13) may have influenced the power of the statistical analyses and precluded an investigation of the genetic-nutrient interactive effect that leads to mild hyperhomocysteinemia, as seen in individuals with the C677T mutation.

The T1317C substitution does not alter the amino acid (phenylalanine) and is likely a benign change, although a splicing defect cannot be ruled out at the present time. In an evaluation of 38 control mothers from this study, 2 were found to be heterozygous and one was identified as a homozygote, resulting in an allele frequency of 5% (4/76). Since this substitution was identified in an African-American female, control African individuals were also examined (n=9). Seven of these were heterozygous, resulting in an allele frequency of 39% (7/18).

The A1298C mutation clearly reduces MTHFR activity, albeit to a lesser extent than the C677T mutation. Consequently its effect on homocysteine levels is also attenuated and, in fact, may only be significant when an individual carries both mutations and/or has poor nutrient status. However, since double heterozygotes are estimated to represent approximately 15% of the population, this variant should be examined in conjunction with the C677T ariant in studies of hyperhomocysteinemia.

The A1298C mutation is clearly polymorphic in Canadian individuals and should be examined in other populations. The A nucleotide is likely to be the ancestral sequence since it represents the more common allele, although the original human MTHFR cDNA sequence (GenBank accession number U09806) carried the C nucleotide. This polymorphism is similar in frequency to the C677T polymorphism. Presumably the two substitutions arose separately on a A1298/C677 or E/A haplotype, since the haplotype with both substitutions (C1298/T677 or A/V) is extremely rare. One such haplotype was seen in a child with the EAVV genotype, suggesting a recombinant chromosome.

Doubly homozygous individuals (AAVV) were not observed in this study. Since the double mutation in cis is rare, it is possible that not enough alleles were studied. Larger studies in other populations might result in the identification of these individuals. Presumably the MTHFR activity would be even lower and homocysteine levels might be higher than those observed thus far.

The C677T polymorphism in exon 4 is within the N-terminal catalytic domain of the enzyme whereas the A1298C polymorphism in exon 7 is within the C-terminal regulatory domain. The more dramatic effect on enzyme activity with the first polymorphism may be a consequence of its location within the catalytic region. The second polymorphism could affect enzyme regulation, possibly by S-adenosylmethionine, an allosteric inhibitor of MTHFR, which is known to bind in the C-terminal region.

Many studies have examined the effects of the C677T polymorphism on MTHFR enzyme activity and on homocysteine levels. Although the correlation between the presence of this substitution and decreased enzyme activity/ increased homocysteine levels has been quite good, the variability in results, particularly in heterozygous individuals, may reflect the presence of a second common variant in the population.

The third variant, T1317C, was present on 5% of alleles in Canadian individuals but appears to be extremely common in individuals of African ancestry. The methodology outlined in this report should be used to assess the frequency of the A1298C and T1317C in other populations, since the use of the MboII restriction site for analysis of the A1298C change, as first reported, would not discriminate between the 2 polymorphisms.

The C677T mutation is a risk factor for hyperhomocysteinemia and has been implicated in both neural tube defects and vascular disease.

Gene structure of human and mouse methylenetetrahydrofolate reductase (MTHFR)

A human cDNA for MTHFR, 2.2 kb in length, has been expressed and shown to result in a catalytically-active enzyme of approximately 70 kDa. Fifteen mutations have been identified in the MTHFR gene: 14 rare mutations associated with severe enzymatic deficiency and one common variant associated with a milder deficiency. The common polymorphism has been implicated in three multifactorial diseases: occlusive vascular disease, neural tube defects and colon cancer. The human gene has been mapped to hromosomal region 1p36.3 while the mouse gene has been localized to distal Chromosome 4. The isolation and characterization of the human and mouse genes for MTHFR is herein reported. A human genomic clone (17 kb) was found to contain the entire cDNA sequence of 2.2 kb; there were 11 exons ranging in size from 102 bp to 432 bp. Intron sizes ranged from 250 bp to 1.5 kb with one exception of 4.2 kb. The mouse genomic clones (19 kb) start 7 kb 5' to exon 1 and extend to the end of the coding sequence. The mouse amino acid sequence is approximately 90% identical to the corresponding human sequence. The exon sizes, locations of intronic boundaries, and intron sizes are also quite similar between the two species. The availability of human genomic clones has been useful in designing primers for exon amplification and mutation detection. The mouse genomic clones may be used to make constructs for gene targeting and generation of mouse models for MTHFR deficiency.

A common polymorphism, C677T has been identified, which converts an alanine codon to valine (Frosst et al., 1995). This common polymorphism, which is present on approximately 35% of alleles in the North American population, encodes the thermolabile variant and predisposes to mild hyperhomocysteinemia when folate status is low (Frosst et al., 1995; Jacques et al., 1996; Christensen et al., 1997). This genetic-nutrient interactive effect is believed to be a risk factor for arteriosclerosis (Frosst et al, 1995) and neural tube defects. In contrast, the mutant homozygous genotype may decrease the risk for colon cancer.

The characterization of the genomic structure for human MTHFR is reported herein. The corresponding analysis of the mouse gene, with a comparison of the overall organization of the gene and the amino acid sequences in these two species, is also shown.

Screening of genomic libraries

Genomic libraries were screened using standard methods of plaque hybridization. The 2.2 kb human cDNA was radiolabelled and used as a probe in screening both human and murine genomic libraries. Screening for the human gene was performed on a phage library of partial EcoRI digestion fragments from total genomic DNA (ATCC # 37385), and on a phage library of chromosome 1-specific complete EcoRI digestion fragments (ATCC# 57738). Screening for the mouse gene was performed on a γDASH library of partial Sau3A digestion fragments from total genomic DNA of mouse strain 129SV (obtained from Dr. J. Rossant, University of Toronto). Positive clones were purified by sequential rounds of screening and isolation, and phage DNA was isolated using phage DNA isolation columns (QIAGEN). Human clones were digested with EcoRI to release the inserts, and then with XbaI to facilitate cloning into Bluescript plasmid (Stratagene). The mouse clones were digested with SalI or EcoRI, and the inserts were subcloned into Bluescript.

Characterization of mouse cDNA sequences

Mouse genomic clones were sequenced (Sequenase kit, Amersham) using human cDNA primers spanning most of the available 2.2 kb cDNA. These sequences were then used to generate mouse-specific cDNA primers. The mouse-specific primers were used in PCR amplification of overlapping cDNA fragments from reverse-transcribed mouse liver RNA. The PCR products were subcloned into the PCRII vector (Invitrogen) and sequenced. Two different species of mouse (C57B1/6J and ct) were used to generate MTHFR sequence by RT-PCR, to ensure that the PCR protocol did not generate sequencing errors.

Characterization of intron boundaries and sizes, and restriction analysis of human and mouse genes Primers from cDNA sequences of human and mouse were used to sequence the respective genomic clones. Intron boundaries were determined from regions of divergence between cDNA and genomic clone sequences, and by the identification of splice acceptor and donor consensus sites. Intronic sequences were obtained for 40–50 bp from the junctions and are shown in FIGS. 12A–12B (human) and FIGS. 13A–13B (mouse). The same cDNA primers were used in PCR amplification of total genomic DNA and of genomic clones to determine the approximate sizes of introns in the human and mouse genes. Table 6 lists the locations and approximate sizes of introns for both species. The PCR products were analyzed by restriction enzyme digestion to generate a preliminary restriction map of the gene. This restriction map was then confirmed by restriction analysis of the genomic clones in Bluescript.

Referring to FIGS. 12A–12B, the bp location of the exons within the cDNA, in parentheses, is based on the published human cDNA sequence (GenBank accession number U09806). Bp 1 is 12 bp upstream from the ATG in the original cDNA; an asterisk indicates the equivalent base here. Exon 1 contains the ATG start site (underlined), and exon 11 contains the termination codon (underlined). Uppercase characters indicate exonic sequences, and lower case characters are intronic. Consensus splice junction sequences are underlined. The 3' boundary of exon 11 has been designated by the location of the polyA tail.

Referring to FIGS. 13A–13B, the bp location of the exons within the cDNA, in parentheses, is based on the equivalent bp 1 of the human sequences in FIGS. 12A–12B (bp 1 is indicated by an asterisk). Exon 1 contains the ATG start site (underlined), and exon 11 contains the termination codon (doubly underlined). Uppercase characters indicate exonic sequences, and lower case characters are intronic. Consensus splice junction sequences are underlined. The 3' boundary of exon 11 is designated as the termination codon, since the site of polyadenylation is unknown. Also underlined in exon 11 is the first repeat of the 52 bp repeated element.

Figure 14:
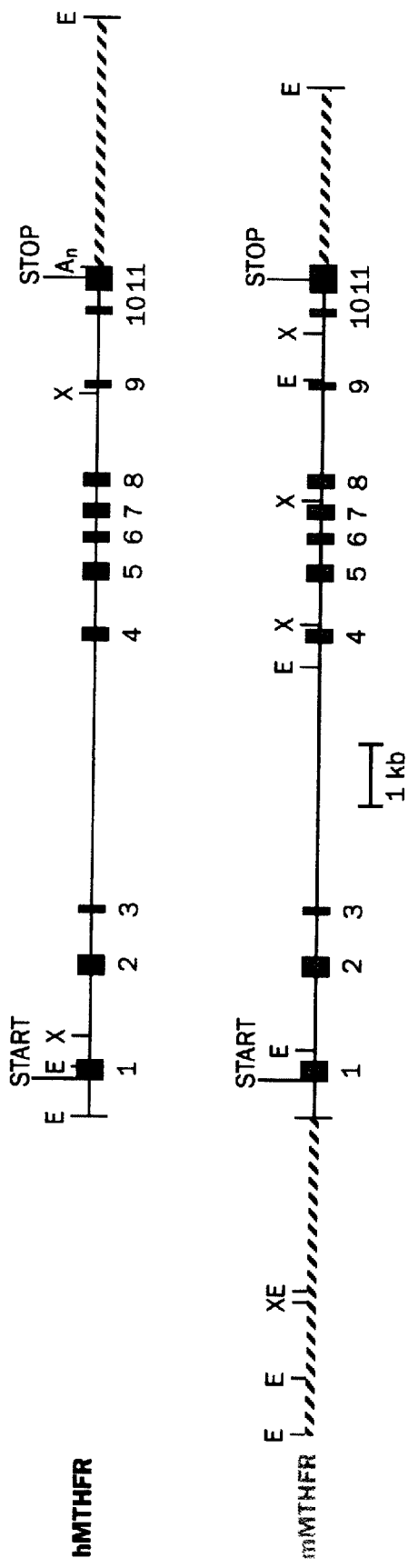
FIG. 14 illustrates intron sizes and locations for both human and mouse genes.

Referring to FIG. 14, exon sizes for human and mouse are reported in FIGS. 12A–12B and FIGS. 13A–13B, respectively. Exons are indicated in shaded boxes. Uncharacterized regions of the gene are hatched, and exon numbering corresponds to FIGS. 12A–12B and 13A–13B. E=EcoRI; X=XbaI; $A_n$=polyadenylation site. The EcoRI restriction site at the 5' end of the mouse gene is part of the phage polylinker sequence.

Referring to FIG. 15, residues that are identical to the human MTHFR sequence are shown as empty boxes, and gaps in amino acid homology are represented by a dash.

Human genomic clones

The genomic clones isolated from the human libraries contained a 16 kb EcoRI fragment, encompassing part of exon 1 and exons 2 through 11, and a 1 kb EcoRI fragment containing most of exon 1. Exon 1 is defined as the most 5' exon from the previously published cDNA sequence; it contains the ATG start site that was used to express the human cDNA in bacterial extracts (Frosst et al. 1995). A graphic representation of the human gene and its restriction map are depicted in FIG. 3. The sequences of each exon and 50 bp of flanking intronic sequences are shown in FIGS. 12A–12B. Exons range in size from 102 bp to 432 bp, and the critical dinucleotides in the 5' and 3' splice site consensus sequences (GT and AG, respectively) are underlined. The 3' boundary of exon 11 is defined by the site of polyadenylation in the cDNA; a possible polyadenylation signal (AACCTA) is present 15 bp upstream of the polyadenylation site, although it varies from the consensus sequence. Table 6 lists the locations and approximate sizes of introns as determined by PCR amplification; the introns range in size from approximately 250 bp to 4.2 kb.

Mouse genomic clones

Genomic clones isolated from the mouse libraries were digested with EcoRI for subcloning and characterization. Exon nomenclature is based on the corresponding human gene sequences. FIGS. 13A–13B list all known exons and their sizes, with 40 to 50 bp of flanking intronic sequences. FIG. 14 shows a graphic representation of the mouse genomic structure aligned with the human gene. The size of exon 11 is undetermined, since the sequence for this region was determined directly from the genomic clones. The termination codon is located within a region of 52 bp which is repeated 3 times in the gene. The significance of this, if any, is unknown at the present time. The dinucleotides of the splice junctions (underlined in FIGS. 13A–13B) are in agreement with consensus sequences. Table 6 lists the approximate sizes of introns as determined by PCR, and their bp location in the cDNA. The introns range in size from approximately 250 bp to 4.2 kb.

Comparison of the human and mouse genes

The human and mouse genes are very similar in size and structure (FIG. 14). The introns are similar in size, and identical in location within the coding sequence. However, the mouse cDNA is one amino acid shorter in exon 1 which causes a shift in bp numbering of the mouse cDNA (Table 6, FIGS. 13A–13B). Exon 1 was defined from the original published human cDNA, based on the presence of a translation start codon. In both human and mouse genes, the 5' boundary of exon 1 was assigned after the isolation of several non-coding cDNA extensions that are generated by alternative splicing from this junction. Characterization of these 5° cDNA extensions is in progress. The nucleotide sequences of the human and mouse genes are very similar within coding regions, but homology decreases dramatically in the 3' UTR region and within introns.

Human and mouse primary amino acid sequence homology

The primary amino acid sequences of human and mouse were compared to each other, and aligned with the sequence of the MetF (MTHFR) enzyme from bacteria (FIG. 15). The human and mouse amino acid sequences are almost 90% identical. As previously observed, only the 5' half of the mammalian sequences align with the bacterial enzyme; bacterial MTHFR has the same catalytic activity as the mammalian enzyme but lacks the regulatory region in the C-terminal domain. The murine amino acid sequence is two amino acids shorter than the human sequence: one less amino acid in exon 1 and one less in exon 11.

The isolation of the human MTHFR gene and the analysis of gene structure are part of an ongoing effort to study MTHFR deficiency in homocystinuria and in multifactorial diseases. The availability of genetic structure information and of intronic sequences will help in the mutational analysis of patients suffering from MTHFR deficiency and in the characterization of the 5' regulatory region.

Expression analysis of the 2.2 kb cDNA in a bacterial expression system resulted in a catalytically-active 70 kDa protein (Frosst et al. 1995). A MTHFR polypeptide of this size was observed in some human tissues on Western blots, but a larger isozyme (77 kDa), corresponding to the estimated size of the porcine polypeptide, was observed in all the examined tissues. These data suggested the presence of protein isoforms for MTHFR that could be tissue-specific (Frosst et al., 1995). Since human or mouse sequences homologous to the N-terminal porcine amino acid sequences have not been identified, it is assumed that the missing sequences required to encode the larger isoform are 5' to the available cDNA sequences. Two mRNAs for human MTHFR (approximately 7.5 and 8.5 kb) have been seen in all tissues on Northern blots (data not shown), suggesting very large UTRs. The isolation of 5' coding sequences has been complicated by the presence of several alternatively-spliced 5' non-coding extensions that splice into exon 1. The alternative splicing into exon 1 has been observed in both human and mouse MTHFR. The long UTRs and the alternative splicing events suggest that the regulation of this important gene may be quite complex.

Nonetheless, the available information has been critical for identification of mutations in patients with various forms of MTHFR deficiency. The mouse sequences in exons 1 and 2 have been useful in the design of antisense oligonucleotides to successfully inhibit MTHFR in mouse embryo cultures and disrupt development of the neural tube (Lanoue et al. 1997). The isolation and characterization of mouse genomic clones is essential for construction of targeting vectors to generate mouse models for MTHFR deficiency.

TABLE 6

Approximate sizes of introns, and their locations in human and mouse MTHFR cDNA

| Intron | Approximate size (kb) | Human location[1] | Mouse Location[1] |
| --- | --- | --- | --- |
| 1 | 1.5 | 248–249 | 245–246 |
| 2 | 0.8 | 487–488 | 484–485 |
| 3 | 4.2 | 598–599 | 595–596 |
| 4 | 0.8 | 792–793 | 789–790 |
| 5 | 0.35 | 1043–1044 | 1040–1041 |
| 6 | 0.25 | 1178–1179 | 1175–1176 |
| 7 | 0.3 | 1359–1360 | 1356–1357 |
| 8 | 1.5 | 1542–1543 | 1539–1540 |
| 9 | 1.3 | 1644–1645 | 1641–1642 |
| 10 | 0.3 | 1764–1765 | 1761–1762 |

[1]Base pairs flanking introns, from FIGS. 1 and 2. Bp1 is 12 bp upstream from the ATG, as in the original report of the cDNA sequence (Goyette et al. 1994).

Various doses of methotrexate (a drug used in treatment of cancer and arthritis, possibly other diseases) were added to colon carcinoma lines in culture. Much lower doses of methotrexate are needed to kill the lines that carry the 677C→T mutation in MTHFR, compared to lines that do not carry this mutation. The IC50 (concentration needed to kill half the cells) is approximately 20 nM for lines with the mutation and approximately 150 nM for lines without the mutation. To extrapolate to the human condition, patients with this MTHFR mutation might require lower doses of methotrexate for therapy, or might be subject to methotrexate toxicity at high doses.

TABLE 7

Summary of BMD analysis
Entire cohort: Values are means +/− SE

|  | Genotype 1/1 | Genotype 1/2 | Genotype 2/2 |
| --- | --- | --- | --- |
| Spinal Z score | −1.06 (0.193) | −1.25 (0.176) | −1.86 (0.238) |
| Femoral neck Z score | −0.69 (0.134) | −0.78 (0.126) | −0.87 (0.228) |
| Trochanter Z score | −0.60 (0.142) | −0.52 (0.134) | −1.15 (0.249) |
| Ward's triangle Z score | −0.67 (0.147) | −0.80 (0.139) | −0.96 (0.257) |

Values for bone mineral density in a group of individuals who were examined for the MTHFR 677C→T mutation.
Genotype 1/1 = normal C/C
Genotype 1/2 = carriers C/T
Genotype 2/2 = homozygous mutant T/T As seen on Table 7, the lower the score, the lower the bone mineral density and therefore the higher the risk for osteoporosis. The results suggest that the homozygous mutant genotype (2/2) is asssociated with lower bone mineral density and therefore higher risk of osteoporosis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for identifying an individual having an MTHFR allele variant, said method comprising analyzing a nucleic acid sample obtained from said individual to determine whether said sample comprises at least one MTHFR allele variant.

2. The method of claim 1, wherein said MTHFR allele variant leads to a decrease in MTHFR activity.

3. The method of claim 1, wherein said MTHFR allele variant is selected from the group consisting of 167G/A, 482G/A, 559C/T, 677C/T, 692C/T, 764C/T, 792+1A/T, 985C/T, 1015C/T, and 1081C/T.

4. The method of claim 1, wherein said MTHFR allele variant is 677C/T.

5. The method of claim 1, wherein said MTHFR allele variant is associated with a disorder selected from the group consisting of cardiovascular disorders, coronary and arterial disorders, cancer, osteoporosis, and neurological disorders.

6. The method of claim 1, wherein said MTHFR allele variant is associated with a neural tube defect.

7. The method of claim 1, wherein said MTHFR allele variant is associated with a disorder influenced by folic acid metabolism.

8. A method for identifying an individual having an MTHFR allele variant, said method comprising analyzing a nucleic acid sample obtained from said individual to determine whether said sample comprises the MTHFR allele variant 1317T/C.

9. The method of claim 8, wherein said MTHFR allele variant leads to a decrease in MTHFR activity.

10. The method of claim 8, wherein said MTHFR allele variant is associated with a disorder selected from the group consisting of cardiovascular disorders, coronary and arterial disorders, cancer, osteoporosis, and neurological disorders.

11. The method of claim 8, wherein said MTHFR allele variant is associated with a neural tube defect.

12. The method of claim 8, wherein said MTHFR allele variant is associated with a disorder influenced by folic acid metabolism.

* * * * *

UNITED STATES PATENT AND TRADEMARK OFFICE
CERTIFICATE OF CORRECTION

PATENT NO. : 6,218,120 B1
DATED : April 17, 2001
INVENTOR(S) : Rima Rozen et al.

Figure 9D:
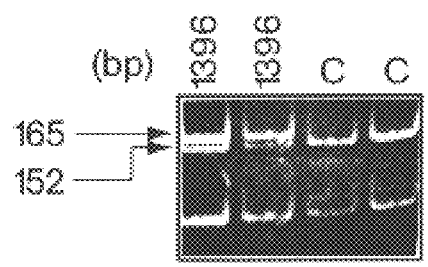

It is certified that error appears in the above-identified patent and that said Letters Patent is hereby corrected as shown below:

Title page,
Item [56], OTHER PUBLICATIONS, please delete one of the duplicate listing for "Goyette P et al., AM. J. Hum. Genet., 1995, 56:1052-1059" and "Frosst P et al., Nature Genetics, 1995, 10:111-113"; and in the "Kuivenhoven et al.," citation, replace "Esterr" with -- Ester --; and in the "Poirer et al.," citation, replace "USA92" with -- USA 92 --;

Column 1,
Line 5, after "1995" insert -- , which claims priority to Great Britain application No. 9410620.0, filed May 26, 1994 --;

Column 2,
Line 51, replace "may also contribution" with -- may also contribute --;

Column 5,
Line 14, replace "form" with -- from --;

Column 6,
Line 40, replace "$\gamma$gt10" with -- $\lambda$gt10 --;

Column 7,
Line 9, replace "$\gamma$gt10" with -- $\lambda$gt10 --;

Column 9,
Line 65, replace "values=9.7" with -- values = 9.7 --;
Line 66, replace "min.=28%" with -- min. = 28% --;

Columns 11 and 12,
Table 1, insert -- I -- under the Location Column in lines 56 and 60;

Column 13,
Line 41, replace "51" with -- 5´ --;

Column 15,
Line 27, delete the word "Fig."
Line 28, replace "9D" with -- FIG. 9D --;

UNITED STATES PATENT AND TRADEMARK OFFICE
CERTIFICATE OF CORRECTION

PATENT NO.     : 6,218,120 B1
DATED          : April 17, 2001
INVENTOR(S)    : Rima Rozen et al.

It is certified that error appears in the above-identified patent and that said Letters Patent is hereby corrected as shown below:

Column 25,
Line 54, replace "levated" with -- elevated --;

Column 26,
Line 34, replace "ariant" with -- variant --;

Column 27,
Line 29, replace "hromosomal" with -- chromosomal --;

Column 28,
Line 5, replace "γDASH" with -- λDASH --;

Column 30,
Line 3, replace "5°" with -- 5´ --.

Signed and Sealed this

Fifteenth Day of April, 2003

JAMES E. ROGAN
*Director of the United States Patent and Trademark Office*